United States Patent
Kaneda et al.

(10) Patent No.: US 12,238,947 B2
(45) Date of Patent: Feb. 25, 2025

(54) SOLID-STATE IMAGING DEVICE, METHOD OF MANUFACTURING SOLID-STATE IMAGING DEVICE, AND ELECTRONIC EQUIPMENT

(71) Applicant: SONY SEMICONDUCTOR SOLUTIONS CORPORATION, Kanagawa (JP)

(72) Inventors: Yukio Kaneda, Kanagawa (JP); Nobuyuki Kuboi, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 433 days.

(21) Appl. No.: 17/432,426

(22) PCT Filed: Jan. 30, 2020

(86) PCT No.: PCT/JP2020/003449
§ 371 (c)(1),
(2) Date: Aug. 19, 2021

(87) PCT Pub. No.: WO2020/179300
PCT Pub. Date: Sep. 10, 2020

(65) Prior Publication Data
US 2022/0020819 A1  Jan. 20, 2022

(30) Foreign Application Priority Data
Mar. 4, 2019 (JP) ................. 2019-038974

(51) Int. Cl.
*H10K 39/32* (2023.01)
*A61B 1/05* (2006.01)

(52) U.S. Cl.
CPC ............... *H10K 39/32* (2023.02); *A61B 1/05* (2013.01)

(58) Field of Classification Search
CPC ............. H10K 39/32; H01L 27/14647; H01L 27/14652; H01L 27/14683
See application file for complete search history.

(56) References Cited

U.S. PATENT DOCUMENTS

2007/0215912 A1* 9/2007 Kido ................. H01L 27/14641
257/257
2016/0037098 A1 2/2016 Lee et al.
(Continued)

FOREIGN PATENT DOCUMENTS

CN 105308749 A 2/2016
CN 107146850 A 9/2017
(Continued)

OTHER PUBLICATIONS

International Search Report and Written Opinion of PCT Application No. PCT/JP2020/003449, issued on Apr. 14, 2020, 11 pages of ISRWO.

*Primary Examiner* — Syed I Gheyas
(74) *Attorney, Agent, or Firm* — CHIP LAW GROUP

(57) ABSTRACT

A solid-state imaging device (1) according to the present disclosure includes a photoelectric conversion portion (30) including a first electrode (31), a photoelectric conversion layer (34) electrically connected to the first electrode (31), and a second electrode (35) provided on a surface on a light incidence side of the photoelectric conversion layer (34). The photoelectric conversion layer (34) has a protrusion region (34a) that protrudes from the second electrode (35) when seen in a plan view.

12 Claims, 50 Drawing Sheets

(56) References Cited

U.S. PATENT DOCUMENTS

| | | | |
|---|---|---|---|
| 2016/0093657 A1* | 3/2016 | Ryoki | ............... H01L 27/14665 |
| | | | 257/448 |
| 2016/0372520 A1* | 12/2016 | Joei | ........................ H10K 39/32 |
| 2017/0125469 A1 | 5/2017 | Ryoki | |
| 2018/0076252 A1 | 3/2018 | Togashi et al. | |
| 2018/0175102 A1 | 6/2018 | Togashi et al. | |
| 2021/0111218 A1* | 4/2021 | Nakamura | .......... G01T 1/20184 |

FOREIGN PATENT DOCUMENTS

| | | |
|---|---|---|
| CN | 206992154 U | 2/2018 |
| CN | 110246861 A | 9/2019 |
| CN | 110323237 A | 10/2019 |
| CN | 110459551 A | 11/2019 |
| EP | 3424089 A1 | 1/2019 |
| JP | 2006303468 A | 11/2006 |
| JP | 2015-015332 A | 1/2015 |
| JP | 2016-072389 A | 5/2016 |
| JP | 2017-157816 A | 9/2017 |
| KR | 10-2016-0017168 A | 2/2016 |
| KR | 10-2016-0030102 A | 3/2016 |
| KR | 10-2018-0121330 A | 11/2018 |
| TW | 201801297 A | 1/2018 |
| WO | 2015/001771 A1 | 1/2015 |
| WO | 2017/150540 A1 | 9/2017 |
| WO | 2018/181438 A1 | 10/2018 |

* cited by examiner

SOLID-STATE IMAGING DEVICE, METHOD OF MANUFACTURING SOLID-STATE IMAGING DEVICE, AND ELECTRONIC EQUIPMENT

CROSS REFERENCE TO RELATED APPLICATIONS

This application is a U.S. National Phase of International Patent Application No. PCT/JP2020/003449 filed on Jan. 30, 2020, which claims priority benefit of Japanese Patent Application No. JP 2019-038974 filed in the Japan Patent Office on Mar. 4, 2019. Each of the above-referenced applications is hereby incorporated herein by reference in its entirety.

TECHNICAL FIELD

The present disclosure relates to a solid-state imaging device, a method of manufacturing the solid-state imaging device, and electronic equipment.

BACKGROUND ART

In recent years, a structure in which an organic photoelectric conversion layer performing photoelectric conversion of incident light is stacked on a light incidence side of semiconductor layer has been proposed as a photoelectric conversion element used in an image sensor of a camera, and the like (see, for example, PTL 1).

CITATION LIST

Patent Literature

[PTL 1]
JP 2017-157816 A

SUMMARY

Technical Problem

However, in the above-described related art, in order to form a satisfactory photoelectric conversion layer in a manufacturing step for a solid-state imaging device, there is a fundamental need to form such a photoelectric conversion layer after a semiconductor process is completed to a certain degree.

For example, when it is assumed that a photoelectric conversion layer is formed before high-temperature annealing in a case where such annealing is performed as a semiconductor process, there is a concern that damage may occur in the photoelectric conversion layer which is an organic material due to the annealing.

Consequently, in the present disclosure, a solid-state imaging device in which a satisfactory photoelectric conversion layer is formed, a method of manufacturing the solid-state imaging device, and electronic equipment are proposed.

Solution to Problem

According to an aspect of the present invention, a solid-state imaging device is provided. The solid-state imaging device includes a photoelectric conversion portion that includes a first electrode, a photoelectric conversion layer electrically connected to the first electrode, and a second electrode provided on a surface on a light incidence side of the photoelectric conversion layer. The photoelectric conversion layer has a protrusion region that protrudes from the second electrode when seen in a plan view.

Advantageous Effects of Invention

According to the present disclosure, it is possible to provide a solid-state imaging device in which a satisfactory photoelectric conversion layer is formed, a method of manufacturing the solid-state imaging device, and electronic equipment. Meanwhile, the advantageous effects described here are not necessarily limiting and other advantageous effects described in the present disclosure may be obtained.

DESCRIPTION OF EMBODIMENTS

Figure 1:
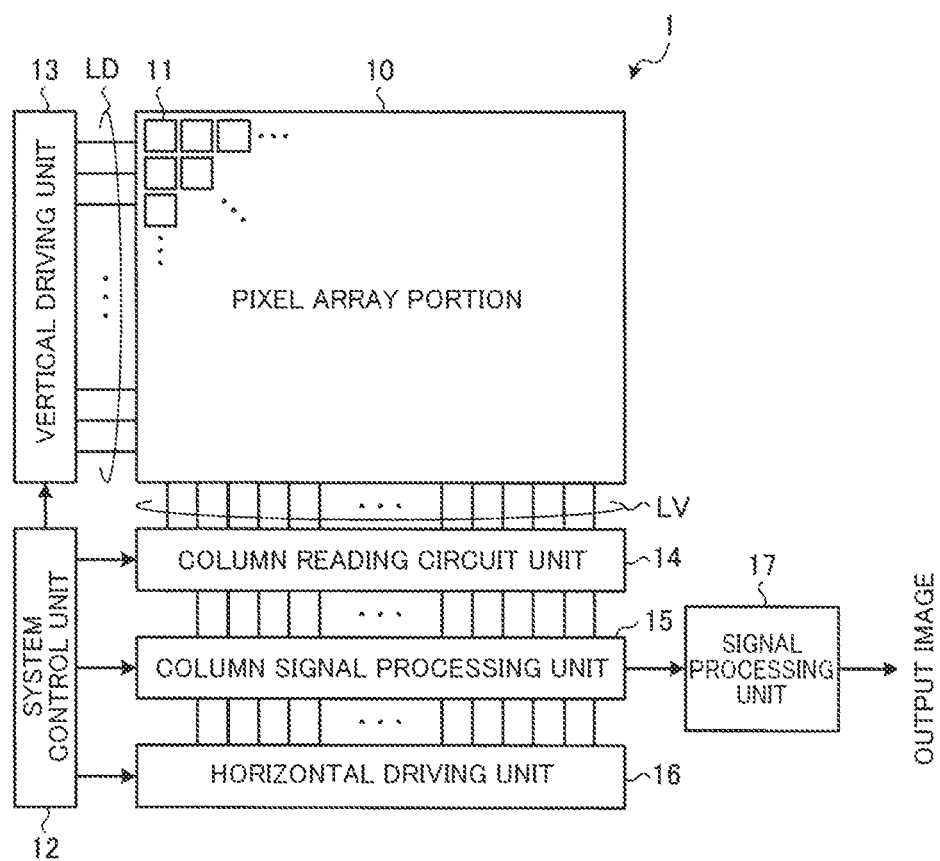
FIG. 1 is a system configuration diagram illustrating an overall configuration example of a solid-state imaging device according to an embodiment of the present disclosure.

Hereinafter, embodiments of the present disclosure will be described in detail with reference to the drawings. Meanwhile, in the following embodiments, the same portions will be denoted by the same reference numerals and signs, and repeated description thereof will be omitted.

In recent years, a structure in which an organic photoelectric conversion layer performing photoelectric conversion of incident light is stacked on a light incidence side of semiconductor layer has been proposed as a photoelectric conversion element used in an image sensor of a camera, and the like.

However, in the above-described related art, in order to form a satisfactory photoelectric conversion layer in a manufacturing step for a solid-state imaging device, there is a fundamental need to form such a photoelectric conversion layer after a semiconductor process is completed to a certain degree.

For example, when it is assumed that a photoelectric conversion layer is formed before high-temperature annealing in a case where such annealing is performed as a semiconductor process, there is a concern that damage may occur in the photoelectric conversion layer which is an organic material due to the annealing.

On the other hand, in a case where the temperature of annealing is set to be lower than a heat-resistant temperature of a photoelectric conversion layer so that damage does not occur in the photoelectric conversion layer, a desired annealing effect is not obtained, and thus it becomes difficult to obtain satisfactory element characteristics.

Consequently, realization of technology capable of forming a satisfactory photoelectric conversion layer without causing damage in a photoelectric conversion layer formed of an organic material due to annealing or the like is anticipated.

Configuration of Solid-State Imaging Device

FIG. 1 is a system configuration diagram illustrating an overall configuration example of a solid-state imaging device 1 according to an embodiment of the present disclosure. As illustrated in FIG. 1, the solid-state imaging device 1 which is a CMOS image sensor includes a pixel array portion 10, a system control unit 12, a vertical driving unit 13, a column reading circuit unit 14, a column signal processing unit 15, a horizontal driving unit 16, and a signal processing unit 17.

The pixel array portion 10, the system control unit 12, the vertical driving unit 13, the column reading circuit unit 14, the column signal processing unit 15, the horizontal driving unit 16, and the signal processing unit 17 are provided on the same semiconductor substrate or a plurality of stacked semiconductor substrates which are electrically connected to each other.

In the pixel array portion 10, effective unit pixels (hereinafter referred to as "unit pixels") 11 that include photoelectric conversion elements (a photoelectric conversion portion 30 (see FIG. 2) and the like) capable of photoelectrically converting and storing a charge amount corresponding to the amount of incident light and outputting the charge amount as a signal are arrayed two-dimensionally in a matrix.

In addition, the pixel array portion 10 may include a region in which dummy unit pixels having a structure that does not include a photoelectric conversion portion 30 and the like, light-shielding unit pixels in which incident light is blocked from the outside by shielding a light receiving surface from light, and the like are disposed in a row and/or column form in addition to the effective unit pixels 11.

Meanwhile, the light-shielding unit pixels may have a similar configuration to the effective unit pixels 11 except for the structure in which the light receiving surface is shielded from light. Hereinafter, photoelectric charge having a charge amount corresponding to the amount of incident light is referred to simply as "charge" and the unit pixels 11 are also referred to simply as "pixels" in some cases.

In the pixel array portion 10, a pixel driving line LD is formed for each row in a right-left direction in the drawing (a direction in which pixels of a pixel row are arrayed), and a vertical pixel wiring LV is formed for each column in an up-down direction in the drawing (a direction in which pixels of a pixel column are arrayed) in a pixel array having a matrix form. One end of the pixel driving line LD is connected to an output end corresponding to each row of the vertical driving unit 13.

The column reading circuit unit 14 includes at least a circuit that supplies a constant current to the unit pixels 11 for each column in a selected row in the pixel array portion 10, a current mirror circuit, a switching switch of the unit pixels 11 to be read, and the like.

In addition, the column reading circuit unit 14 constitutes an amplifier along with a transistor in a selected pixel in the pixel array portion 10, converts a photoelectric charge signal into a voltage signal, and outputs the voltage signal to the vertical pixel wiring LV.

The vertical driving unit 13 includes a shift register, an address decoder, and the like, and drives all the unit pixels 11 of the pixel array portion 10 at the same time in all of the pixels, in units of rows, or the like. Although a specific configuration of the vertical driving unit 13 is not illustrated in the drawing, the vertical driving unit 13 is configured to include a reading scanning system, a sweeping scanning system, or a collective sweeping and collective transfer system.

The reading scanning system selects and scans the unit pixels 11 of the pixel array portion 10 in order in units of rows in order to read pixel signals from the unit pixels 11. In the case of row driving (a rolling shutter operation), regarding sweeping, sweeping scanning is performed earlier by a time of a shutter speed than reading scanning with respect to a reading row in which reading scanning is performed by a reading scanning system.

In addition, in the case of global exposure (a global shutter operation), collective sweeping is performed earlier by a time of a shutter speed than collective transfer. By such sweeping, unnecessary charge is swept (reset) from the photoelectric conversion portion 30 and the like of the unit pixels 11 in a reading row. In addition, by sweeping (resetting) unnecessary charges, a so-called electronic shutter operation is performed.

Here, the electronic shutter operation is an operation of discarding unnecessary photoelectric charge collected in the photoelectric conversion portion 30 and the like up to recently and newly starting exposure (starting storage of photoelectric charge).

A signal read through the reading operation in the reading scanning system corresponds to the amount of light incident after the immediately previous reading operation or the electronic shutter operation. In the case of row driving, a period from a reading timing in the immediately previous reading operation or a sweeping timing in the electronic shutter operation to a reading timing in a present reading operation is a storage time (an exposure time) of photoelectric charge in the unit pixels 11. In the case of global exposure, a time from the collective sweeping to collective transfer is a storage time (an exposure time).

A pixel signal output from each unit pixel 11 in a pixel row selected and scanned by the vertical driving unit 13 is supplied to the column signal processing unit 15 through each of the vertical pixel wirings LV. The column signal processing unit 15 performs predetermined signal processing on the pixel signals output from the unit pixels 11 in the selected row through the vertical pixel wiring LV for each pixel column of the pixel array portion 10 and temporarily holds the pixel signals after the signal processing.

Specifically, the column signal processing unit 15 performs at least noise removal, for example, correlated double sampling (CDS) as signal processing. By the CDS processing performed by the column signal processing unit 15, fixed pattern noise specific to the pixels, such as reset noise or a variation in a threshold value of an amplification transistor AMP, is removed.

Meanwhile, the column signal processing unit 15 can also be provided with, for example, an AD conversion function other than the noise removal processing to output a pixel signal as a digital signal.

The horizontal driving unit 16 includes a shift register, an address decoder, and the like and sequentially selects unit circuits corresponding to the pixel columns of the column signal processing unit 15. By the selection and scanning performed by the horizontal driving unit 16, pixel signals processed by the column signal processing unit 15 are sequentially output to the signal processing unit 17.

The system control unit 12 includes a timing generator for generating various timing signals, and the like and performs driving control of the vertical driving unit 13, the column signal processing unit 15, the horizontal driving unit 16, and the like on the basis of various timing signals generated by the timing generator.

The solid-state imaging device 1 further includes the signal processing unit 17 and a data storage unit not illustrated in the drawing. The signal processing unit 17 has at least an addition processing function and performs various signal processing such as addition processing on the pixel signals output from the column signal processing unit 15.

The data storage unit temporarily stores data necessary for signal processing when the signal processing unit 17 performs the signal processing. The signal processing unit 17 and the data storage unit may perform processing by an external signal processing unit, for example, a digital signal processor (DSP) which is provided on a different substrate from the solid-state imaging device 1, or software, or may be mounted on the same substrate as the solid-state imaging device 1.

Configuration of Pixel Array Portion

Figure 2:
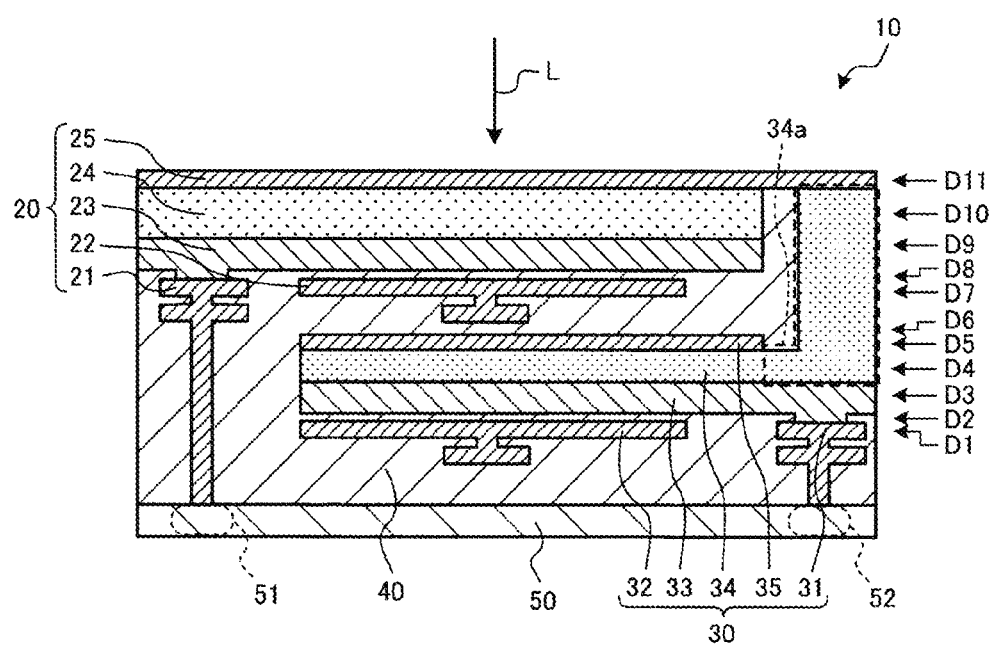
FIG. 2 is a cross-sectional view schematically illustrating a structure of a pixel array portion according to the embodiment of the present disclosure.

Next, a detailed configuration of the pixel array portion 10 will be described with reference to FIGS. 2, 3A, 3B, 3C, 3D, 3E, 3F, 3G, 3H, 3I, 3J, and 3K. FIG. 2 is a cross-sectional view schematically illustrating a structure of the pixel array portion 10 according to the embodiment of the present disclosure, and FIGS. 3A, 3B, 3C, 3D, 3E, 3F, 3G, 3H, 3I, 3J, and 3K are diagrams illustrating planar structures of depths D1 to D11 illustrated in FIG. 2.

As illustrated in FIG. 2, the pixel array portion 10 includes a photoelectric conversion portion 20, the photoelectric conversion portion 30, an insulating layer 40, and a semiconductor layer 50. The photoelectric conversion portion 30 is provided on a light incidence side (a side on which light L is incident from the outside) of the semiconductor layer 50, and the photoelectric conversion portion 20 is provided on a light incidence side of the photoelectric conversion portion 30.

In addition, one photoelectric conversion portion 20 and one photoelectric conversion portion 30 are provided for each unit pixel 11 (see FIG. 1). That is, a plurality of photoelectric conversion portions 20 and a plurality of photoelectric conversion portions 30 are provided in the entire pixel array portion 10.

The photoelectric conversion portion 20 includes a first electrode 21, a charge storage electrode 22, a charge storage layer 23, a photoelectric conversion layer 24, and a second electrode 25.

As illustrated in FIG. 2, the first electrode 21 is provided on a side opposite to the light incidence side in the photoelectric conversion portion 20. In addition, the first electrode 21 is in contact with a surface on a side opposite to the light incidence side of the charge storage layer 23 (hereinafter also referred to as a "bottom surface") on a surface on the light incidence side (hereinafter also referred to as a "top surface").

Further, the first electrode 21 extends in a depth direction inside the insulating layer 40 and is connected to a floating diffusion 51 provided in the semiconductor layer 50. That is, the first electrode 21 electrically connects the charge storage layer 23 and the floating diffusion 51 to each other.

The first electrode 21 is constituted by a conductor having light transmittance, that is, a so-called transparent conductor. The first electrode 21 is formed of, for example, indium tin oxide (ITO). Meanwhile, a constituent material of the first electrode 21 is not limited to ITO, and may be a tin oxide ($SnO_2$)-based material, a zinc oxide (ZnO)-based material, or the like.

Examples of such a zinc oxide-based material include aluminum zinc oxide (AZO), gallium zinc oxide (GZO), indium zinc oxide (IZO), and the like. In addition, for example, CuI, $InSbO_4$, ZnMgO, $CuInO_2$, $MgIn_2O_4$, CdO, $ZnSnO_3$, and the like may be used for the first electrode 21.

The charge storage electrode 22 is constituted by a transparent conductor, such as ITO, AZO, GZO, or IZO. Meanwhile, the constituent material of the charge storage electrode 22 is not limited to these transparent conductors, and may be a material similar to the various transparent conductors exemplified in description of the first electrode 21.

Figure 3A:
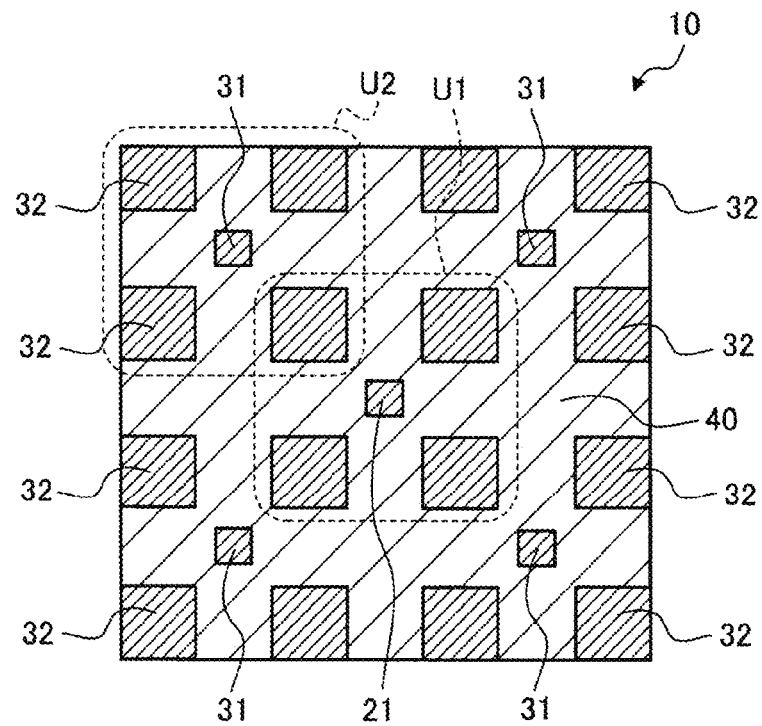
FIG. 3A is a diagram illustrating a planar structure of a depth D1 illustrated in FIG. 2.
Figure 3B:
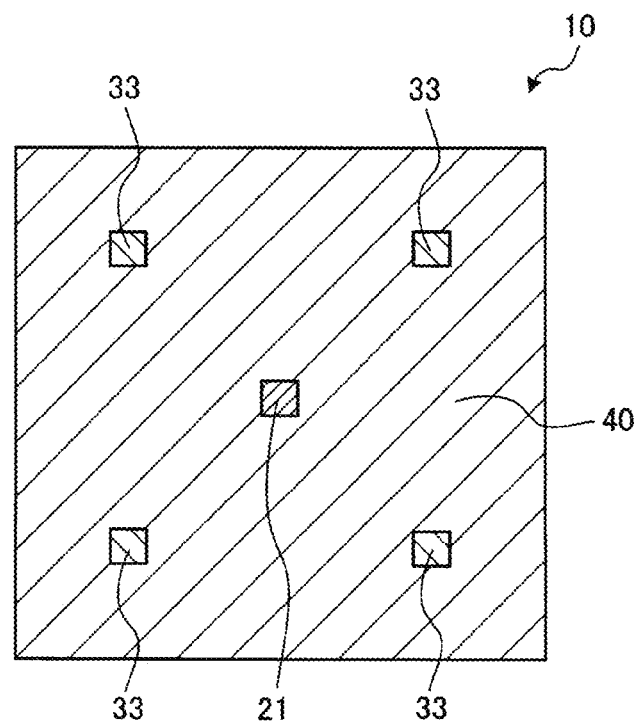
FIG. 3B is a diagram illustrating a planar structure of a depth D2 illustrated in FIG. 2.
Figure 3C:
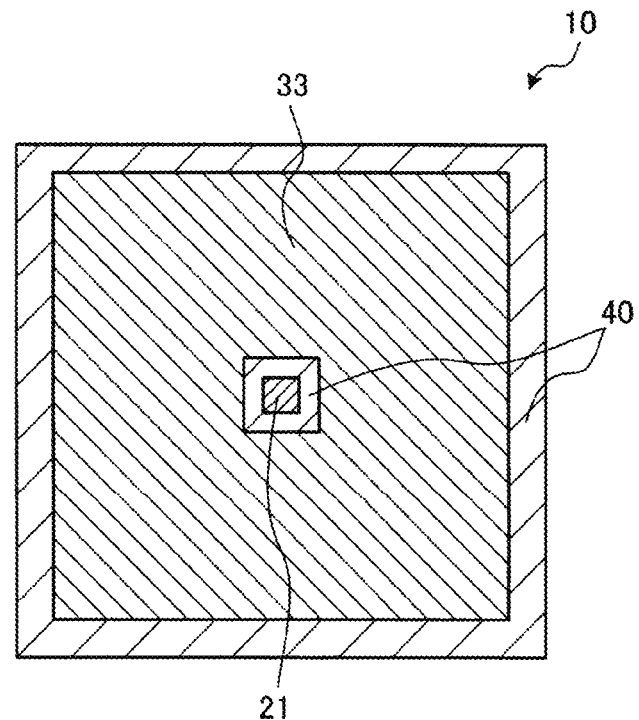
FIG. 3C is a diagram illustrating a planar structure of a depth D3 illustrated in FIG. 2.
Figure 3D:
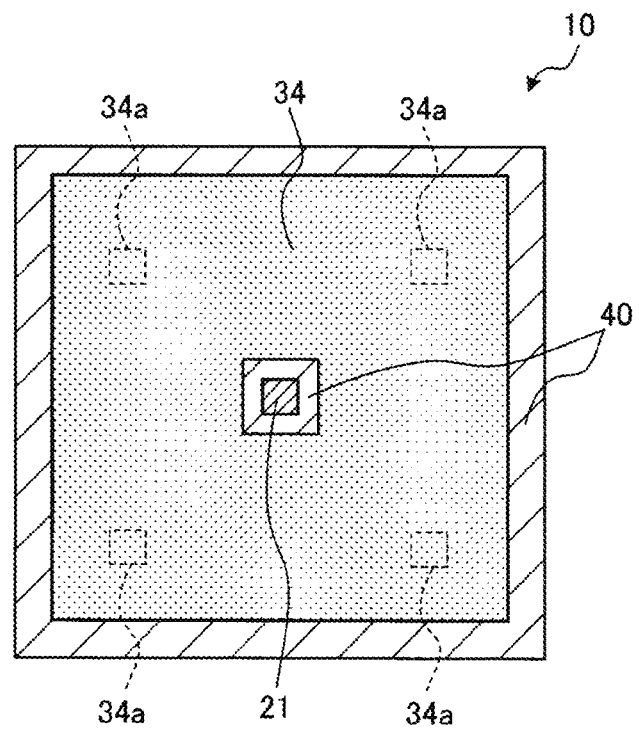
FIG. 3D is a diagram illustrating a planar structure of a depth D4 illustrated in FIG. 2.
Figure 3E:
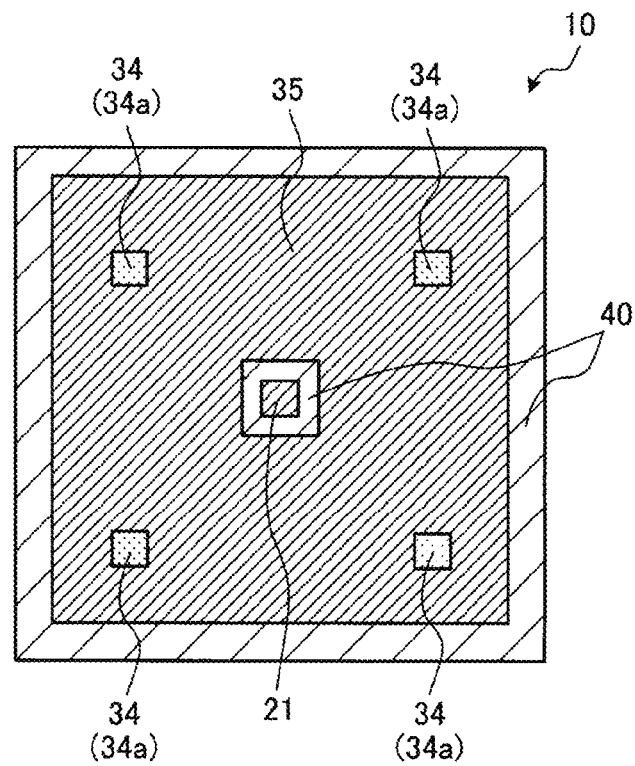
FIG. 3E is a diagram illustrating a planar structure of a depth D5 illustrated in FIG. 2.
Figure 3F:
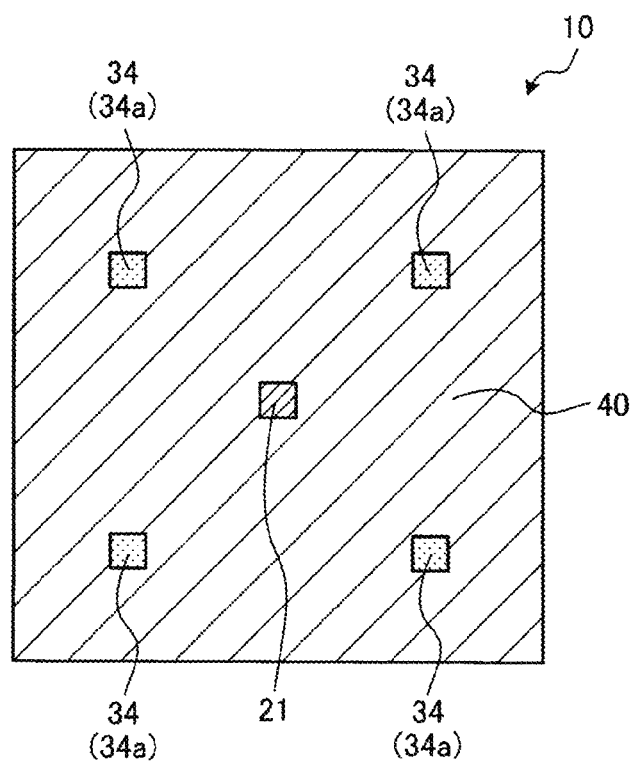
FIG. 3F is a diagram illustrating a planar structure of a depth D6 illustrated in FIG. 2.
Figure 3G:
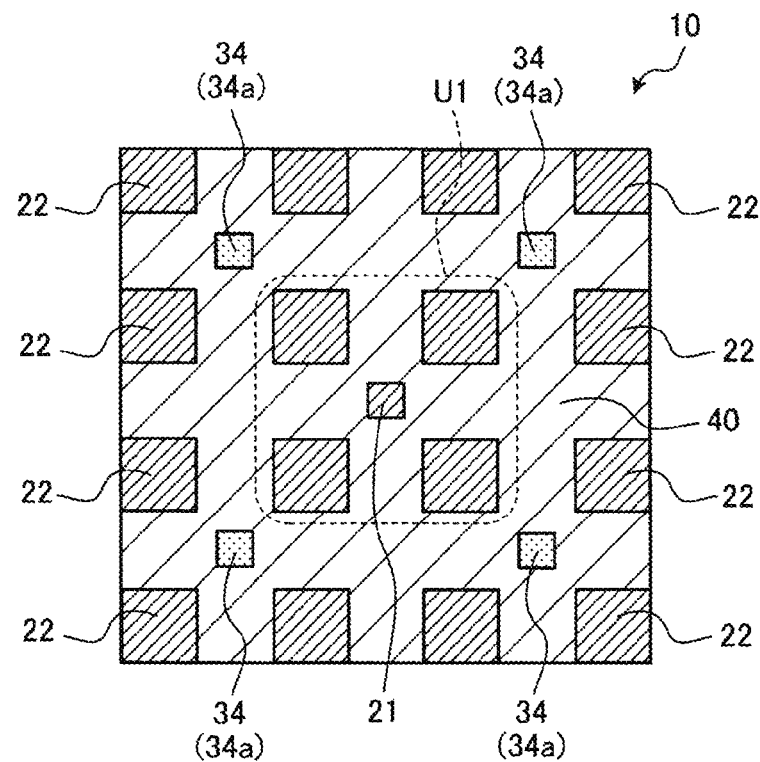
FIG. 3G is a diagram illustrating a planar structure of a depth D7 illustrated in FIG. 2.
Figure 3H:
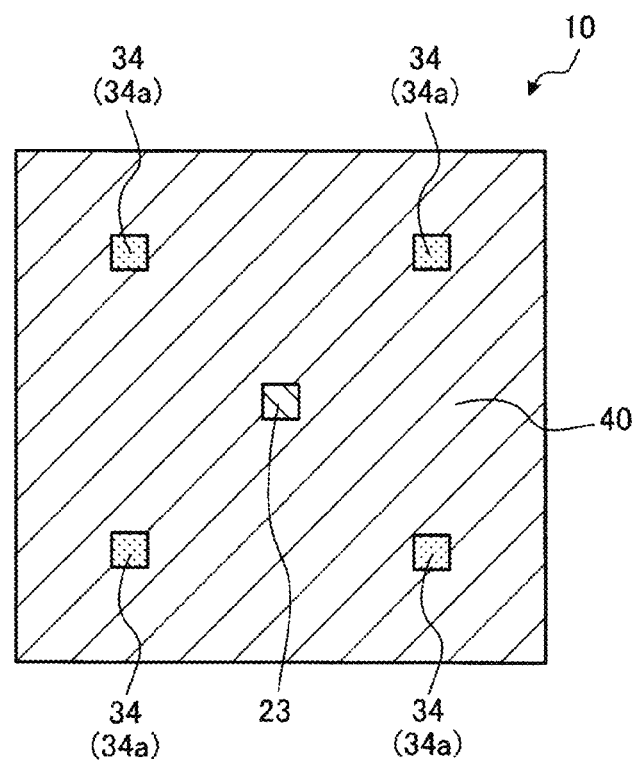
FIG. 3H is a diagram illustrating a planar structure of a depth D8 illustrated in FIG. 2.

As illustrated in FIGS. 2 and 3G, the charge storage electrode 22 is provided adjacent to the first electrode 21 through the insulating layer 40. Meanwhile, a unit U1 illustrated in FIG. 3G is one unit that shares the floating diffusion 51 in a plurality of (four in FIG. 3G) photoelectric conversion portions 20.

The charge storage layer 23 is formed of a semiconductor material having a large band gap, a high carrier mobility, and light transmittance. For the charge storage layer 23, it is preferable to use, for example, a material having a band gap of 3.0 (eV) or more, a carrier mobility higher than that of the material constituting the photoelectric conversion layer 24, and an impurity concentration of $1 \times 10^{18}$ ($cm^{-3}$) or less.

The charge storage layer 23 is constituted by, for example, an oxide semiconductor, an organic semiconductor, a two-dimensional semiconductor, or the like. For the oxide semiconductor, for example, a chalcogenide-based oxide semiconductor, indium gallium zinc oxide (IGZO), or the like can be used.

In addition, for the organic semiconductor, for example, rubrene, tetracene, pentacene, perylene diimide, tetracyanoquinodimethane, and the like, which are low molecular weight organic materials having an aromatic ring such as a condensed polycyclic hydrocarbon compound and a condensed heterocyclic compound, can be used.

In addition, for the organic semiconductor, polythiophene, polyacetylene, polyparaphenylene vinylene, and the like, which are n-electron conjugated conductive polymers, may be used. In addition, for the organic semiconductor, silicon carbide, diamond, graphene, carbon nanotubes, condensed polycyclic hydrocarbon compounds, condensed heterocyclic compounds, and the like may be used.

In addition, for the two-dimensional semiconductor, for example, molybdenum disulfide ($MoS_2$), tungsten disulfide ($WS_2$), hafnium disulfide ($HfS_2$), hexagonal boron nitride (hBN), indium selenium (InSe), a transition metal dichalcogenide, and the like can be used.

Further, in a case where charge to be stored is electrons, a material having an ionization potential larger than that of the material constituting the photoelectric conversion layer 24 is preferably used for the charge storage layer 23. On the other hand, in a case where charge to be stored is holes, a material having an electron affinity lower than that of the material constituting the photoelectric conversion layer 24 is preferably used for the charge storage layer 23.

Meanwhile, the charge storage tank 23 may have a single-layer configuration or a multi-layer configuration. In addition, the material constituting the charge storage layer 23 positioned above the charge storage electrode 22 and the material constituting the charge storage layer 23 positioned above the first electrode 21 may be different from each other.

As illustrated in FIGS. 2, 3G, 3H, 3I, and 3J, the top surface of the charge storage layer 23 is in contact with the bottom surface of the photoelectric conversion layer 24, and the bottom surface of the charge storage layer 23 is in contact with the top surface of the first electrode 21. In addition, the bottom surface of the charge storage layer 23 is adjacent to the charge storage electrode 22 through the insulating layer 40. In addition, when a predetermined voltage is applied to such a charge storage electrode 22, charge photoelectrically converted by the photoelectric conversion layer 24 is stored in the charge storage layer 23.

Figure 3I:
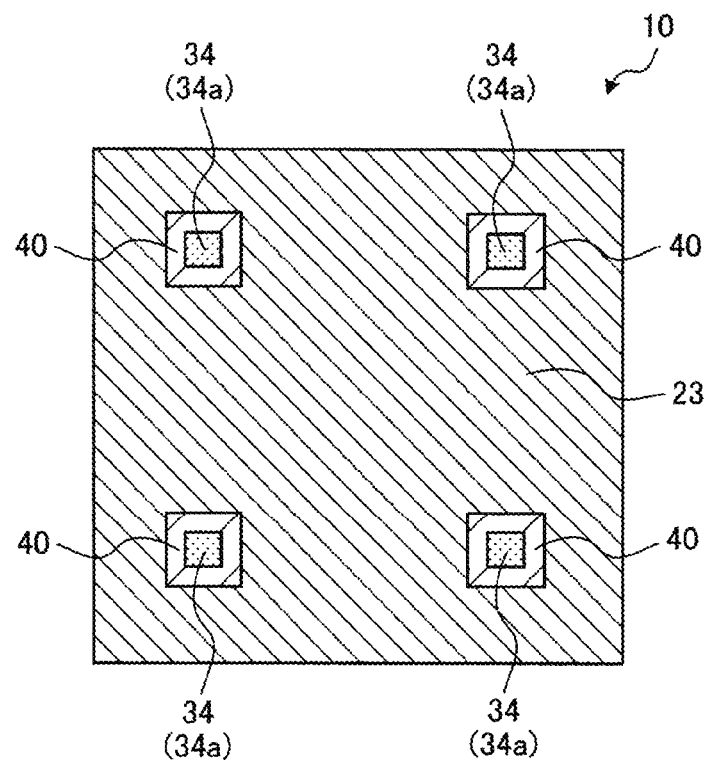
FIG. 3I is a diagram illustrating a planar structure of a depth D9 illustrated in FIG. 2.
Figure 3J:
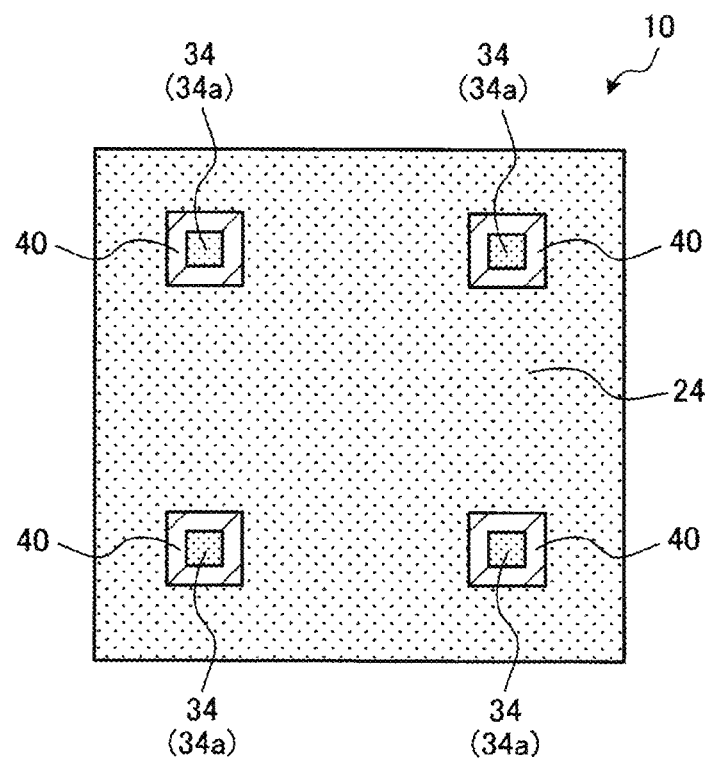
FIG. 3J is a diagram illustrating a planar structure of a depth D10 illustrated in FIG. 2.

As illustrated in FIGS. 2, 3I, and 3J, the photoelectric conversion layer 24 is provided to cover the top surface of the charge storage layer 23. The photoelectric conversion layer 24 is constituted by an organic semiconductor material and performs photoelectric conversion of light having a selective wavelength (for example, blue) in light L incident from the outside.

It is preferable that the photoelectric conversion layer 24 include one or both of a p-type organic semiconductor and an n-type organic semiconductor. The photoelectric conversion layer 24 is formed of, for example, quinacridone, quinacridone derivatives, subphthalocyanine, subphthalocyanine derivatives, or the like, and preferably contains at least one of these materials.

Meanwhile, the material of the photoelectric conversion layer 24 is not limited to such materials, and may be, for example, at least one of naphthalene, anthracene, phenanthrene, tetracene, pyrene, perylene, fluoranthene, and the like (including derivatives of any of them).

In addition, for the photoelectric conversion layer 24, polymers or derivatives such as phenylene vinylene, fluorene, carbazole, indole, pyrene, pyrrole, picolin, thiophene, acetylene, and diacetylene may be used.

In addition, for the photoelectric conversion layer 24, metal complex pigments, cyanine-based pigments, merocyanine-based pigments, phenylxanthene-based pigments, triphenylmethane-based pigments, rodacyanine-based pigments, xanthene-based pigments, and the like may be used. Meanwhile, examples of such metal complex pigments include dithiol metal complex-based pigments, metal phthalocyanine pigments, metal porphyrin pigments, ruthenium complex pigments, and the like. The photoelectric conversion layer 24 may contain other organic materials such as fullerenes ($C_{60}$) and BCP (bathocuproine), in addition to such organic semiconductor pigments.

In a case where photoelectric conversion of blue light is performed by the photoelectric conversion layer 24, for example, coumarin acid pigments, tris-8-hydroxyquinolialuminum (Alq3), merocyanine-based pigments, or the like can be used for the photoelectric conversion layer 24.

Figure 3K:
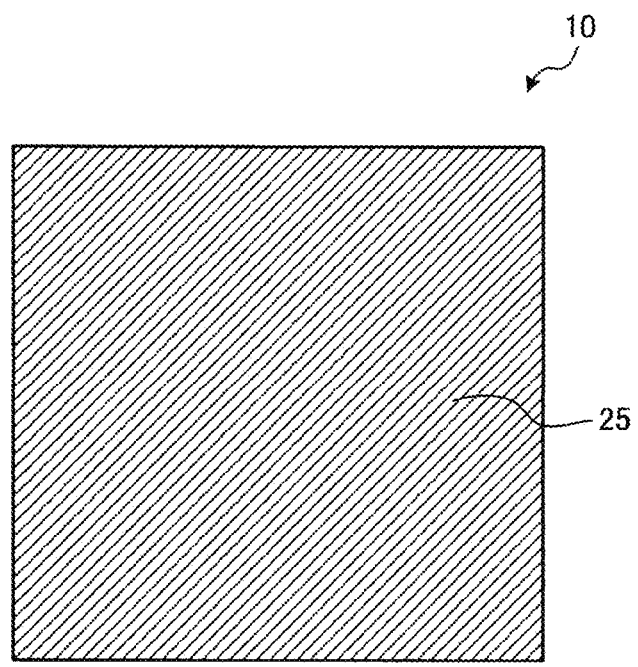
FIG. 3K is a diagram illustrating a planar structure of a depth D11 illustrated in FIG. 2.

As illustrated in FIGS. 2, 3J, and 3K, the second electrode 25 is provided to be in contact with the top surface of the photoelectric conversion layer 24 and cover the top surface. The second electrode 25 is constituted by a transparent conductor such as ITO, AZO, GZO, or IZO. Meanwhile, the constituent material of the second electrode 25 is not limited to these transparent conductors, and may be a material similar to the various transparent conductors exemplified in description of the first electrode 21.

The photoelectric conversion portion 30 is provided to be stacked on the photoelectric conversion portion 20 on the bottom surface side of the photoelectric conversion portion 20. The photoelectric conversion portion 30 includes a first electrode 31, a charge storage electrode 32, a charge storage layer 33, a photoelectric conversion layer 34, and a second electrode 35.

As illustrated in FIGS. 2, 3A, and 3B, the first electrode 31 is provided on a side opposite to a light incidence side in the photoelectric conversion portion 30. In addition, the top surface of the first electrode 31 is in contact with the bottom surface of the charge storage layer 33.

Further, the first electrode 31 extends in a depth direction inside the insulating layer 40 and is connected to a floating diffusion 52 provided in the semiconductor layer 50. That is, the first electrode 31 electrically connects the charge storage layer 33 and the floating diffusion 52.

The first electrode 31 is constituted by a transparent conductor such as ITO, AZO, GZO, or IZO. Meanwhile, the constituent material of the first electrode 31 is not limited to these transparent conductors, and may be a material similar to the various transparent conductors exemplified in description of the first electrode 21.

The charge storage electrode 32 is constituted by a transparent conductor such as ITO, AZO, GZO, or IZO. Meanwhile, the constituent material of the charge storage electrode 32 is not limited to these transparent conductors, and may be a material similar to the various transparent conductors exemplified in description of the first electrode 21.

As illustrated in FIGS. 2 and 3A, the charge storage electrode 32 is provided adjacent to the first electrode 31 through the insulating layer 40. Meanwhile, a unit U2 illustrated in FIG. 3A is one unit in which a plurality of (four in FIG. 3A) photoelectric conversion portions 30 share the floating diffusion 52.

The charge storage layer 33 is formed of a semiconductor material having a large band gap, a high carrier mobility, and light transmittance. Meanwhile, for the constituent material of the charge storage tank 33, materials similar to the various semiconductor materials exemplified in description of the charge storage layer 23 can be used.

As illustrated in FIGS. 2, 3A, 3B, 3C, and 3D, the top surface of the charge storage layer 33 is in contact with the bottom surface of the photoelectric conversion layer 34, and the bottom surface of the charge storage layer 33 is in contact with the top surface of the first electrode 31. In addition, the bottom surface of the charge storage layer 33 is adjacent to the charge storage electrode 32 through the insulating layer 40. In addition, when a predetermined voltage is applied to such a charge storage electrode 32, charge photoelectrically converted by the photoelectric conversion layer 34 is stored in the charge storage layer 33.

As illustrated in FIGS. 2, 3C, and 3D, the photoelectric conversion layer 34 is provided to cover the top surface of the charge storage layer 33. The photoelectric conversion layer 34 is constituted by an organic semiconductor material and performs photoelectric conversion of light having a selective wavelength (for example, green) in light L incident from the outside.

It is preferable that the photoelectric conversion layer 34 include one or both of a p-type organic semiconductor and an n-type organic semiconductor. Meanwhile, for such a p-type organic semiconductor and n-type organic semiconductor, materials similar to the various materials exemplified in description of the photoelectric conversion layer 24 can be used.

In a case where photoelectric conversion of green light is performed by the photoelectric conversion layer 34, for example, rhodamine-based pigments, merocyanine-based pigments, quinacridone derivatives, subphthalocyanine-based pigments (subphthalocyanine derivatives), and the like can be used for the photoelectric conversion layer 34.

As illustrated in FIGS. 2, 3D, and 3E, the second electrode 35 is provided in contact with the top surface of the photoelectric conversion layer 34. The second electrode 35 is constituted by a transparent conductor, such as ITO, AZO, GZO, or IZO. Meanwhile, the constituent material of the second electrode 35 is not limited to these transparent conductors, and may be a material similar to the various transparent conductors exemplified in description of the first electrode 21.

Here, in the embodiment, as illustrated in FIGS. 2, 3D, 3E, 3F, 3G, 3H, 3I, and 3J, the photoelectric conversion layer 34 of the photoelectric conversion portion 30 has a protrusion region 34a that protrudes from the second electrode 35 when seen in a plan view (that is, when seen from a side on which light L is incident).

Further, in the embodiment, such a protrusion region 34a is provided such that a surface on a light incidence side protrudes from a portion of the photoelectric conversion layer 34 which is in contact with the second electrode 35 (that is, a portion other than the protrusion region 34a in the photoelectric conversion layer 34).

Thereby, in the embodiment, such a portion corresponding to the protrusion region 34a can be used as an injection port into which a liquid solvent (for example, an organic solvent) can be injected in a coating step. That is, after a portion other than the photoelectric conversion layer 34 in the pixel array portion 10 is formed, a liquid raw material can be injected into a portion corresponding to the photoelectric conversion layer 34 through such an injection port.

Meanwhile, such a liquid raw material can be produced by dissolving the raw material of the photoelectric conversion layer 34 in an organic solvent, or the like.

Then, the photoelectric conversion layer 34 can be formed by drying the liquid raw material injected into the portion corresponding to the photoelectric conversion layer 34 at a predetermined temperature. In this manner, in the embodiment, a portion corresponding to the protrusion region 34a is used as an injection port into which a liquid raw material is injected, and thus the photoelectric conversion layer 34 can be formed after a semiconductor process is finished to a certain degree. A detailed manufacturing step for the pixel array portion 10 according to the embodiment will be described later.

Description of other portions in the pixel array portion 10 will be continued. The insulating layer 40 is provided on the top surface of the semiconductor layer 50 and is provided to surround the photoelectric conversion portion 20 and the photoelectric conversion portion 30. The insulating layer 40 is constituted by an insulator having light transmittance. The insulating layer 40 is formed of, for example, silicon oxide ($SiO_2$), silicon nitride (SiN), aluminum oxide ($Al_2O_3$), or the like.

The semiconductor layer 50 contains, for example, silicon. The semiconductor layer 50 includes a photodiode 60 (see FIG. 4) at a position overlapping the photoelectric conversion portion 20 and the photoelectric conversion portion 30 when seen in a plan view.

Such a photodiode 60 performs photoelectric conversion of light (for example, red) having a wavelength different from that of light photoelectrically converted by the photoelectric conversion portion 20 and the photoelectric conversion portion 30 in light L incident from the outside.

That is, one unit pixel 11 is provided with one photoelectric conversion portion 20, one photoelectric conversion portion 30, and one photodiode 60, and light of three colors is photoelectrically converted by the photoelectric conversion portion 20, the photoelectric conversion portion 30, and the photodiode 60.

In this manner, the photoelectric conversion portion 20, the photoelectric conversion portion 30, and the photodiode 60 are provided to be stacked in a direction in which light L is incident, and thus it is possible to acquire all color information of three colors by one unit pixel 11 without going through a color filter.

Thus, according to the embodiment, attenuation of incident light L by such a color filter can be suppressed, and thus it is possible to acquire a high-quality image.

Further, in the embodiment, the photoelectric conversion portion 20 in which the photoelectric conversion layer 24 is constituted by an organic semiconductor material and the photoelectric conversion portion 30 in which the photoelectric conversion layer 34 is similarly constituted by an organic semiconductor material are provided to be stacked on each other in one unit pixel 11.

Thereby, in one unit pixel 11, light of a color which is not photoelectrically converted can be efficiently made to pass through the photoelectric conversion portion 30 and the photodiode 60 on the inner side. That is, according to the embodiment, attenuation of light L can be suppressed by the photoelectric conversion portion 20 and the photoelectric conversion portion 30, and thus it is possible to acquire a higher quality image.

In addition, the semiconductor layer 50 is provided with a floating diffusion 51 corresponding to the photoelectric conversion portion 20 and a floating diffusion 52 corresponding to the photoelectric conversion portion 30.

Meanwhile, the semiconductor layer 50 is provided with a plurality of pixel transistors performing reading of charge stored in the photoelectric conversion portions 20 and 30 and the photodiode 60, and a multi wiring layer including a plurality of wiring layers and an interlayer insulating film, none of which is illustrated in FIGS. 2, 3A, 3B, 3C, 3D, 3E, 3F, 3G, 3H, 3I, 3J, and 3K.

In addition, an on-chip lens for condensing light L and the like are provided on the light incidence side of the photoelectric conversion portion 20, but such an on-chip lens and the like are not illustrated in the drawings.

Example of Circuit Configuration of Unit Pixel

Figure 4:
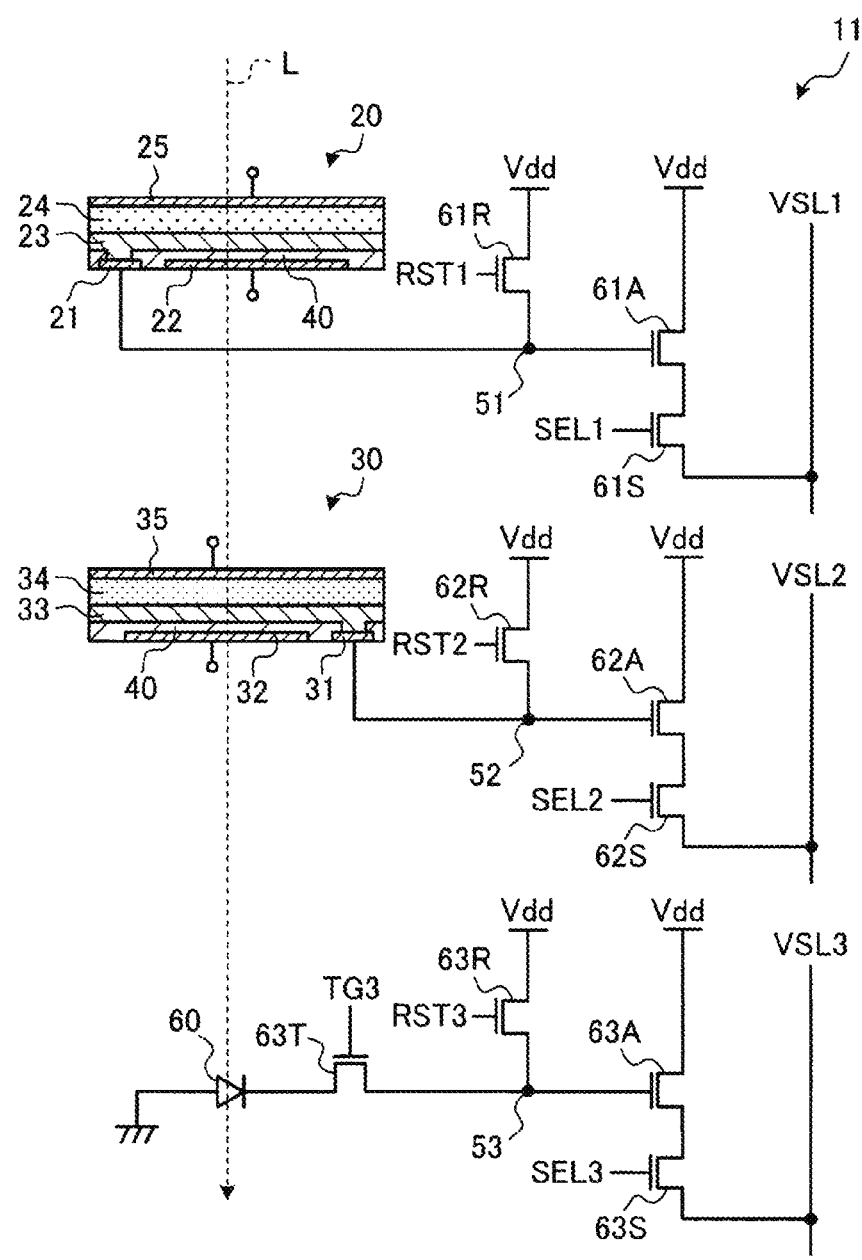
FIG. 4 is a circuit diagram illustrating a circuit configuration of a unit pixel according to the embodiment of the present disclosure.

Subsequently, an example of a circuit configuration of the unit pixel 11 will be described with reference to FIG. 4. FIG. 4 is a circuit diagram illustrating an example of a circuit configuration of the unit pixel 11 according to the embodiment of the present disclosure.

The unit pixel 11 includes the floating diffusion 51, a reset transistor 61R, an amplification transistor 61A, and a selection transistor 61S as circuits that perform reading of charge from the photoelectric conversion portion 20, and the like.

In the photoelectric conversion portion 20, a predetermined voltage is applied to the first electrode 21, the charge storage electrode 22, and the second electrode 25 from a driving circuit not illustrated in the drawing in a charge storage period. For example, in a charge storage period, a positive voltage is applied to the first electrode 21 and the charge storage electrode 22, and a negative voltage is applied to the second electrode 25. Further, in a charge storage period, a positive voltage higher than that applied to the first electrode 21 is applied to the charge storage electrode 22.

Thereby, in a charge storage period, electrons included in charge generated through photoelectric conversion in the photoelectric conversion layer 24 are attracted by a high positive voltage of the charge storage electrode 22 and are stored in the charge storage layer 23.

Further, in the unit pixel 11, a reset operation is performed by operating the reset transistor 61R in the latter half of the charge storage period. Thereby, the potential of the floating diffusion 51 is reset, and the potential of the floating diffusion 51 becomes a power voltage Vdd.

In the unit pixel 11, a charge transfer operation is performed after such a reset operation is completed. In such a charge transfer operation, a positive voltage higher than that applied to the charge storage electrode 22 is applied to the first electrode 21 from the driving circuit. Thereby, electrons stored in the charge storage layer 23 are transferred to the floating diffusion 51 through the first electrode 21.

In the unit pixel 11, a series of operations such as a charge storage operation, a reset operation, and a charge transfer operation are completed by the above-described operations.

The floating diffusion 51 holds charge read from the photoelectric conversion portion 20. The reset transistor 61R resets the potential of the floating diffusion 51 by discharging charge stored in the floating diffusion 51 to a drain (power voltage Vdd) when the reset transistor 61R is turned on in response to a reset signal RST1.

The amplification transistor 61A outputs a pixel signal indicating a level corresponding to charge stored in the floating diffusion 51 to a signal line VSL1 through the selection transistor 61S. The selection transistor 61S is turned on when the unit pixel 11 is selected in response to a selection signal SEL1, and outputs a pixel signal generated by the photoelectric conversion portion 20 to the vertical signal line VSL1.

In addition, the unit pixel 11 includes the floating diffusion 52, a reset transistor 62R, an amplification transistor 62A, and a selection transistor 62S as circuits that perform reading of charge from the photoelectric conversion portion 30, and the like.

Configurations and operations of the circuits that perform reading of charge from the photoelectric conversion portion 30, and the like are similar to those of the circuits that perform reading of charge from the photoelectric conversion portion 20 mentioned above, and the like and thus detailed description thereof will be omitted.

In addition, the unit pixel 11 includes a transfer transistor 63T, a floating diffusion 53, a reset transistor 63R, an amplification transistor 63A, and a selection transistor 63S as circuits that perform reading of charge from the photodiode 60, and the like.

The photodiode 60 generates and stores charge corresponding to the amount of received light. In the photodiode 60, an anode terminal is grounded, and a cathode terminal is connected to the floating diffusion 53 through the transfer transistor 63T.

The transfer transistor 63T reads charge generated by the photodiode 60 and transfers the generated charge to the floating diffusion 53 when the transfer transistor 63T is turned on in response to a transfer signal TG3.

The floating diffusion 53 holds charge read from the photodiode 60. The reset transistor 63R resets the potential of the floating diffusion 53 by discharging charge stored in the floating diffusion 53 to a drain (power voltage Vdd) when the reset transistor 63R is turned on in response to a reset signal RST3.

The amplification transistor 63A outputs a pixel signal indicating a level corresponding to charge stored in the floating diffusion 53 to a signal line VSL3 through the selection transistor 63S. The selection transistor 63S is turned on when the unit pixel 11 is selected in response to a selection signal SEL3, and outputs a pixel signal generated by the photodiode 60 to a vertical signal line VSL3.

In the pixel array portion 10 according to the embodiment, the charge storage electrode 22 and the charge storage layer 23 are provided in the photoelectric conversion portion 20, and thus it is possible to reduce reset noise during a reset operation performed by the reset transistor 61R. Thus, according to the embodiment, it is possible to acquire a high-quality image.

Further, in the pixel array portion 10 according to the embodiment, the charge storage electrode 32 and the charge storage layer 33 are provided in the photoelectric conversion portion 30, and thus it is possible to reduce reset noise during a reset operation performed by the reset transistor 62R. Thus, according to the embodiment, it is possible to acquire a high-quality image.

Further, in the pixel array portion 10 according to the embodiment, as described above, a plurality of photoelectric conversion portions 20 included in the unit U1 (see FIG. 3G) share the floating diffusion 51. Thereby, it is not necessary to provide individual floating diffusions 51 in all of the photoelectric conversion portions 20, and thus it is possible to simplify a circuit configuration inside the pixel array portion 10.

Thus, according to the embodiment, it is possible to reduce manufacturing costs of the pixel array portion 10.

Similarly, in the pixel array portion 10 according to the embodiment, a plurality of photoelectric conversion portions 30 included in the unit U2 (see FIG. 3A) share the floating diffusion 52. Thereby, it is not necessary to provide individual floating diffusions 52 in all of the photoelectric conversion portions 30, and thus it is possible to simplify a circuit configuration inside the pixel array portion 10.

Thus, according to the embodiment, it is possible to reduce manufacturing costs of the pixel array portion 10.

Meanwhile, in the pixel array portion 10 according to the embodiment, a plurality of photodiodes 60 may share the floating diffusion 53. Thereby, it is not necessary to provide individual floating diffusions 53 in all of the photodiodes 60, and thus it is possible to simplify a circuit configuration inside the pixel array portion 10.

Thus, according to the embodiment, it is possible to reduce manufacturing costs of the pixel array portion 10.

A circuit in the unit pixel 11 can be configured as described above, but is not limited to this configuration, and other configurations can be adopted.

Figure 5:
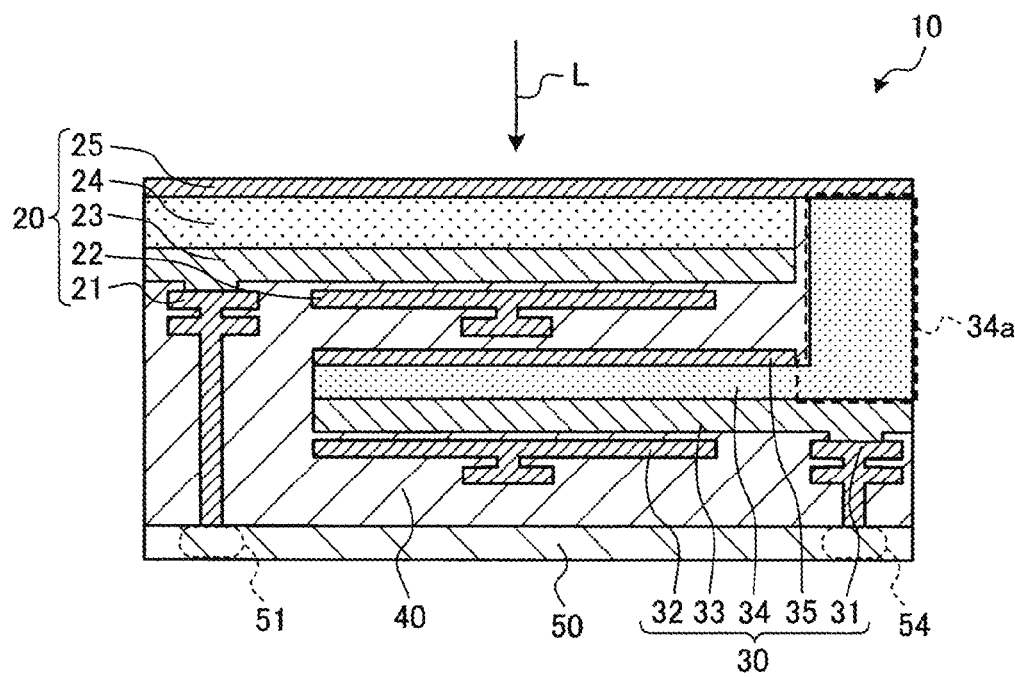
FIG. 5 is a cross-sectional view schematically illustrating a structure of a pixel array portion according to another embodiment of the present disclosure.

For example, as illustrated in FIG. 5, the protrusion region 34a of the photoelectric conversion layer 34 is used as a light-shielding layer, and thus it is possible to hold charge photoelectrically converted in the charge holding region 54 of the semiconductor layer 50 provided below the protrusion region 34a. FIG. 5 is a cross-sectional view schematically illustrating a structure of the pixel array portion 10 according to another embodiment of the present disclosure.

Further, in the example of FIG. 5, photoelectrically converted charge is transferred to the charge holding region 54 at the same time in all pixels, and thus a global shutter function can be given to the photoelectric conversion portion 30 of the pixel array portion 10.

Figure 6:
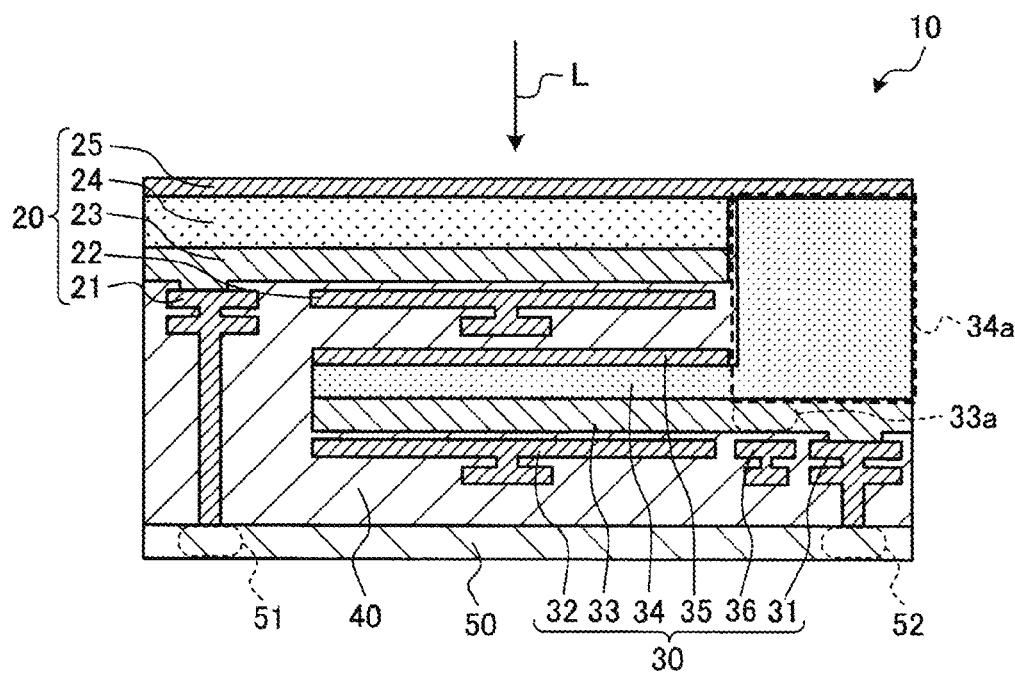
FIG. 6 is a cross-sectional view schematically illustrating a structure of a pixel array portion according to still another embodiment of the present disclosure.

In addition, as illustrated in FIG. 6, the protrusion region 34a of the photoelectric conversion layer 34 is used as a light-shielding layer, and a charge holding electrode 36 is provided below the protrusion region 34a, whereby it is possible to hold photoelectrically converted charge in a charge holding region 33a of the charge storage layer 33 provided below the protrusion region 34a. FIG. 6 is a cross-sectional view schematically illustrating a structure of the pixel array portion 10 according to still another embodiment of the present disclosure.

Further, in the example of FIG. 6, photoelectrically converted charge is transferred to the charge holding region 33a at the same time in all pixels, and thus a global shutter function can be added to the photoelectric conversion portion 30 of the pixel array portion 10.

Meanwhile, a voltage is not applied to the protrusion region 34a in the second electrode 25 and the like, and thus photoelectrically converted charge remains in the protrusion region 34a as it is. Thus, in the embodiment, such a protrusion region 34a can be used as a substantial light-shielding layer.

In addition, as illustrated in FIGS. 5 and 6, the protrusion region 34a is provided to protrude toward a light incidence side from a portion of the photoelectric conversion layer 34 which is in contact with the second electrode 35 and is provided to reach the second electrode 25, such a protrusion region 34a has a high light-shielding performance. Thus, the protrusion region 34a is provided to protrude toward a light incidence side, and thus it is possible to give a highly accurate global shutter function.

Figure 7:
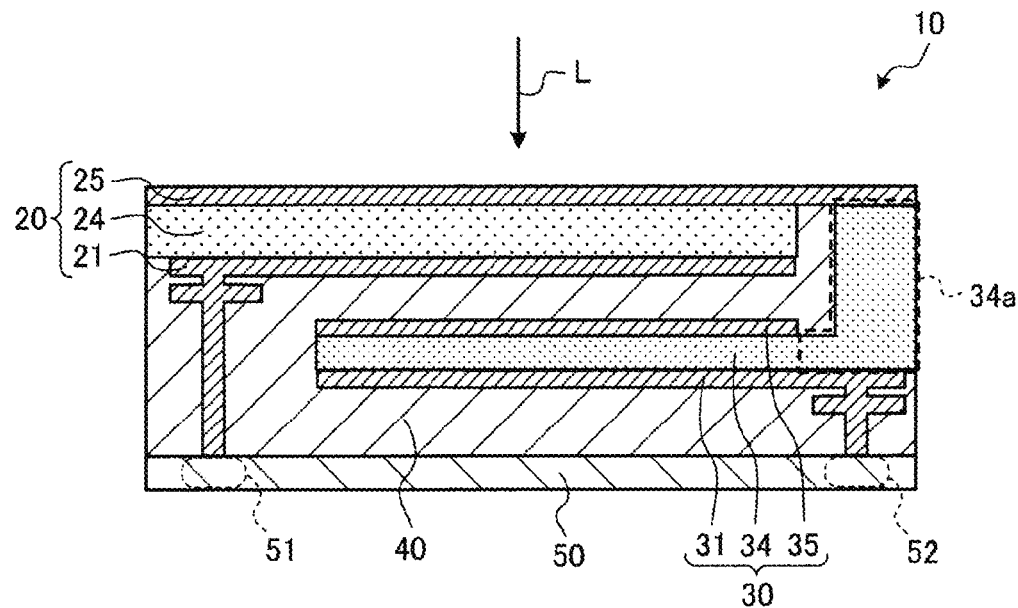
FIG. 7 is a cross-sectional view schematically illustrating a structure of a pixel array portion according to still another embodiment of the present disclosure.

In addition, as illustrated in FIG. 7, the unit pixel 11 may be configured such that the charge storage electrode 22 and the charge storage layer 23 are excluded from the photoelectric conversion portion 20, and the charge storage electrode 32 and the charge storage layer 33 are excluded from the photoelectric conversion portion 30. FIG. 7 is a cross-sectional view schematically illustrating a structure of the pixel array portion 10 according to still another embodiment of the present disclosure.

That is, in the example of FIG. 7, the photoelectric conversion portion 20 includes the first electrode 21, the photoelectric conversion layer 24, and the second electrode 25, and the photoelectric conversion portion 30 includes the first electrode 31, the photoelectric conversion layer 34, and the second electrode 35.

Further, in the example of FIG. 7, after a reset operation is performed by a reset transistor not illustrated in the drawing, a positive voltage is applied to the first electrode 21 (or the first electrode 31), and a negative voltage is applied to the second electrode 25 (or the second electrode 35).

Thereby, electrons included in charge generated through photoelectric conversion in the photoelectric conversion layer 24 (or the photoelectric conversion layer 34) are moved to the first electrode 21 (or the first electrode 31). Then, the electrons moved to the first electrode 21 (or the first electrode 31) are transferred to the floating diffusion 51 (or the floating diffusion 52).

In such an example of FIG. 7, the charge storage electrodes 22 and 32 and the charge storage layers 23 and 33 do not need to be formed, and thus it is possible to reduce manufacturing costs of the pixel array portion 10.

Various Modification Examples

Figure 8:
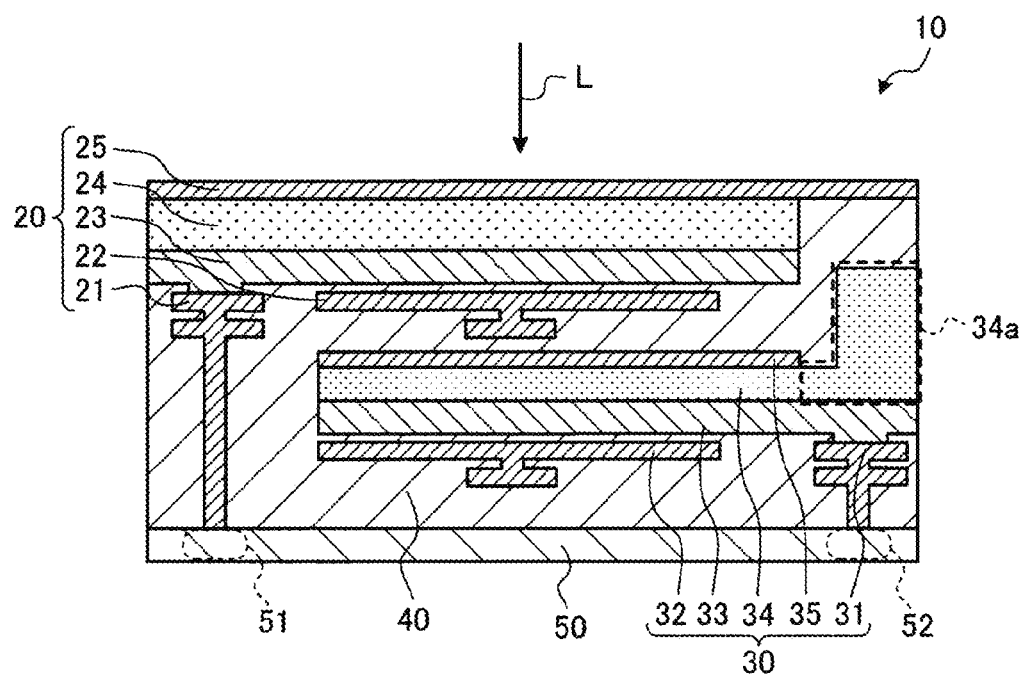
FIG. 8 is a cross-sectional view schematically illustrating a structure of a pixel array portion according to Modification Example 1 of the embodiment of the present disclosure.

Next, various modification examples of the embodiment will be described with reference to FIGS. 8 to 13. FIG. 8 is a cross-sectional view schematically illustrating a structure of the pixel array portion 10 according to Modification Example 1 of the embodiment of the present disclosure.

In Modification Example 1, a configuration of the protrusion region 34a in the photoelectric conversion layer 34 is different from that in the embodiment. Specifically, the protrusion region 34a in Modification Example 1 is provided such that a surface on a light incidence side protrudes toward the light incidence side from a portion of the photoelectric conversion layer 34 which is in contact with the second electrode 35, but does not reach the second electrode 25.

Also in such Modification Example 1, similarly to the embodiment, a portion corresponding to the protrusion region 34a can be used as an injection port into which a liquid raw material can be injected. That is, after a portion other than the photoelectric conversion layer 34 in the pixel array portion 10 is formed, a liquid raw material can be injected into a portion corresponding to the photoelectric conversion layer 34 through such an injection port.

Then, the photoelectric conversion layer 34 can be formed by drying the liquid raw material injected into the portion corresponding to the photoelectric conversion layer 34 at a predetermined temperature. Thus, according to Modification Example 1, the photoelectric conversion layer 34 can be formed after a semiconductor process is finished to a certain degree. A detailed manufacturing step for the pixel array portion 10 according to Modification Example 1 will be described later.

Figure 9:
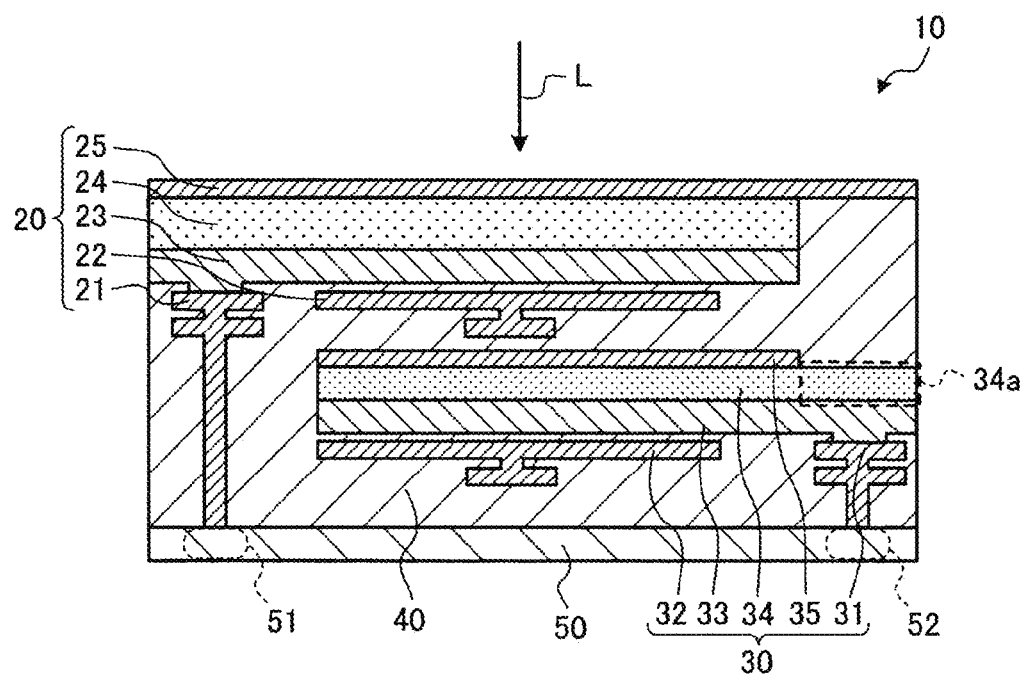
FIG. 9 is a cross-sectional view schematically illustrating a structure of a pixel array portion according to Modification Example 2 of the embodiment of the present disclosure.

FIG. 9 is a cross-sectional view schematically illustrating a structure of the pixel array portion 10 according to Modification Example 2 of the embodiment of the present disclosure.

In Modification Example 2, a configuration of the protrusion region 34a in the photoelectric conversion layer 34 is different from those in the embodiment and Modification Example 1. Specifically, in the protrusion region 34a in Modification Example 2, a portion of the photoelectric conversion layer 34 which is in contact with the second electrode 35 and a surface on the light incidence side are substantially flush with each other.

Also in such Modification Example 2, similarly to the embodiment, a portion corresponding to the protrusion region 34a can be used as an injection port into which a liquid raw material can be injected. That is, after a portion other than the photoelectric conversion layer 34 in the pixel array portion 10 is formed, a liquid raw material can be injected into a portion corresponding to the photoelectric conversion layer 34 through such an injection port.

Then, the photoelectric conversion layer 34 can be formed by drying the liquid raw material injected into the portion corresponding to the photoelectric conversion layer 34 at a predetermined temperature. Thus, according to Modification Example 2, the photoelectric conversion layer 34 can be formed after a semiconductor process is finished to a certain degree. Meanwhile, a detailed manufacturing step for the pixel array portion 10 according to Modification Example 2 will be described later.

Figure 10:
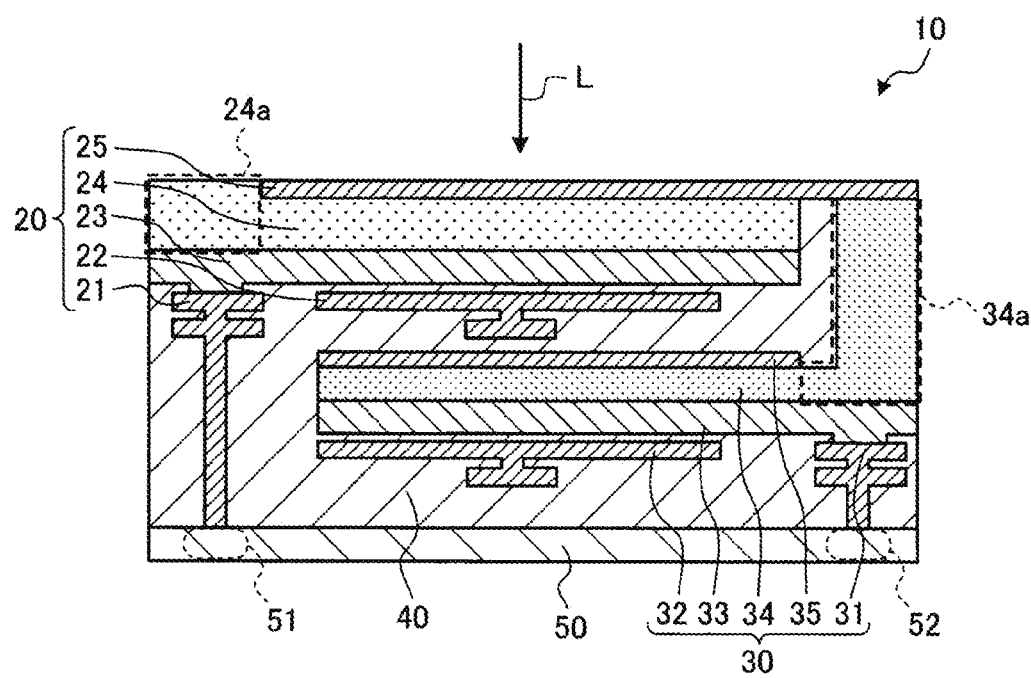
FIG. 10 is a cross-sectional view schematically illustrating a structure of a pixel array portion according to Modification Example 3 of the embodiment of the present disclosure.

FIG. 10 is a cross-sectional view schematically illustrating a structure of the pixel array portion 10 according to Modification Example 3 of the embodiment of the present disclosure.

In Modification Example 3, a configuration of the photoelectric conversion layer 24 in the photoelectric conversion portion 20 is different from that in the embodiment. Specifically, the photoelectric conversion layer 24 in Modification Example 3 includes a protrusion region 24a that protrudes from the second electrode 25 when seen in a plan view, similar to the photoelectric conversion layer 34.

Further, in Modification Example 3, such a protrusion region 24a is provided such that a surface on a light incidence side protrudes toward the light incidence side from a portion of the photoelectric conversion layer 24 which is in contact with the second electrode 25 (that is, a portion other than the protrusion region 24a in the photoelectric conversion layer 24).

In such Modification Example 3, a portion corresponding to the protrusion region 24a can be used as an injection port into which a liquid raw material can be injected. That is, after a portion other than the photoelectric conversion layer 24 in the pixel array portion 10 is formed, a liquid raw material can be injected into a portion corresponding to the photoelectric conversion layer 24 through such an injection port.

Then, the photoelectric conversion layer 24 can be formed by drying the liquid raw material injected into the portion corresponding to the photoelectric conversion layer 24 at a predetermined temperature. Thus, according to Modification Example 3, after a semiconductor process is finished to a certain degree, the photoelectric conversion layer 24 of the photoelectric conversion portion 20 can also be formed, in addition to the photoelectric conversion layer 34 of the photoelectric conversion portion 30. A detailed manufacturing step for the pixel array portion 10 according to Modification Example 3 will be described later.

Figure 11:
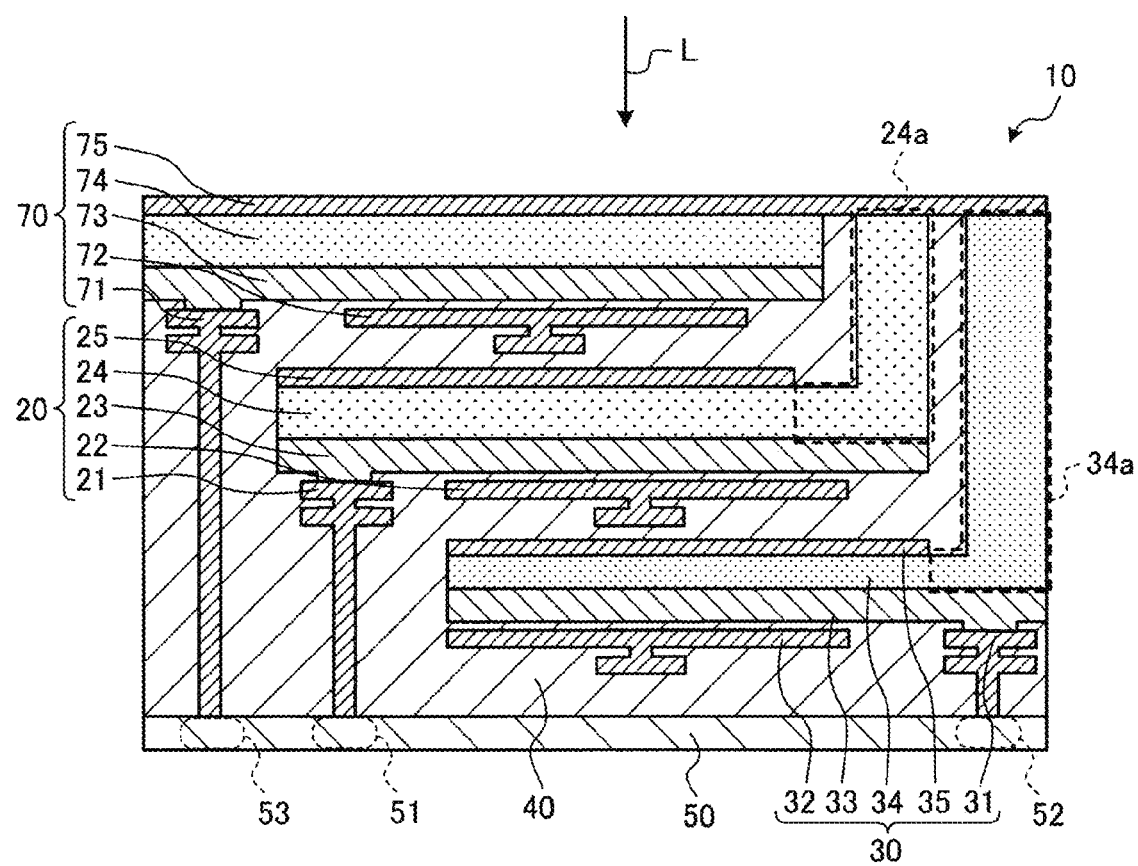
FIG. 11 is a cross-sectional view schematically illustrating a structure of a pixel array portion according to Modification Example 4 of the embodiment of the present disclosure.

FIG. 11 is a cross-sectional view schematically illustrating a structure of the pixel array portion 10 according to Modification Example 4 of the embodiment of the present disclosure.

As illustrated in FIG. 11, in the pixel array portion 10 according to Modification Example 4, the protrusion region 24a is provided in the photoelectric conversion layer 24 of the photoelectric conversion portion 20, and the protrusion region 34a is provided in the photoelectric conversion layer 34 of the photoelectric conversion portion 30.

Further, in Modification Example 4, another photoelectric conversion portion 70 is provided on a light incidence side of the photoelectric conversion portion 20. Such a photoelectric conversion portion 70 is provided to be stacked on the photoelectric conversion portion 20 on the top surface side of the photoelectric conversion portion 20. The photoelectric conversion portion 70 includes a first electrode 71, a charge storage electrode 72, a charge storage layer 73, a photoelectric conversion layer 74, and a second electrode 75.

As illustrated in FIG. 11, the first electrode 71 is provided on a side opposite to a light incidence side in the photoelectric conversion portion 70. In addition, the first electrode 71 is in contact with the bottom surface of the charge storage layer 73 on the top surface thereof.

Further, the first electrode 71 extends in a depth direction inside the insulating layer 40 and is connected to the floating diffusion 53 provided in the semiconductor layer 50. That is, the first electrode 71 electrically connects the charge storage layer 73 and the floating diffusion 53 to each other.

The first electrode 71 is constituted by a transparent conductor such as ITO, AZO, GZO, or IZO. Meanwhile, the constituent material of the first electrode 71 is not limited to these transparent conductors, and may be materials similar to those of various transparent conductors exemplified in description of the first electrode 21.

The charge storage electrode 72 is constituted by a transparent conductor such as ITO, AZO, GZO, or IZO. Meanwhile, the constituent material of the charge storage electrode 72 is not limited to these transparent conductors, and may be materials similar to those of various transparent conductors exemplified in description of the first electrode 21. The charge storage electrode 72 is provided to be adjacent to the first electrode 71 through the insulating layer 40.

The charge storage layer 73 is formed of a semiconductor material having a large band gap, a high carrier mobility, and light transmittance. Meanwhile, for the constituent material of the charge storage tank 73, materials similar to various semiconductor materials exemplified in description of the charge storage layer 23 can be used.

The top surface of the charge storage layer 73 is in contact with the bottom surface of the photoelectric conversion layer 74, and the bottom surface of the charge storage layer 73 is in contact with the top surface of the first electrode 71. In addition, the bottom surface of the charge storage layer 73 is adjacent to the charge storage electrode 72 through the insulating layer 40. In addition, when a predetermined voltage is applied to such a charge storage electrode 72, charge photoelectrically converted by the photoelectric conversion layer 74 is stored in the charge storage layer 73.

The photoelectric conversion layer 74 is provided to cover the top surface of the charge storage layer 73. The photoelectric conversion layer 74 is constituted by an organic semiconductor material and performs photoelectric conversion of light having a selective wavelength (for example, red) in light L incident from the outside.

It is preferable that the photoelectric conversion layer 74 include one or both of a p-type organic semiconductor and an n-type organic semiconductor. Meanwhile, for such a p-type organic semiconductor and n-type organic semiconductor, materials similar to various materials exemplified in description of the photoelectric conversion layer 24 can be used.

In a case where photoelectric conversion of red light is performed by the photoelectric conversion layer 74, for example, phthalocyanine-based pigments, subphthalocyanine-based pigments (subphthalocyanine derivatives), and the like can be used for the photoelectric conversion layer 74.

The second electrode 75 is provided to be in contact with the top surface of the photoelectric conversion layer 74. The second electrode 75 is constituted by a transparent conductor such as ITO, AZO, GZO, or IZO. Meanwhile, the constituent material of the second electrode 75 is not limited to these transparent conductors, and may be a material similar to those of various transparent conductors exemplified in description of the first electrode 21.

In this manner, in Modification Example 4, the photoelectric conversion portion 70 in which the photoelectric conversion layer 74 is constituted by an organic semiconductor material is provided to be further stacked on the photoelectric conversion portion 20 and the photoelectric conversion portion 30 in one unit pixel 11.

Thereby, in one unit pixel 11, light of a color which is not photoelectrically converted can be more efficiently made to pass through the photoelectric conversion portion 20 and the photoelectric conversion portion 30 on the inner side. That is, according to Modification Example 4, attenuation of light L can be suppressed by the photoelectric conversion portion 70 and the photoelectric conversion portion 20, and thus it is possible to acquire a higher quality image. A detailed manufacturing step for the pixel array portion 10 according to Modification Example 4 will be described later.

Figure 12:
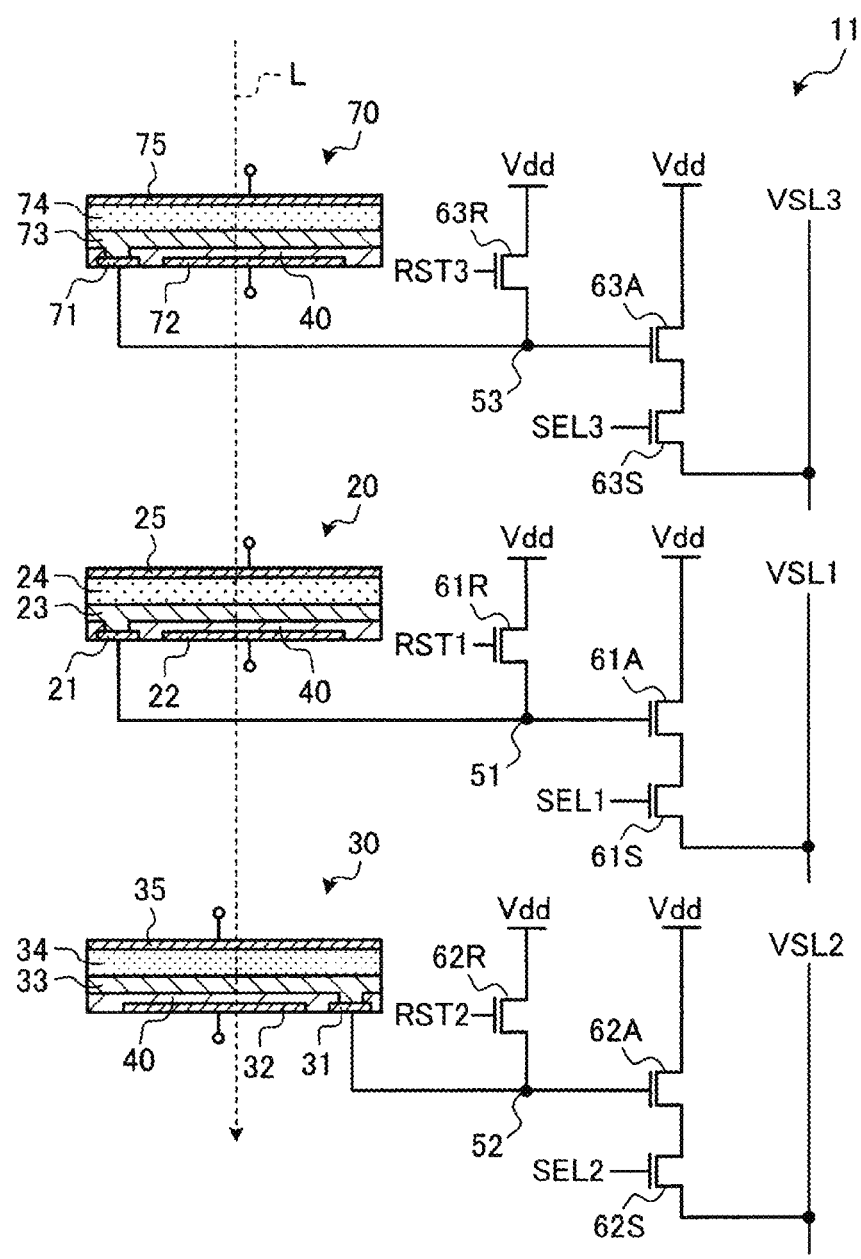
FIG. 12 is a circuit diagram illustrating a circuit configuration of a unit pixel according to Modification Example 4 of the embodiment of the present disclosure.

FIG. 12 is a circuit diagram illustrating a circuit configuration of the unit pixel 11 according to Modification Example 4 of the embodiment of the present disclosure. The unit pixel 11 includes the floating diffusion 53, the reset transistor 63R, the amplification transistor 63A, and the selection transistor 63S as circuits that perform reading of charge from the photoelectric conversion portion 70.

Operations of a circuit that performs reading of charge from the photoelectric conversion portion 70, and the like are similar to those of the above-described circuit that performs reading of charge from the photoelectric conversion portion 20, and the like, and thus detailed description thereof will be omitted. In addition, a configuration and operations of the circuit that performs reading of charge from the photoelectric conversion portion 20 and the photoelectric conversion portion 30, and the like are also similar to those in the above-described embodiment, and thus detailed description thereof will be omitted.

In the pixel array portion 10 according to Modification Example 4, a plurality of photoelectric conversion portions 70 may share the floating diffusion 53. Thereby, it is not necessary to provide individual floating diffusions 53 in all of the photoelectric conversion portions 70, and thus it is possible to simplify a circuit configuration inside the pixel array portion 10.

Thus, according to Modification Example 4, it is possible to reduce manufacturing costs of the pixel array portion 10.

Figure 13:
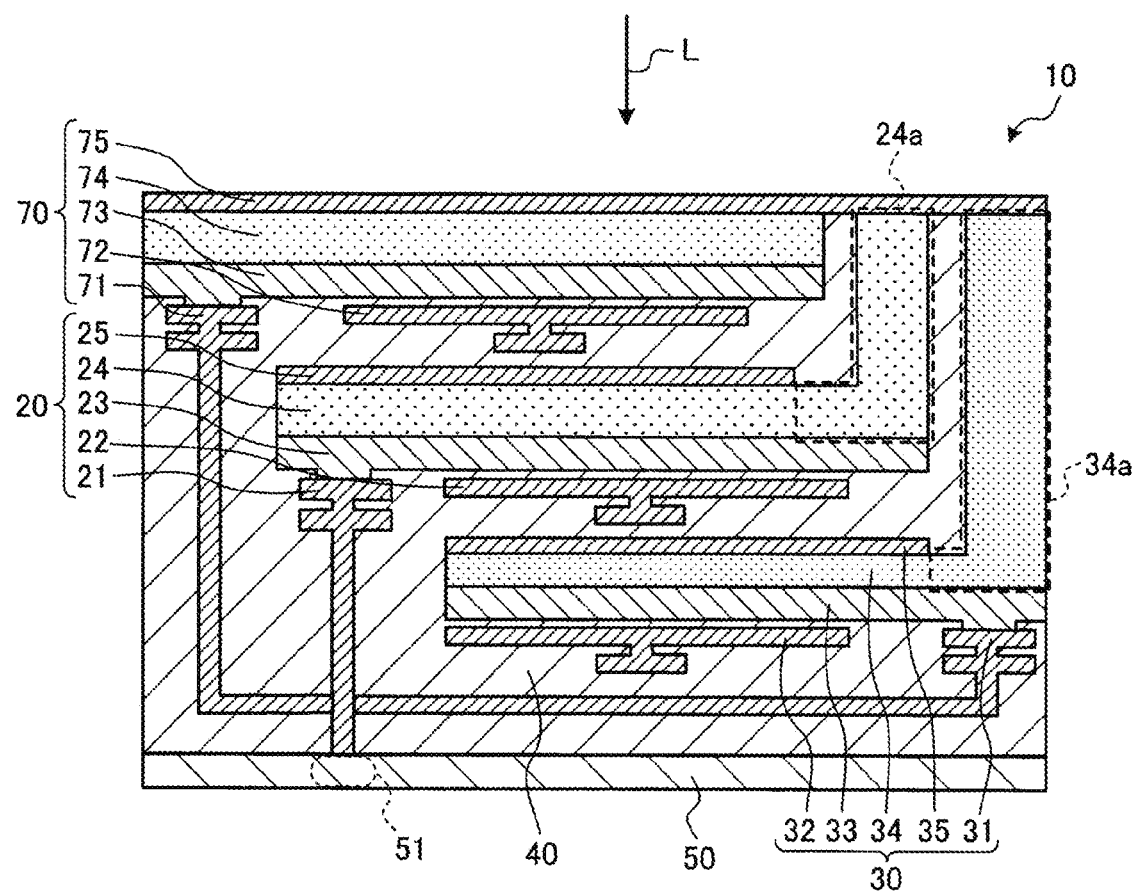
FIG. 13 is a cross-sectional view schematically illustrating a structure of a pixel array portion according to Modification Example 5 of the embodiment of the present disclosure.

In addition, as illustrated in FIG. 13, the floating diffusion 51 may be shared by the photoelectric conversion portion 20, the photoelectric conversion portion 30, and the photoelectric conversion portion 70 provided in one unit pixel 11. FIG. 13 is a cross-sectional view schematically illustrating a structure of the pixel array portion 10 according to Modification Example 5 of the embodiment of the present disclosure.

Thereby, it is not necessary to provide individual floating diffusions 52 and 53 in the photoelectric conversion portion 30 and the photoelectric conversion portion 70, and thus it is possible to simplify a circuit configuration inside the pixel array portion 10.

Thus, according to Modification Example 5, it is possible to reduce manufacturing costs of the pixel array portion 10.

Meanwhile, the order of arrangement of three colors photoelectrically converted by the photoelectric conversion portions 20, 30, and 70 and the photodiode 60 exemplified in the above-described embodiment and various modification examples is not limited to the above-described examples, and any order of arrangement may be adopted.

Further, in the above-described embodiment and various modification examples, an example in which each of the photoelectric conversion layers 24, 34, and 74 is configured as a single layer has been described, but the photoelectric conversion layers 24, 34, and 74 are not limited to a case where they are configured as single layers, and may be configured to have a multi-layer structure.

For example, each of the photoelectric conversion layers 24, 34, and 74 may include an electron injection preventing layer that prevents electrons from being injected from the second electrodes 25, 35, and 75 on a light incidence side of a layer that performs photoelectric conversion, in addition to a layer that performs photoelectric conversion of light L.

In addition, each of the photoelectric conversion layers 24, 34, and 74 may include an electron transport layer that transports electrons on a side opposite to a light incidence side of a layer that performs photoelectric conversion, in addition to a layer that performs photoelectric conversion of light L. Further, each of the photoelectric conversion layers 24, 34, and 74 may include both of the above-described electron injection preventing layer and electron transport layer, in addition to a layer that performs photoelectric conversion of light L.

Further, in the above-described embodiment and various modification examples, an example in which photoelectric conversion portions and photodiodes provided in three layers in the unit pixel 11 has been described, but the number of layers of the photoelectric conversion portions and the photodiodes provided in the unit pixel 11 is not limited to three, and may be one, two, or four or more.

Details of Manufacturing Step

Manufacturing Step of Embodiment

Subsequently, details of the manufacturing steps in the embodiment and various modification examples will be described with reference to FIGS. 14A, 14B, 14C, 14D, 14E, 14F, 14G, 14H, 14I, 14J, 14K, 14L, 14M, 14N, 14O, 14P, 14Q, 14R, 14S, 14T, 14U, 15A, 15B, 15C, 15D, 15E, 16A, 16B, 16C, 16D, 16E, 17A, 17B, 17C, 17D, 17E, 17F, 17G, 17H, 17I, 18A, 18B, 18C, 18D, 18E, 18F, 19A, 19B, 19C, 19D, 19E, 19F, 19G, 19H, 19I, 19J, 19K, 19L, 20, 21, and 22. FIGS. 14A, 14B, 14C, 14D, 14E, 14F, 14G, 14H, 14I, 14J, 14K, 14L, 14M, 14N, 14O, 14P, 14Q, 14R, 14S, 14T, and 14U are cross-sectional views schematically illustrating a manufacturing step for the pixel array portion 10 according to the embodiment of the present disclosure.

Meanwhile, in the drawings illustrating details of a manufacturing step below, the semiconductor layer 50 (see FIG. 2) is not illustrated for ease of understanding. In addition, the drawings illustrate a state where the photodiode 60 and various pixel transistors, various wirings, the floating diffusions 51 to 53, and the like illustrated in FIG. 4 have already been formed in the semiconductor layer 50.

In addition, various steps for forming the photoelectric conversion portion 20 and the photoelectric conversion portion 30 on the surface of the semiconductor layer 50 will be described below.

Figure 14A:
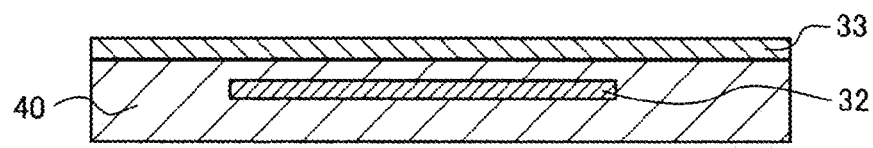
FIG. 14A is a cross-sectional view schematically illustrating a manufacturing step for the pixel array portion according to the embodiment of the present disclosure.

As illustrated in FIG. 14A, the insulating layer 40 is formed on the surface of the semiconductor layer 50 (see FIG. 2), and the first electrode 31 (see FIG. 2) not illustrated in the drawing and the charge storage electrode 32 are formed inside the insulating layer 40. Then, the charge storage layer 33 is formed on the surface of the insulating layer 40 so as to cover the first electrode 31 and the insulating layer 40.

Such a charge storage layer 33 is provided to be in contact with the surface of the first electrode 21 and to be adjacent to the charge storage electrode 22 through the insulating layer 40. Here, a method of forming the insulating layer 40, the first electrode 31, and the charge storage electrode 32 can be adopted from known methods of the related art. Meanwhile, for ease of understanding, the first electrode 31 is not illustrated in the following drawings.

Figure 14B:
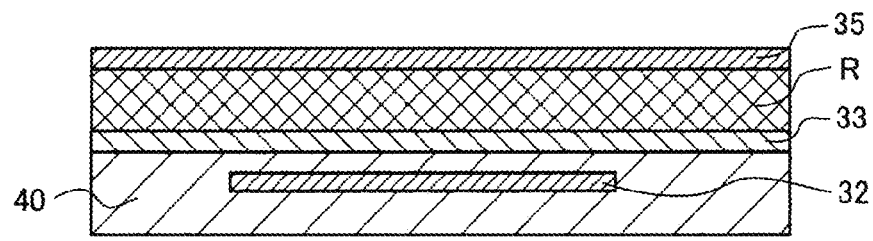
FIG. 14B is a cross-sectional view schematically illustrating a manufacturing step for the pixel array portion according to the embodiment of the present disclosure.

Next, as illustrated in FIG. 14B, a removal material R and the second electrode 35 are formed in order on the surface of the charge storage layer 33. Meanwhile, the removal material R is provided at a position corresponding to the photoelectric conversion layer 34 in the pixel array portion 10.

Figure 14C:
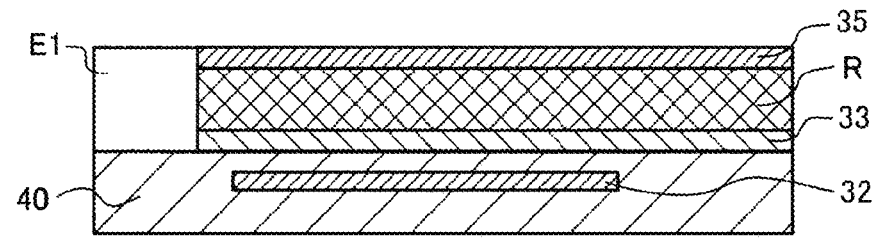
FIG. 14C is a cross-sectional view schematically illustrating a manufacturing step for the pixel array portion according to the embodiment of the present disclosure.

Such a removal material R is a material formed to be removable by predetermined processing and is, for example, a resist material which is removable by chemical etching. Meanwhile, the removal material R is not limited to a resist material, and may be a different material as long as it is a material formed to be removable by predetermined processing. In addition, a method of forming the removal material R and the second electrode 35 can be appropriately adopted from known methods of the related art Next, as illustrated in FIG. 14C, predetermined regions in the second electrode 35, the removal material R, and the charge storage layer 33 are etched by a known method of the related art, thereby forming an etching region E1.

Figure 14D:
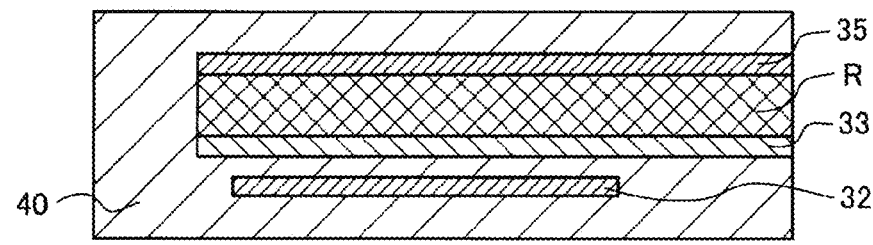
FIG. 14D is a cross-sectional view schematically illustrating a manufacturing step for the pixel array portion according to the embodiment of the present disclosure.

Next, as illustrated in FIG. 14D, the insulating layer 40 is formed to fill in the etching region E1 and cover the surface of the second electrode 35.

Figure 14E:
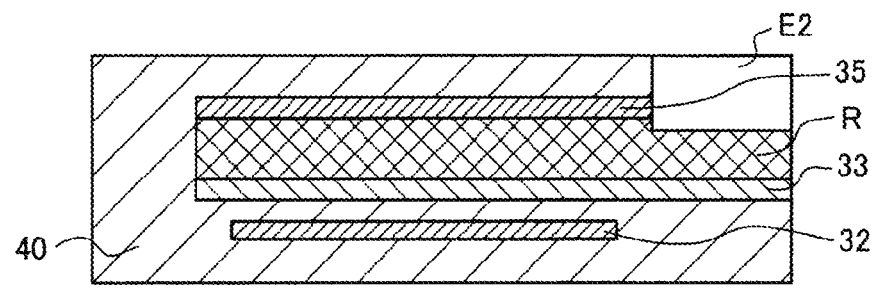
FIG. 14E is a cross-sectional view schematically illustrating a manufacturing step for the pixel array portion according to the embodiment of the present disclosure.

Next, as illustrated in FIG. 14E, predetermined regions in the insulating layer 40, the second electrode 35, and the removal material R are etched by a known method of the related art, thereby forming an etching region E2. Meanwhile, such an etching region E2 is formed at a position corresponding to the protrusion region 34a in the pixel array portion 10 and is formed so as not to penetrate the removal material R.

Figure 14F:
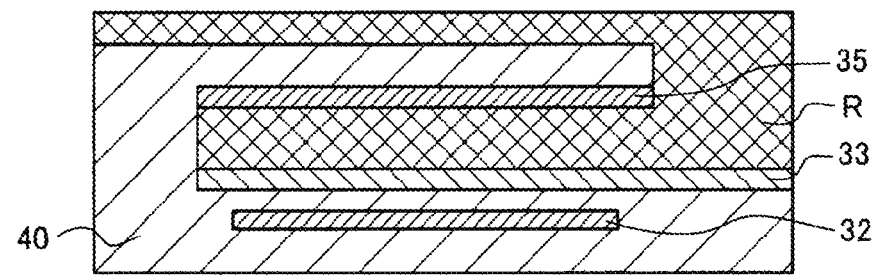
FIG. 14F is a cross-sectional view schematically illustrating a manufacturing step for the pixel array portion according to the embodiment of the present disclosure.
Figure 14G:
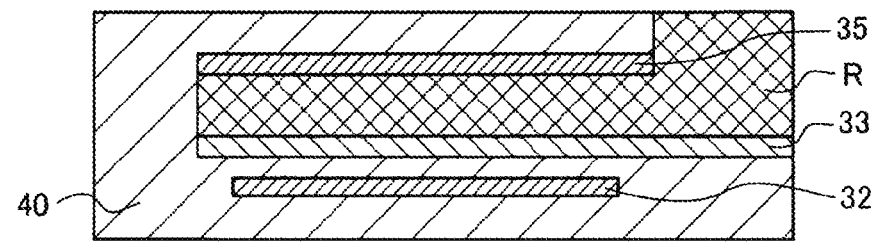
FIG. 14G is a cross-sectional view schematically illustrating a manufacturing step for the pixel array portion according to the embodiment of the present disclosure.

Next, as illustrated in FIG. 14F, the removal material R is formed to fill in the etching region E2 and cover the surface of the insulating layer 40. In addition, as illustrated in FIG. 14G, the removal material R is removed so that the surface of the insulating layer 40 and the surface of the removal material R are substantially flush with each other.

Figure 14H:
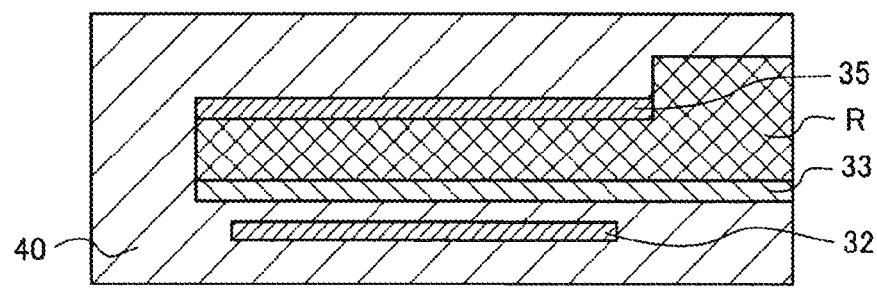
FIG. 14H is a cross-sectional view schematically illustrating a manufacturing step for the pixel array portion according to the embodiment of the present disclosure.
Figure 14I:
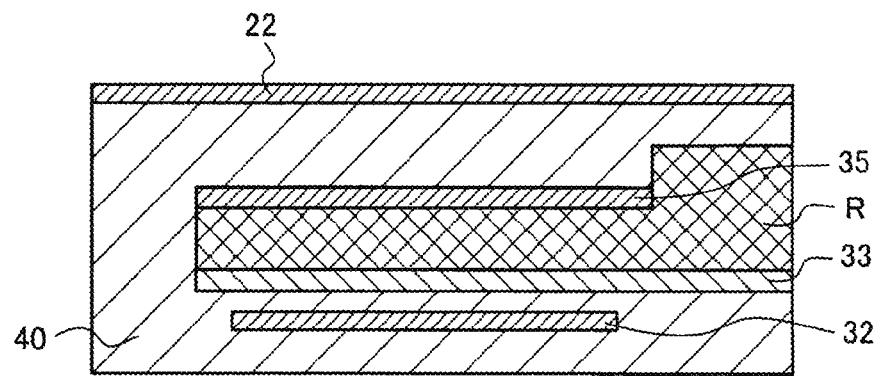
FIG. 14I is a cross-sectional view schematically illustrating a manufacturing step for the pixel array portion according to the embodiment of the present disclosure.

Next, as illustrated in FIG. 14H, the insulating layer 40 is formed to cover the surface of the insulating layer 40 and the surface of the removal material R. In addition, as illustrated in FIG. 14I, the charge storage electrode 22 is formed to cover the surface of the insulating layer 40.

Figure 14J:
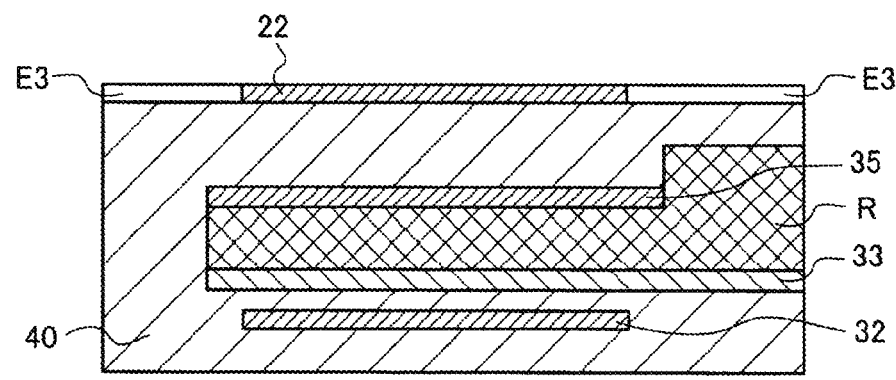
FIG. 14J is a cross-sectional view schematically illustrating a manufacturing step for the pixel array portion according to the embodiment of the present disclosure.
Figure 14K:
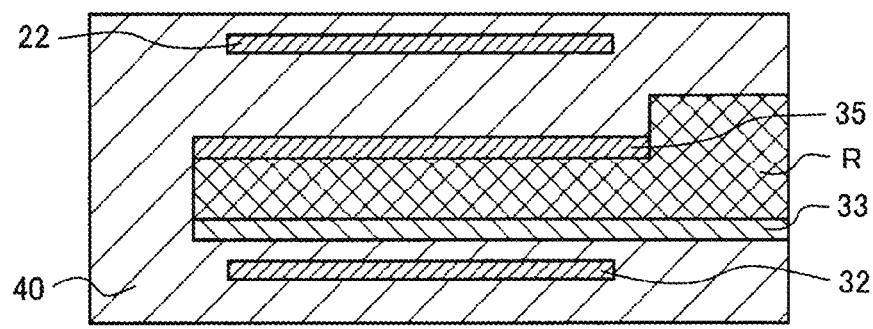
FIG. 14K is a cross-sectional view schematically illustrating a manufacturing step for the pixel array portion according to the embodiment of the present disclosure.

Next, as illustrated in FIG. 14J, a predetermined region in the charge storage electrode 22 is etched by a known method of the related art, thereby forming an etching region E3. In addition, as illustrated in FIG. 14K, the insulating layer 40 is formed to fill in the etching region E3 and cover the surface of the charge storage electrode 22.

Figure 14L:
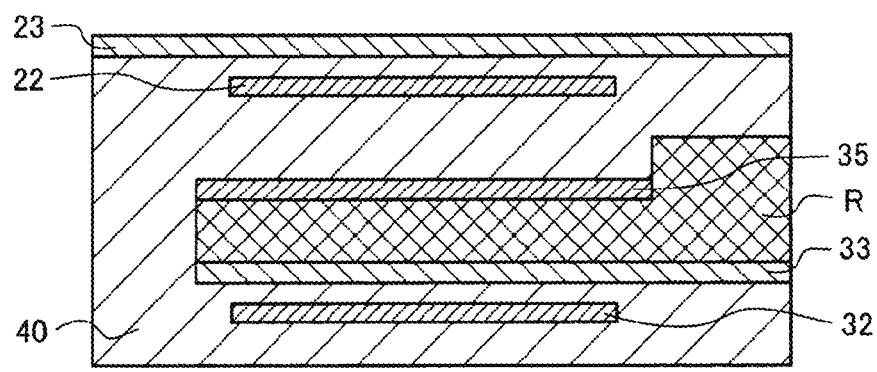
FIG. 14L is a cross-sectional view schematically illustrating a manufacturing step for the pixel array portion according to the embodiment of the present disclosure.

Next, as illustrated in FIG. 14L, the charge storage layer 23 is formed to cover the surface of the insulating layer 40. Meanwhile, in the steps up to FIG. 14L, the first electrode 21 (see FIG. 2) of the photoelectric conversion portion 20 is also formed in parallel, but a process of forming such a first electrode 21 will not be illustrated and described.

Figure 14M:
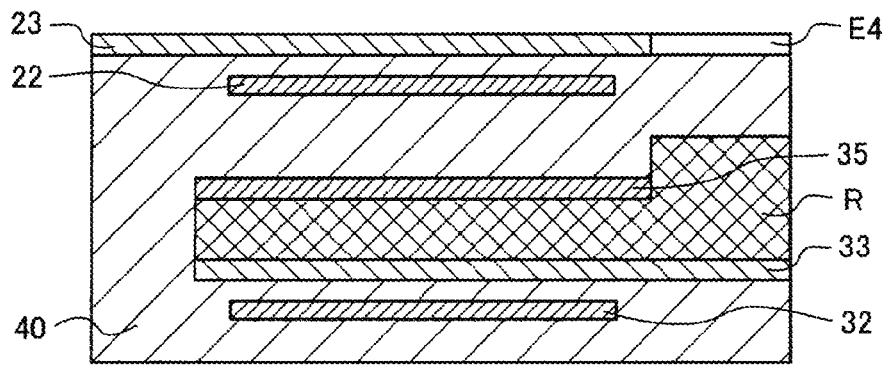
FIG. 14M is a cross-sectional view schematically illustrating a manufacturing step for the pixel array portion according to the embodiment of the present disclosure.
Figure 14N:
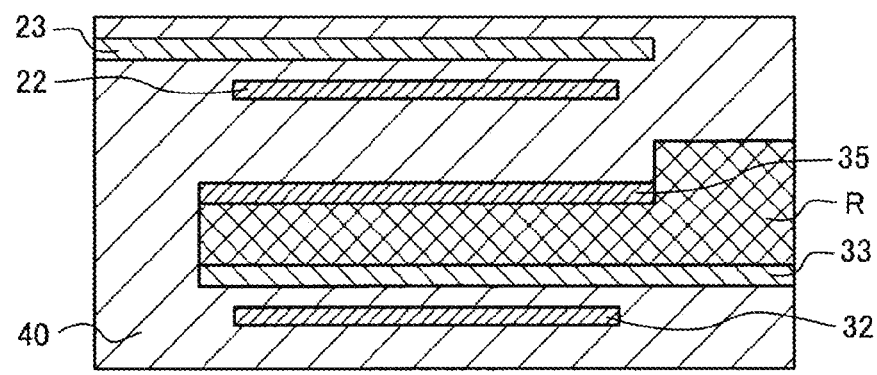
FIG. 14N is a cross-sectional view schematically illustrating a manufacturing step for the pixel array portion according to the embodiment of the present disclosure.

Next, as illustrated in FIG. 14M, a predetermined region in the charge storage layer 23 is etched by a known method of the related art, thereby forming an etching region E4. In addition, as illustrated in FIG. 14N, the insulating layer 40 is formed to fill in the etching region E4 and cover the surface of the charge storage layer 23.

Figure 14O:
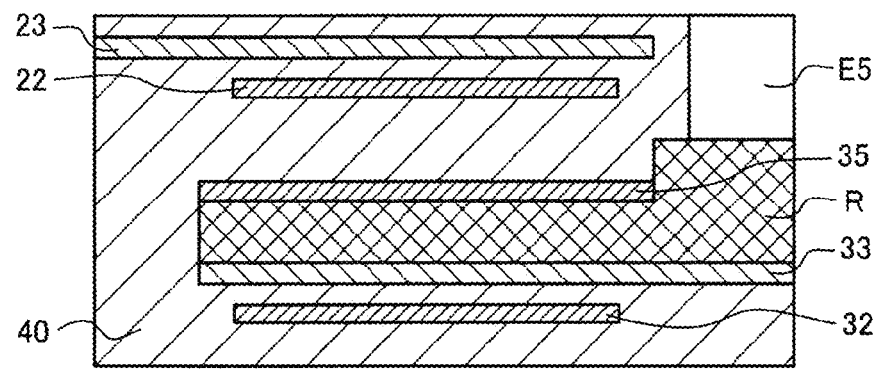
FIG. 14O is a cross-sectional view schematically illustrating a manufacturing step for the pixel array portion according to the embodiment of the present disclosure.

Next, as illustrated in FIG. 14O, a predetermined region in the insulating layer 40 is etched by a known method of the related art, thereby forming an etching region E5. Meanwhile, such an etching region E5 is formed to reach the removal material R which is formed to protrude toward a light incidence side.

Figure 14P:
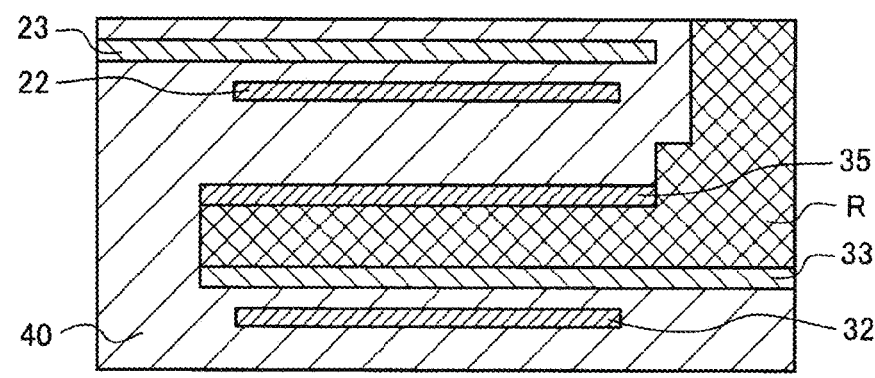
FIG. 14P is a cross-sectional view schematically illustrating a manufacturing step for the pixel array portion according to the embodiment of the present disclosure.

Next, as illustrated in FIG. 14P, the removal material R is formed to fill in the etching region E5. In addition, as illustrated in FIG. 14Q, the removal material R is removed by predetermined processing (for example, chemical etching), and a void V1 is formed in a region in which such a removal material R is provided.

Figure 14Q:
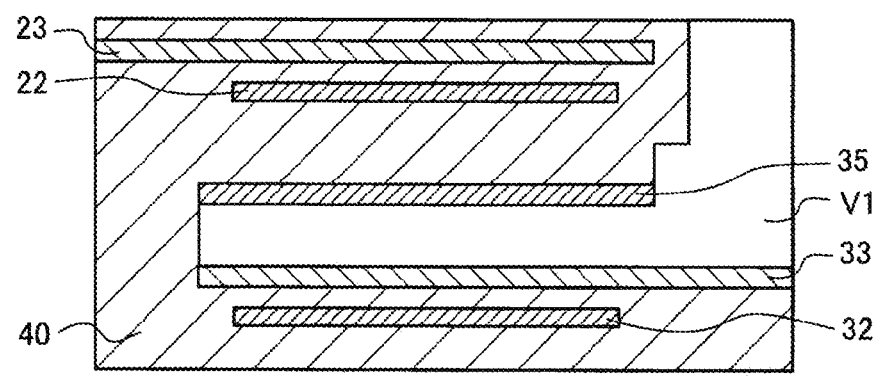
FIG. 14Q is a cross-sectional view schematically illustrating a manufacturing step for the pixel array portion according to the embodiment of the present disclosure.

Further, in the embodiment, annealing is performed at a predetermined temperature in a state where the void V1 illustrated in FIG. 14Q is formed.

Here, in the state illustrated in FIG. 14Q, since neither the photoelectric conversion layer 24 or the photoelectric conversion layer 34, which are constituted by an organic semiconductor material, is formed, annealing can be performed at a desired temperature without worrying about damage to the photoelectric conversion layer 24 and the photoelectric conversion layer 34. Thus, according to the embodiment, it is possible to form an element having satisfactory characteristics within the pixel array portion 10.

Figure 14R:
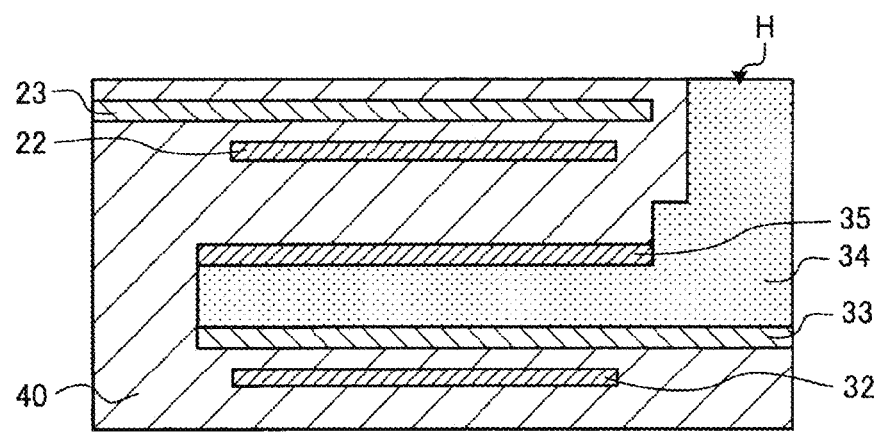
FIG. 14R is a cross-sectional view schematically illustrating a manufacturing step for the pixel array portion according to the embodiment of the present disclosure.

Next, as illustrated in FIG. 14R, a liquid raw material of the photoelectric conversion layer 34 is injected to fill the void V1 through an injection port H that opens upward from the void V1. Then, the photoelectric conversion layer 34 is formed in the void V1 by drying the liquid raw material injected into the void V1 at a predetermined temperature.

Here, since the void V1 is formed between the charge storage layer 33 and the second electrode 35, the photoelectric conversion layer 34 can be formed between the charge storage layer 33 and the second electrode 35 in the embodiment.

Figure 14S:
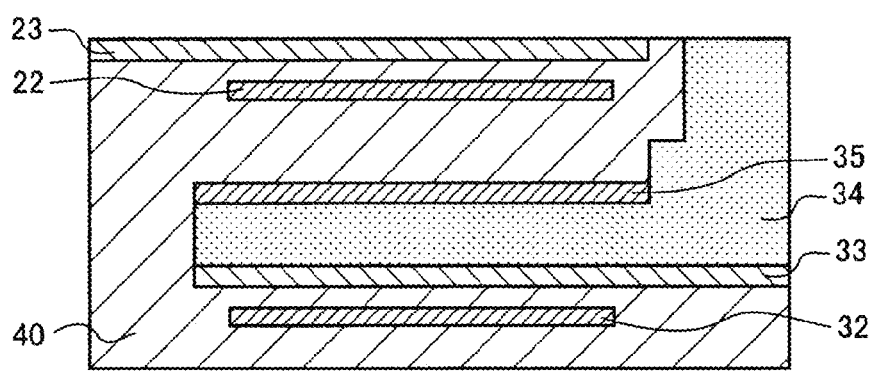
FIG. 14S is a cross-sectional view schematically illustrating a manufacturing step for the pixel array portion according to the embodiment of the present disclosure.
Figure 14T:
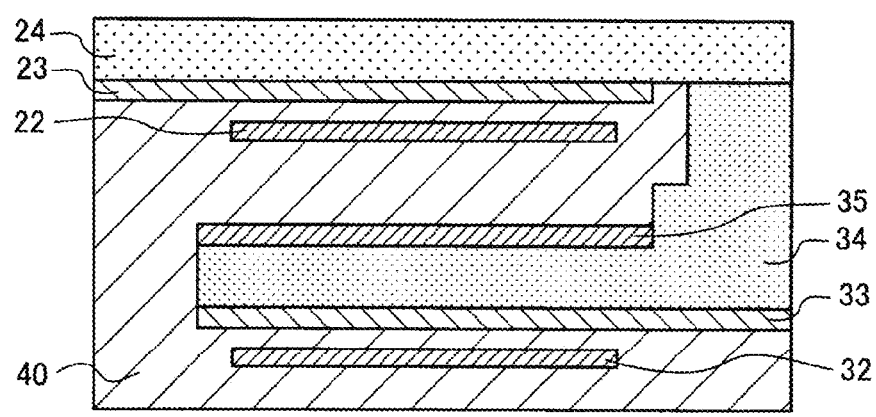
FIG. 14T is a cross-sectional view schematically illustrating a manufacturing step for the pixel array portion according to the embodiment of the present disclosure.

Next, as illustrated in FIG. 14S, the insulating layer 40 and the photoelectric conversion layer 34 are removed by a known method of the related art so that the surface of the charge storage layer 23, the surface of the insulating layer 40, and the surface of the photoelectric conversion layer 34 are substantially flush with each other. In addition, as illustrated in FIG. 14T, the photoelectric conversion layer 24 is formed by a known method of the related art so as to cover the surfaces of the charge storage layer 23, the insulating layer 40, and the photoelectric conversion layer 34.

For example, a liquid raw material of the photoelectric conversion layer 24 is applied to the surfaces of the charge storage layer 23, the insulating layer 40, and the photoelectric conversion layer 34, and such a liquid raw material is dried at a predetermined temperature, thereby forming the photoelectric conversion layer 24. Meanwhile, a forming process for the photoelectric conversion layer 24 is not limited to the above-described method, and may be any of other methods such as a vapor growth method.

Figure 14U:
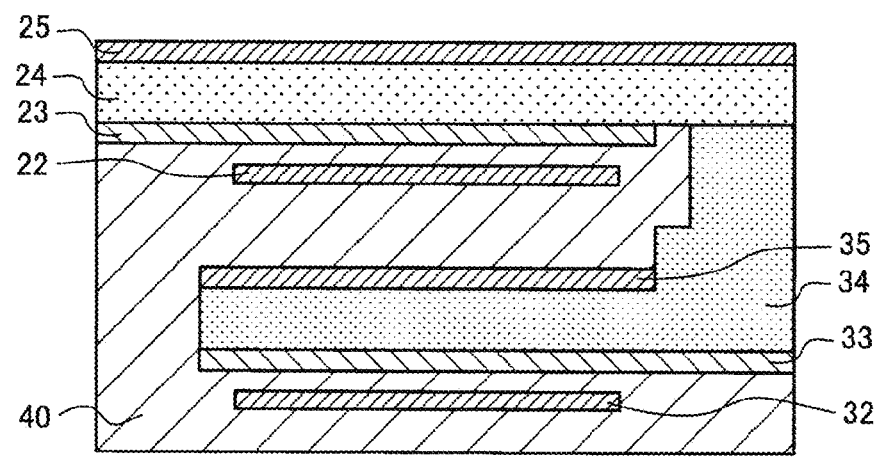
FIG. 14U is a cross-sectional view schematically illustrating a manufacturing step for the pixel array portion according to the embodiment of the present disclosure.

Finally, as illustrated in FIG. 14U, the second electrode 25 is formed by a known method of the related art so as to cover the surface of the photoelectric conversion layer 24, and thus a manufacturing step for the pixel array portion 10 according to the embodiment is finished.

Manufacturing Step of Modification Example 1

FIGS. 15A, 15B, 15C, 15D, and 15E are cross-sectional views schematically illustrating a manufacturing step for the pixel array portion 10 according to Modification Example 1 of the embodiment of the present disclosure. Meanwhile, the steps up to the middle in Modification Example 1 are similar to the steps illustrated in FIGS. 14A, 14B, 14C, 14D, 14E, 14F, 14G, 14H, 14I, 14J, 14K, 14L, 14M, 14N, 14O, 14P, and 14Q, and thus description thereof will be omitted.

Figure 15A:
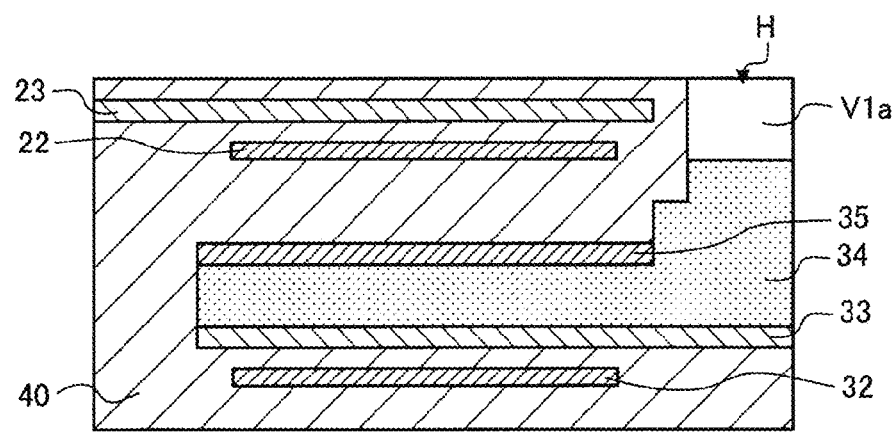
FIG. 15A is a cross-sectional view schematically illustrating a manufacturing step for the pixel array portion according to Modification Example 1 of the embodiment of the present disclosure.

Subsequently to the step illustrated in FIG. 14Q, annealing is performed at a predetermined temperature in a state where the void V1 is formed. In addition, as illustrated in FIG. 15A, a liquid raw material of the photoelectric conversion layer 34 is injected such that the void V1 is not filled through an injection port H that opens upward from the void V1.

Then, the photoelectric conversion layer 34 is formed in the void V1 by drying the liquid raw material injected into the void V1 at a predetermined temperature. Meanwhile, the liquid raw material of the photoelectric conversion layer 34 is injected such that the void V1 is not filled, and thus a portion of the void V1 remains as a void V1a.

Figure 15B:
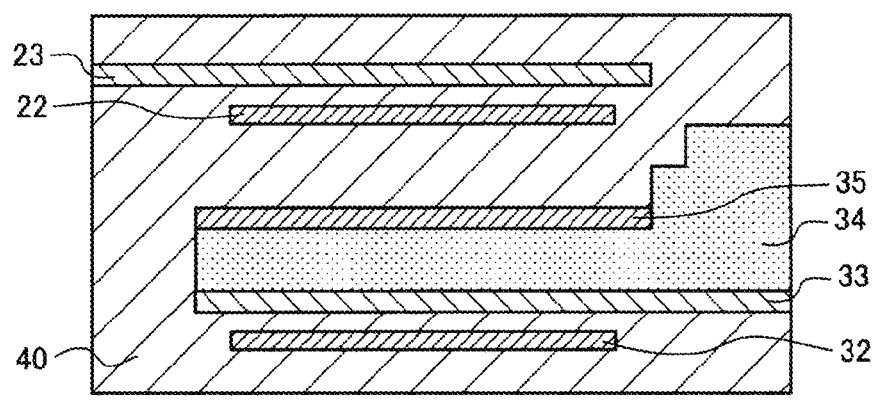
FIG. 15B is a cross-sectional view schematically illustrating a manufacturing step for the pixel array portion according to Modification Example 1 of the embodiment of the present disclosure.

Next, as illustrated in FIG. 15B, the insulating layer 40 is formed to fill in the void V1a and cover the surface of the insulating layer 40.

Figure 15C:
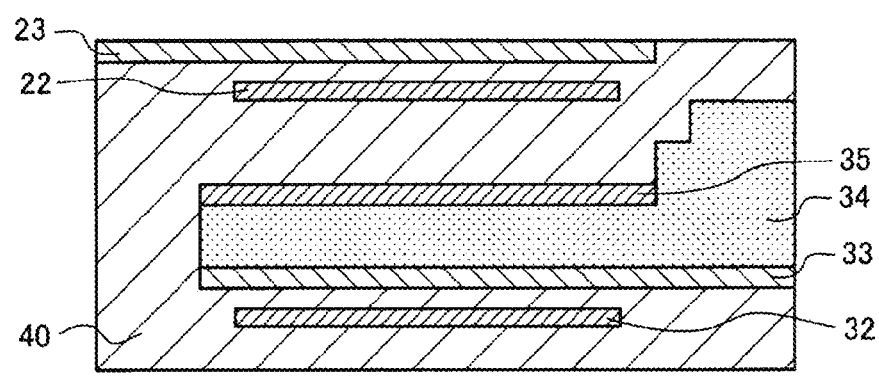
FIG. 15C is a cross-sectional view schematically illustrating a manufacturing step for the pixel array portion according to Modification Example 1 of the embodiment of the present disclosure.
Figure 15D:
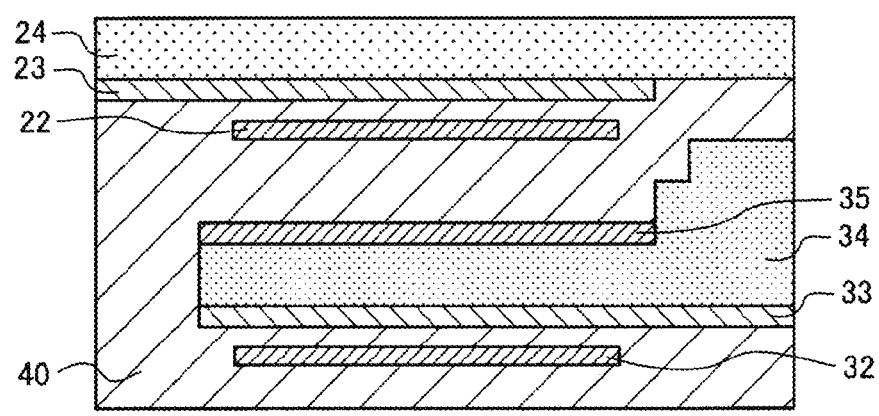
FIG. 15D is a cross-sectional view schematically illustrating a manufacturing step for the pixel array portion according to Modification Example 1 of the embodiment of the present disclosure.

Next, as illustrated in FIG. 15C, the insulating layer 40 is removed by a known method of the related art so that the surface of the charge storage layer 23 and the surface of the insulating layer 40 are substantially flush with each other. In addition, as illustrated in FIG. 15D, the photoelectric conversion layer 24 is formed by a known method of the related art so as to cover the surfaces of the charge storage layer 23 and the insulating layer 40.

Figure 15E:
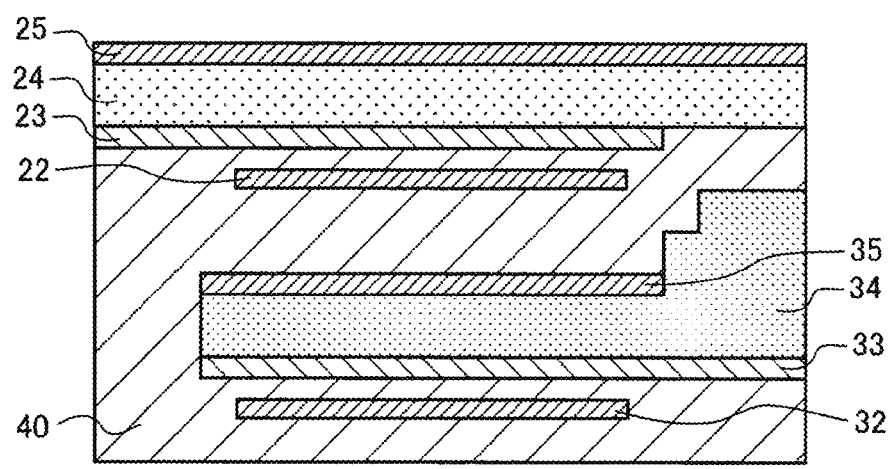
FIG. 15E is a cross-sectional view schematically illustrating a manufacturing step for the pixel array portion according to Modification Example 1 of the embodiment of the present disclosure.

Finally, as illustrated in FIG. 15E, the second electrode 25 is formed by a known method of the related art so as to cover the surface of the photoelectric conversion layer 24, and thus a manufacturing step for the pixel array portion 10 according to Modification Example 1 of the embodiment is finished.

Manufacturing Step of Modification Example 2

FIGS. 16A, 16B, 16C, 16D, and 16E are cross-sectional views schematically illustrating a manufacturing step for the pixel array portion 10 according to Modification Example 2 of the embodiment of the present disclosure. Meanwhile, the steps up to the middle in Modification Example 2 are similar to the steps illustrated in FIGS. 14A, 14B, 14C, 14D, 14E, 14F, 14G, 14H, 14I, 14J, 14K, 14L, 14M, 14N, 14O, 14P, and 14Q, and thus description thereof will be omitted.

Figure 16A:
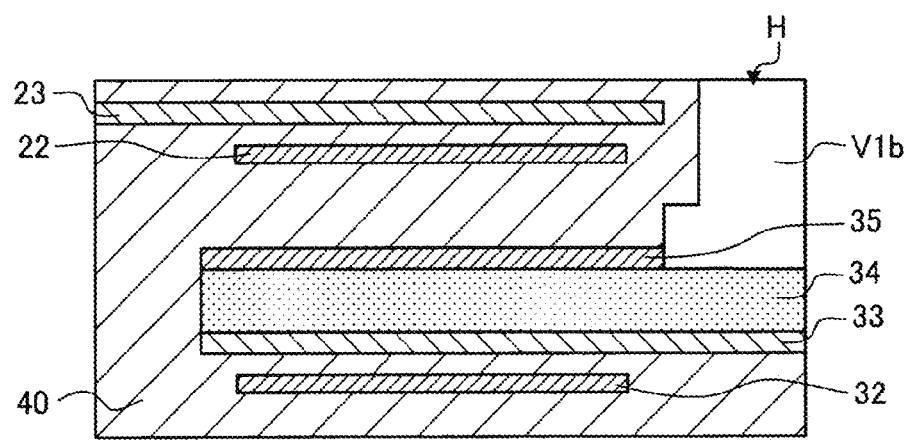
FIG. 16A is a cross-sectional view schematically illustrating a manufacturing step for the pixel array portion according to Modification Example 2 of the embodiment of the present disclosure.

Subsequently to the step illustrated in FIG. 14Q, annealing is performed at a predetermined temperature in a state where the void V1 is formed. In addition, as illustrated in FIG. 16A, a liquid raw material of the photoelectric conversion layer 34 is injected through an injection port H that opens upward from the void V1 such that the bottom surface of the second electrode 35 and a liquid surface are substantially flush with each other.

Then, the photoelectric conversion layer 34 is formed in the void V1 by drying the liquid raw material injected into the void V1 at a predetermined temperature. Meanwhile, the liquid raw material of the photoelectric conversion layer 34 is injected such that the bottom surface of the second electrode 35 and the liquid surface are substantially flush with each other, and thus a portion of the void V1 remains as a void V1b.

Figure 16B:
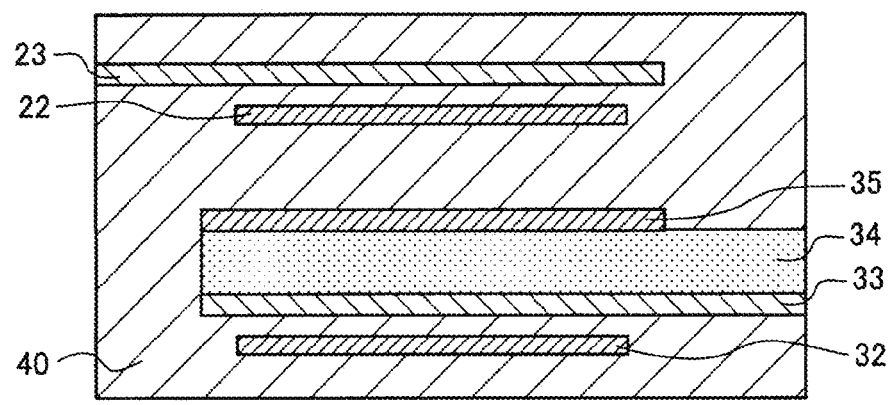
FIG. 16B is a cross-sectional view schematically illustrating a manufacturing step for the pixel array portion according to Modification Example 2 of the embodiment of the present disclosure.

Next, as illustrated in FIG. 16B, the insulating layer 40 is formed to fill in the void V1b and cover the surface of the insulating layer 40.

Figure 16C:
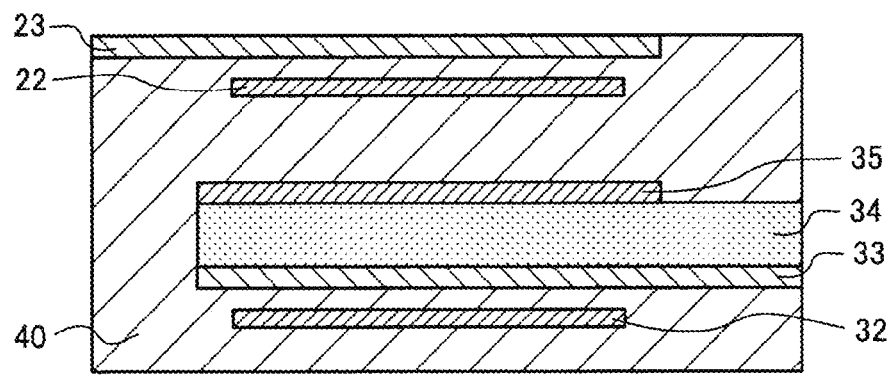
FIG. 16C is a cross-sectional view schematically illustrating a manufacturing step for the pixel array portion according to Modification Example 2 of the embodiment of the present disclosure.
Figure 16D:
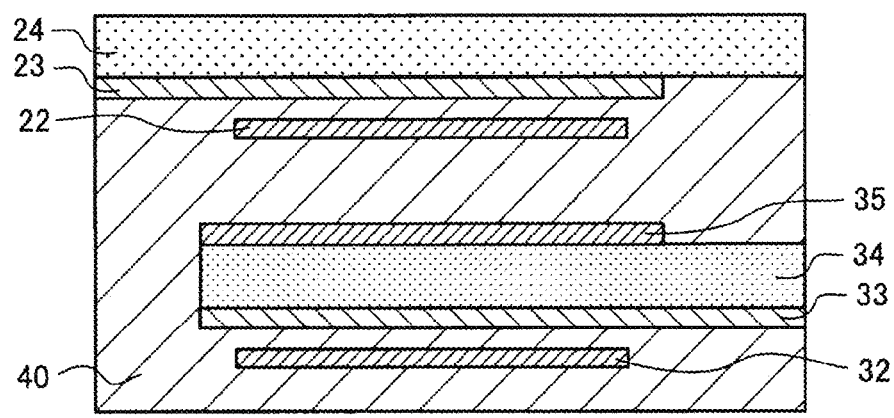
FIG. 16D is a cross-sectional view schematically illustrating a manufacturing step for the pixel array portion according to Modification Example 2 of the embodiment of the present disclosure.

Next, as illustrated in FIG. 16C, the insulating layer 40 is removed such that the surface of the charge storage layer 23 and the surface of the insulating layer 40 are substantially flush with each other. In addition, as illustrated in FIG. 16D, the photoelectric conversion layer 24 is formed to cover the surfaces of the charge storage layer 23 and the insulating layer 40.

Figure 16E:
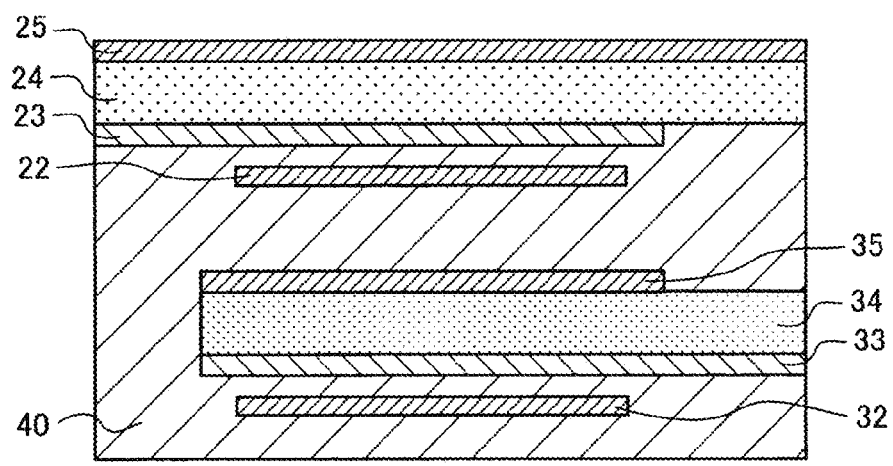
FIG. 16E is a cross-sectional view schematically illustrating a manufacturing step for the pixel array portion according to Modification Example 2 of the embodiment of the present disclosure.

Finally, as illustrated in FIG. 16E, the second electrode 25 is formed to cover the surface of the photoelectric conversion layer 24, and thus a manufacturing step for the pixel array portion 10 according to Modification Example 2 of the embodiment is finished.

Manufacturing Step of Modification Example 3

FIGS. 17A, 17B, 17C, 17D, 17E, 17F, 17G, 17H, and 17I are cross-sectional views schematically illustrating a manufacturing step for the pixel array portion 10 according to Modification Example 3 of the embodiment of the present disclosure. Meanwhile, the steps up to the middle in Modification Example 3 are similar to the steps illustrated in FIGS. 14A, 14B, 14C, 14D, 14E, 14F, 14G, 14H, 14I, 14J, 14K, 14L, 14M, 14N, 14O, and 14P, and thus description thereof will be omitted.

Figure 17A:
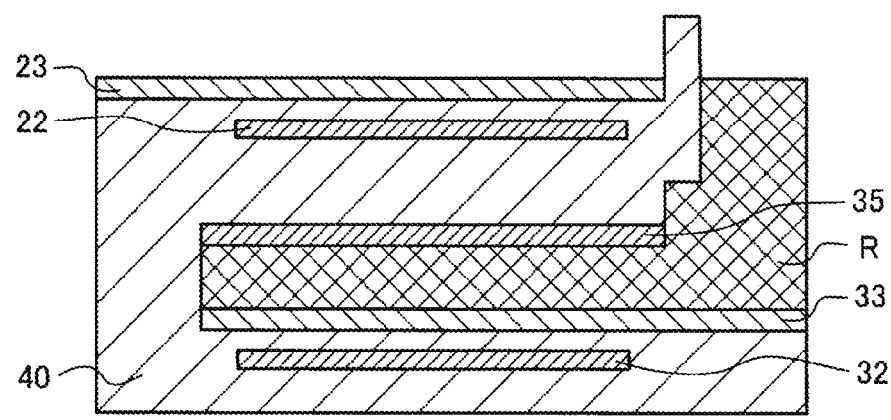
FIG. 17A is a cross-sectional view schematically illustrating a manufacturing step for the pixel array portion according to Modification Example 3 of the embodiment of the present disclosure.

Subsequently to the step illustrated in FIG. 14P, as illustrated in FIG. 17A, the insulating layer 40 and the removal material R are removed such that the surface of the charge storage layer 23, the surface of the insulating layer 40, and the surface of the removal material R are substantially flush with each other. Further, the insulating layer 40 is formed on the surface of the insulating layer 40 provided between the charge storage layer 23 and the removal material R.

Figure 17B:
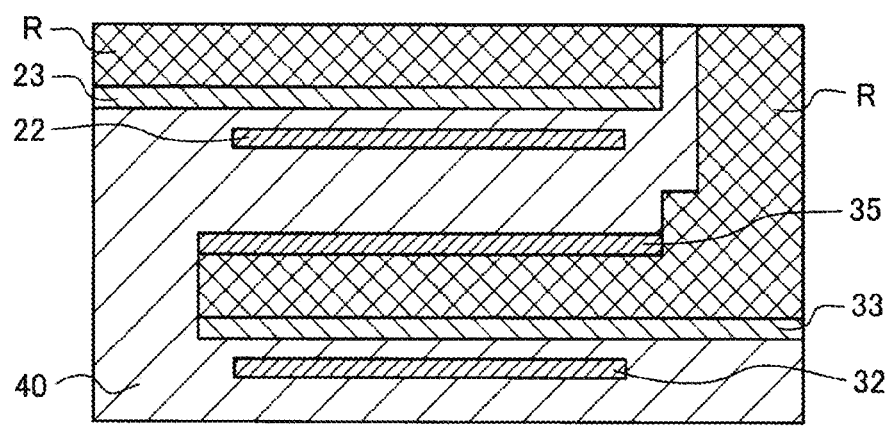
FIG. 17B is a cross-sectional view schematically illustrating a manufacturing step for the pixel array portion according to Modification Example 3 of the embodiment of the present disclosure.
Figure 17C:
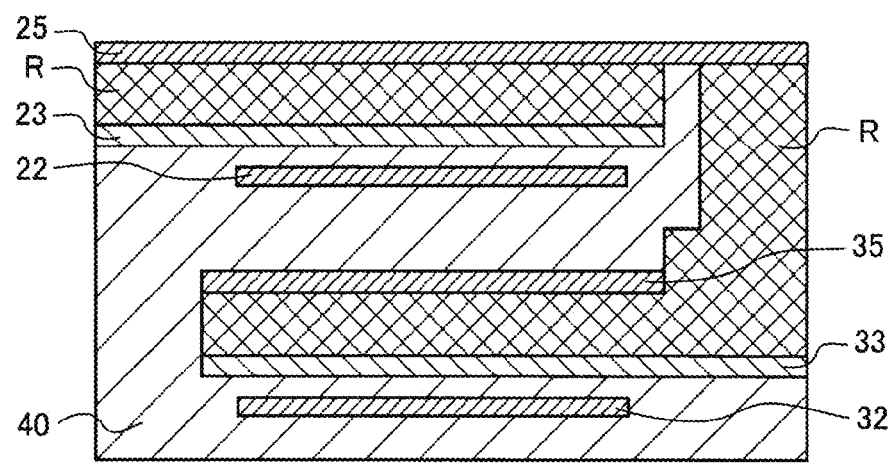
FIG. 17C is a cross-sectional view schematically illustrating a manufacturing step for the pixel array portion according to Modification Example 3 of the embodiment of the present disclosure.

Next, as illustrated in FIG. 17B, the removal material R is formed to cover the surface of the charge storage layer 23 and the surface of the removal material R and is formed such that the insulating layer 40 and the surfaces are substantially flush with each other. In addition, as illustrated in FIG. 17C, the second electrode 25 is formed to cover the surfaces of the removal material R and the insulating layer 40.

Figure 17D:
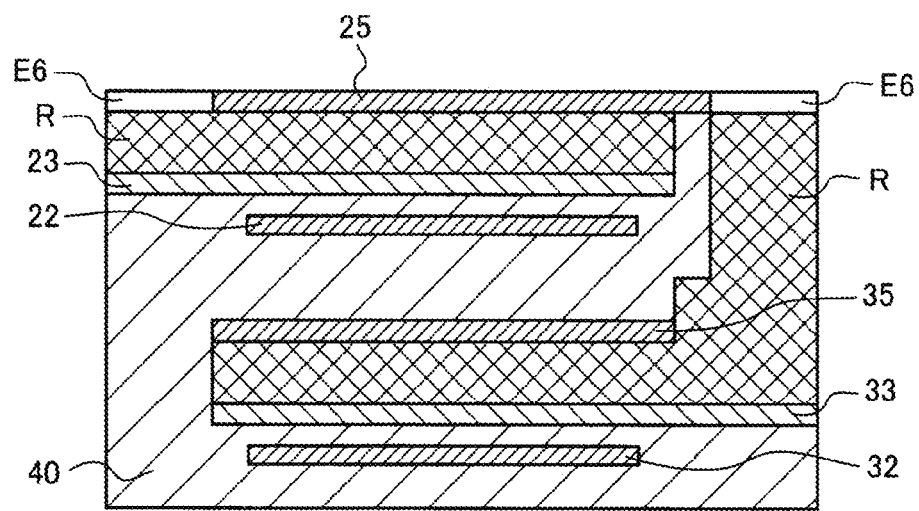
FIG. 17D is a cross-sectional view schematically illustrating a manufacturing step for the pixel array portion according to Modification Example 3 of the embodiment of the present disclosure.

Next, as illustrated in FIG. 17D, a predetermined region in the second electrode 25 is etched by a known method of the related art, thereby forming an etching region E6. Meanwhile, such an etching region E6 is provided to expose the removal material R formed on the surface of the charge storage layer 23 and the removal material R formed on the surface of the charge storage layer 33.

Figure 17E:
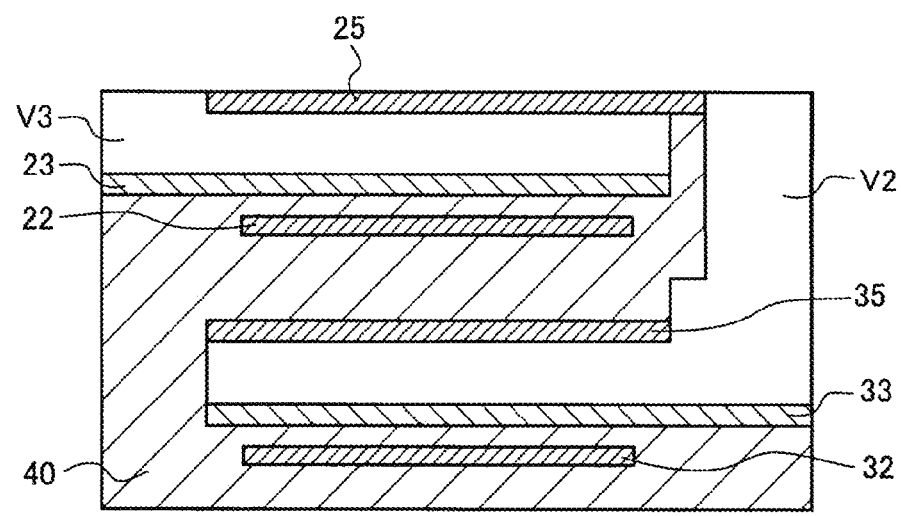
FIG. 17E is a cross-sectional view schematically illustrating a manufacturing step for the pixel array portion according to Modification Example 3 of the embodiment of the present disclosure.

Next, as illustrated in FIG. 17E, the removal material R is removed by predetermined processing (for example, chemical etching), and voids V2 and V3 are formed in a region in which such a removal material R is provided. Meanwhile, the void V2 is a void formed between the charge storage layer 33 and the second electrode 35, and the void V3 is a void formed between the charge storage layer 23 and the second electrode 25.

Further, in Modification Example 3, annealing is performed at a predetermined temperature in a state where the voids V2 and V3 illustrated in FIG. 17E are formed.

Figure 17F:
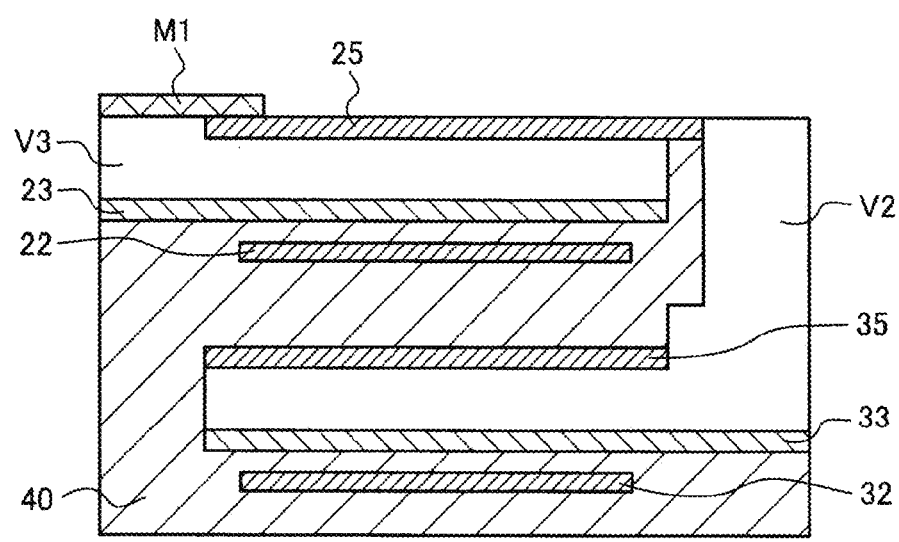
FIG. 17F is a cross-sectional view schematically illustrating a manufacturing step for the pixel array portion according to Modification Example 3 of the embodiment of the present disclosure.

Next, as illustrated in FIG. 17F, a mask M1 is formed to close an opening portion of the void V3. The mask M1, which is, for example, a metal mask, is formed by a known method of the related art.

Figure 17G:
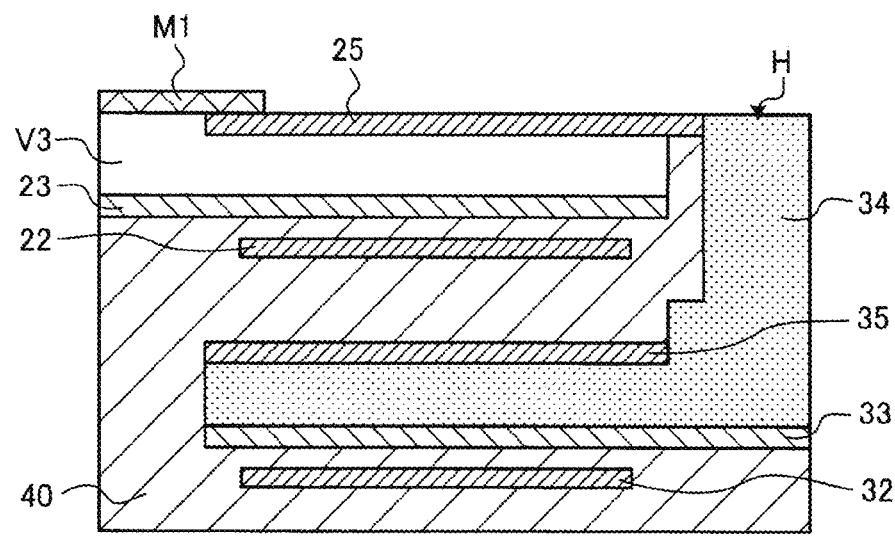
FIG. 17G is a cross-sectional view schematically illustrating a manufacturing step for the pixel array portion according to Modification Example 3 of the embodiment of the present disclosure.
Figure 17H:
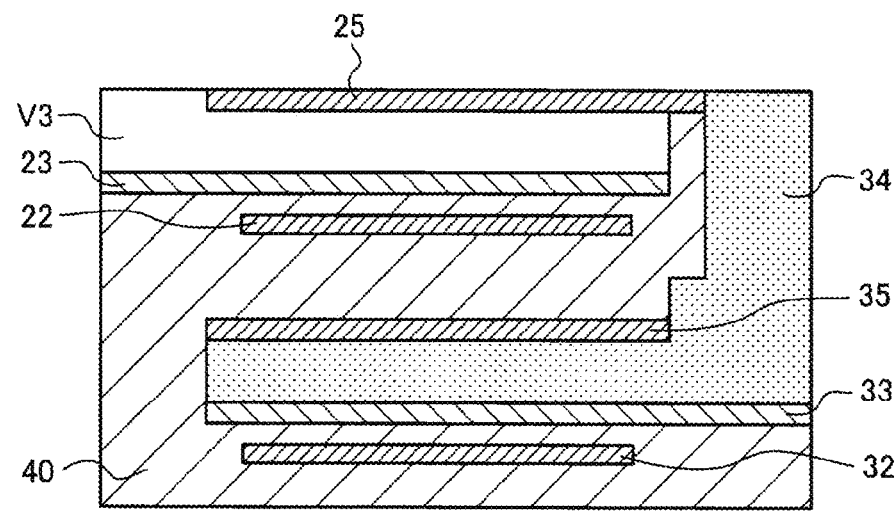
FIG. 17H is a cross-sectional view schematically illustrating a manufacturing step for the pixel array portion according to Modification Example 3 of the embodiment of the present disclosure.

Next, as illustrated in FIG. 17G, a liquid raw material of the photoelectric conversion layer 34 is injected to fill the void V2 through an injection port H that opens upward from the void V2. Then, the photoelectric conversion layer 34 is formed in the void V2 by drying the liquid raw material injected into the void V2 at a predetermined temperature. In addition, as illustrated in FIG. 17H, the mask M1 is removed by a known method of the related art.

Figure 17I:
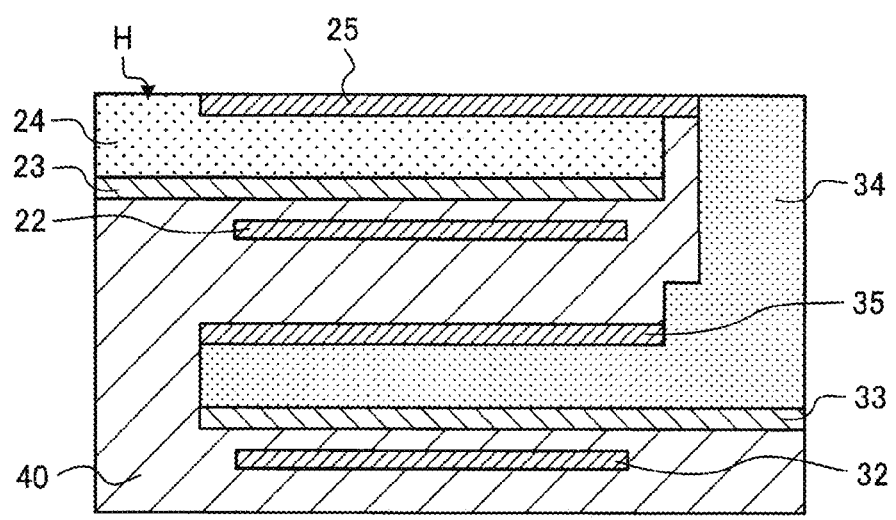
FIG. 17I is a cross-sectional view schematically illustrating a manufacturing step for the pixel array portion according to Modification Example 3 of the embodiment of the present disclosure.

Next, as illustrated in FIG. 17I, a liquid raw material of the photoelectric conversion layer 24 is injected to fill the void V3 through an injection port H that opens upward from the void V3. Finally, the photoelectric conversion layer 24 is formed in the void V3 by drying the liquid raw material injected into the void V3 at a predetermined temperature, and thus a manufacturing step for the pixel array portion 10 according to Modification Example 3 of the embodiment is finished.

Meanwhile, in the above-described example, a case where annealing is performed in the state illustrated in FIG. 17E has been described, but such annealing is not limited to the case where annealing is performed in the state illustrated in FIG. 17E, and may be performed in the state illustrated in FIG. 17F.

Manufacturing Step of Another Example of Modification Example 3

FIGS. 18A, 18B, 18C, 18D, 18E, and 18F are cross-sectional views schematically illustrating a manufacturing step for the pixel array portion 10 according to another example of Modification Example 3 of the embodiment of the present disclosure. Meanwhile, the steps up to the middle in such an example are similar to the steps illustrated in FIGS. 14A, 14B, 14C, 14D, 14E, 14F, 14G, 14H, 14I, 14J, 14K, 14L, 14M, 14N, 14O, and 14P, and thus description thereof will be omitted.

Figure 18A:
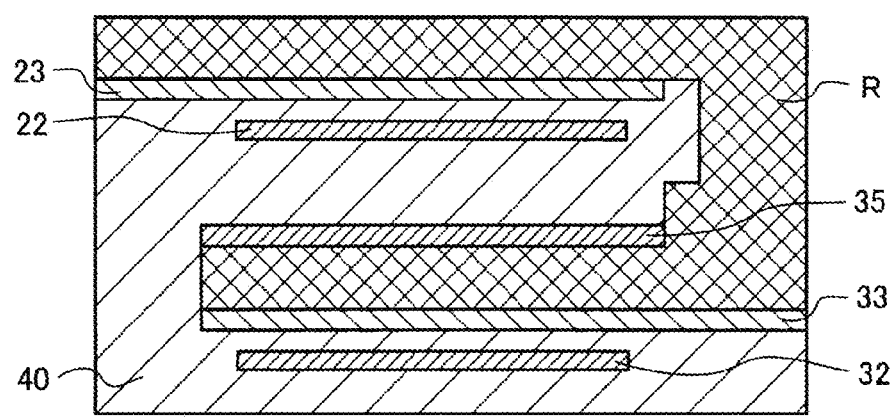
FIG. 18A is a cross-sectional view schematically illustrating a manufacturing step for a pixel array portion according to another example of Modification Example 3 of the embodiment of the present disclosure.

Subsequently to the step illustrated in FIG. 14P, as illustrated in FIG. 18A, the insulating layer 40 and the removal material R are removed such that the surface of the charge storage layer 23, the surface of the insulating layer 40, and the surface of the removal material R are substantially flush with each other. Further, the removal material R is formed to cover the surface of the charge storage layer 23, the surface of the insulating layer 40, and the surface of the removal material R.

Figure 18B:
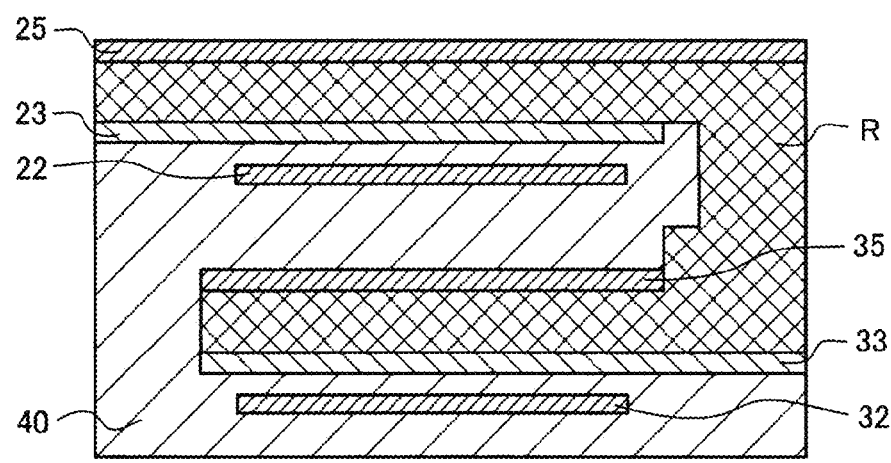
FIG. 18B is a cross-sectional view schematically illustrating a manufacturing step for a pixel array portion according to still another example of Modification Example 3 of the embodiment of the present disclosure.
Figure 18C:
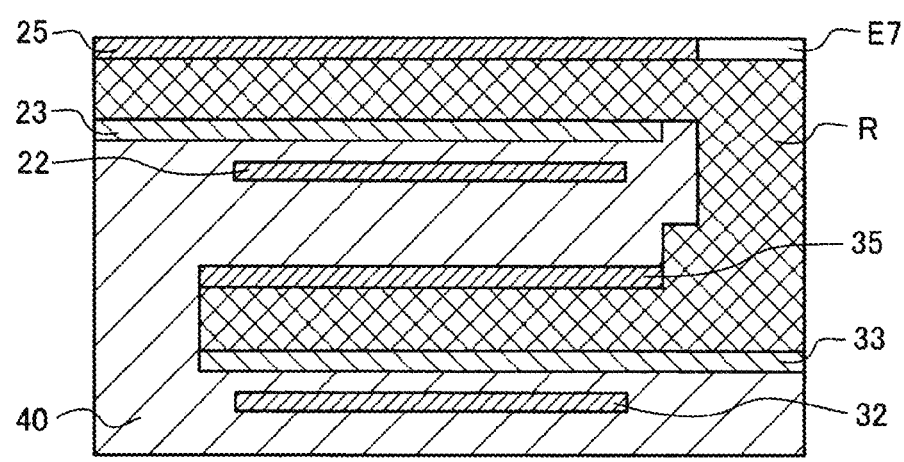
FIG. 18C is a cross-sectional view schematically illustrating a manufacturing step for a pixel array portion according to still another example of Modification Example 3 of the embodiment of the present disclosure.

Next, as illustrated in FIG. 18B, the second electrode 25 is formed to cover the surface of the removal material R. In addition, as illustrated in FIG. 18C, a predetermined region in the second electrode 25 is etched, thereby forming an etching region E7. Meanwhile, such an etching region E7 is provided to expose the removal material R.

Figure 18D:
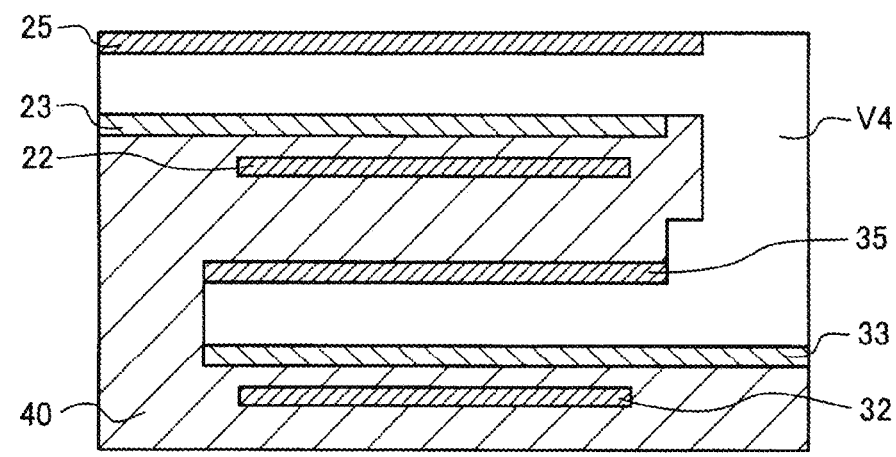
FIG. 18D is a cross-sectional view schematically illustrating a manufacturing step for a pixel array portion according to still another example of Modification Example 3 of the embodiment of the present disclosure.

Next, as illustrated in FIG. 18D, the removal material R is removed by predetermined processing (for example, chemical etching), and a void V4 is formed in a region in which such a removal material R is provided. Further, in Modification Example 3, annealing is performed at a predetermined temperature in a state where the void V4 illustrated in FIG. 18D is formed.

Figure 18E:
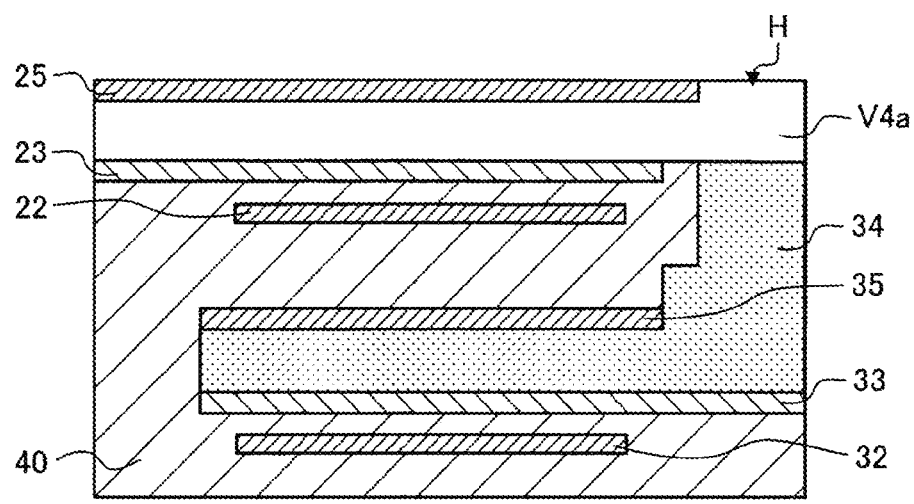
FIG. 18E is a cross-sectional view schematically illustrating a manufacturing step for a pixel array portion according to still another example of Modification Example 3 of the embodiment of the present disclosure.

Next, as illustrated in FIG. 18E, a liquid raw material of the photoelectric conversion layer 34 is injected through an injection port H that opens upward from the void V4 such that the top surface of the charge storage layer 23 and a liquid surface are substantially flush with each other. Then, the photoelectric conversion layer 34 is formed in the void V4 by drying the liquid raw material injected into the void V4 at a predetermined temperature.

Meanwhile, the liquid raw material of the photoelectric conversion layer 34 is injected such that the top surface of the charge storage layer 23 and the liquid surface are substantially flush with each other, and thus a portion of the void V4 remains as a void V4a. Meanwhile, the top surface of the charge storage layer 23 and the top surface of the photoelectric conversion layer 34 may not be substantially flush with each other.

Figure 18F:
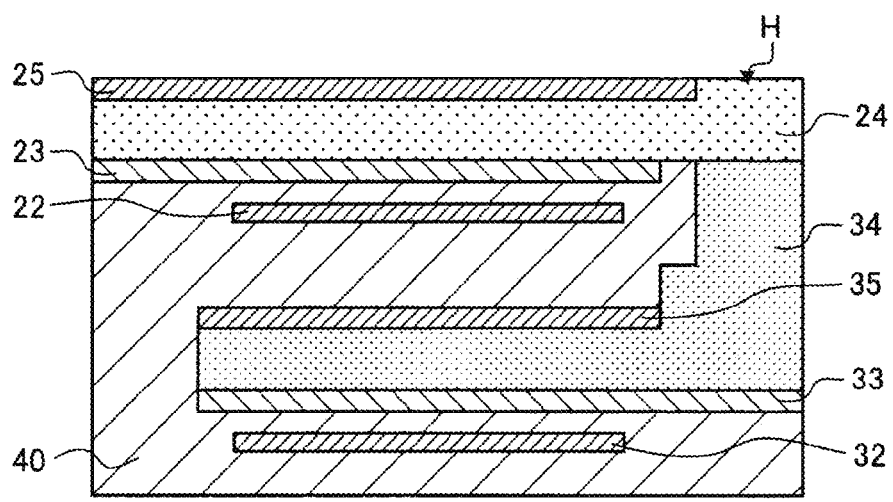
FIG. 18F is a cross-sectional view schematically illustrating a manufacturing step for a pixel array portion according to still another example of Modification Example 3 of the embodiment of the present disclosure.

Next, as illustrated in FIG. 18F, a liquid raw material of the photoelectric conversion layer 24 is injected to fill the void V4a through an injection port H that opens upward from the void V4a. Finally, the photoelectric conversion layer 24 is formed in the void V4a by drying the liquid raw material injected into the void V4a at a predetermined temperature, and thus a manufacturing step for the pixel array portion 10 according to another example of Modification Example 3 of the embodiment is finished.

Manufacturing Step of Modification Example 4

FIGS. 19A, 19B, 19C, 19D, 19E, 19F, 19G, 19H, 19I, 19J, 19K, and 19L are cross-sectional views schematically illustrating a manufacturing step for the pixel array portion 10 according to Modification Example 4 of the embodiment of the present disclosure. Meanwhile, the steps up to the middle in Modification Example 4 are similar to the steps illustrated in FIGS. 14A, 14B, 14C, 14D, 14E, 14F, 14G, 14H, 14I, 14J, 14K, 14L, 14M, 14N, 14O, and 14P and FIGS. 17A, 17B, 17C, and 17D, and thus description thereof will be omitted.

Figure 19A:
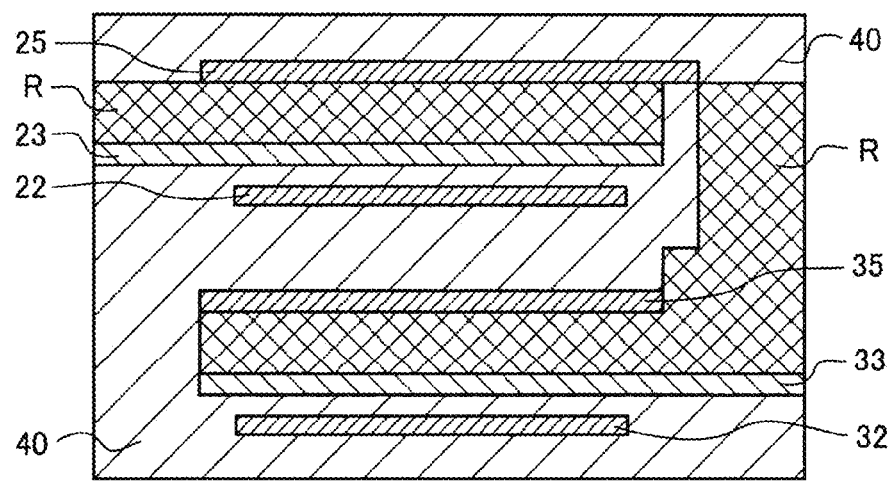
FIG. 19A is a cross-sectional view schematically illustrating a manufacturing step for the pixel array portion according to Modification Example 4 of the embodiment of the present disclosure.
Figure 19B:
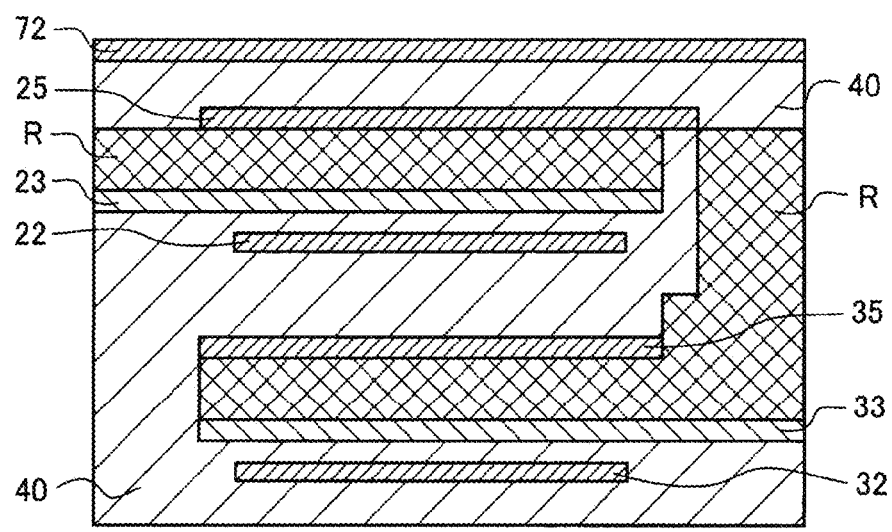
FIG. 19B is a cross-sectional view schematically illustrating a manufacturing step for the pixel array portion according to Modification Example 4 of the embodiment of the present disclosure.

Subsequently to the step illustrated in FIG. 17D, as illustrated in FIG. 19A, the insulating layer 40 is formed to fill in the etching region E6 and cover the surface of the second electrode 35. In addition, as illustrated in FIG. 19B, the charge storage electrode 72 is formed to cover the surface of the insulating layer 40.

Figure 19C:
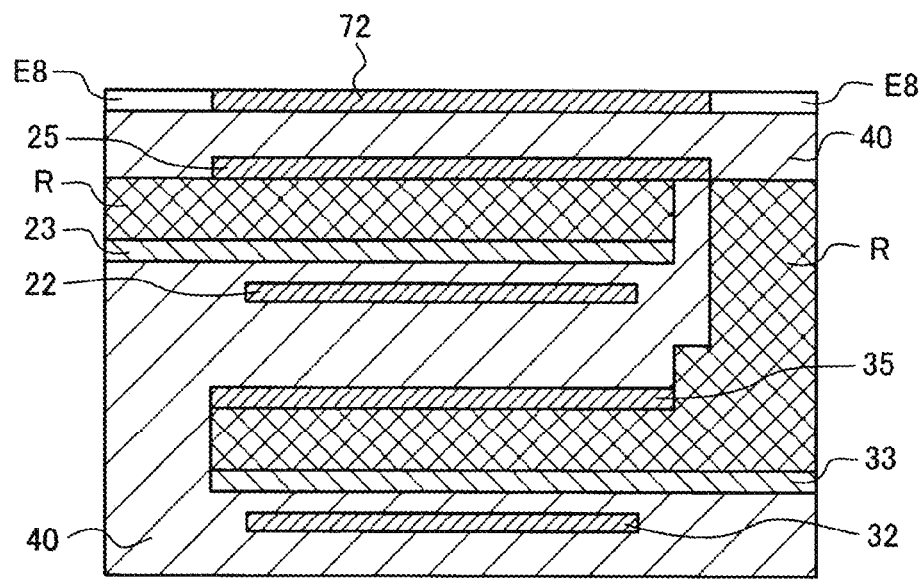
FIG. 19C is a cross-sectional view schematically illustrating a manufacturing step for the pixel array portion according to Modification Example 4 of the embodiment of the present disclosure.
Figure 19D:
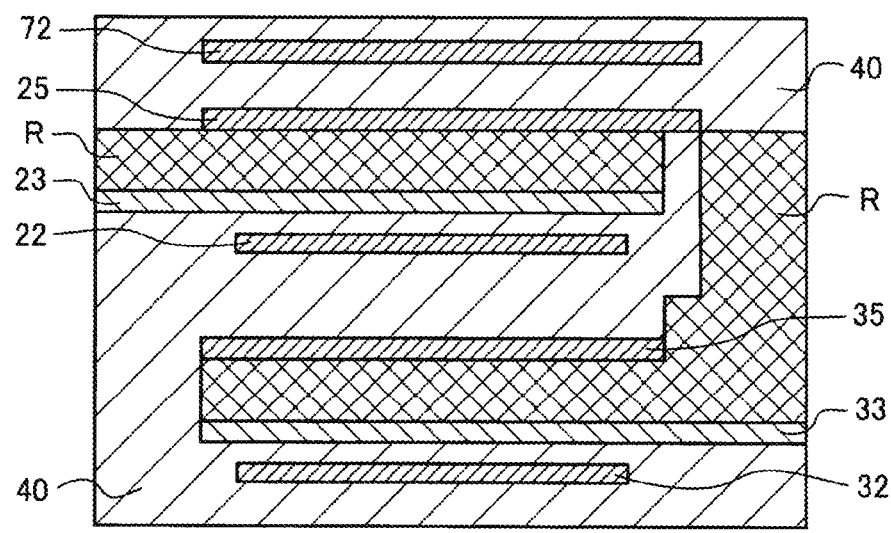
FIG. 19D is a cross-sectional view schematically illustrating a manufacturing step for the pixel array portion according to Modification Example 4 of the embodiment of the present disclosure.

Next, as illustrated in FIG. 19C, a predetermined region in the charge storage electrode 72 is etched by a known method of the related art, thereby forming an etching region E8. In addition, as illustrated in FIG. 19D, the insulating layer 40 is formed to fill in the etching region E8 and cover the surface of the charge storage electrode 72.

Figure 19E:
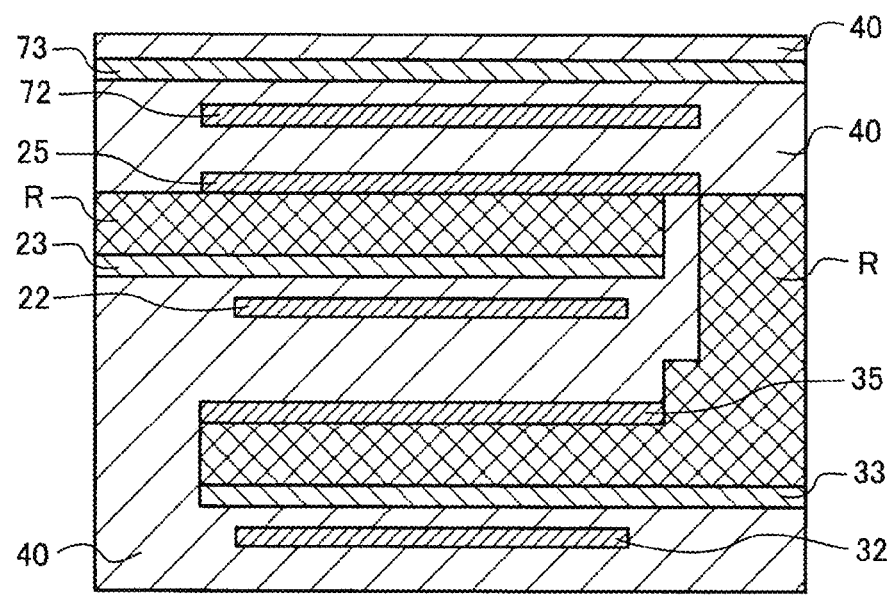
FIG. 19E is a cross-sectional view schematically illustrating a manufacturing step for the pixel array portion according to Modification Example 4 of the embodiment of the present disclosure.

Next, as illustrated in FIG. 19E, the charge storage layer 73 is formed to cover the surface of the insulating layer 40, and the insulating layer 40 is formed to cover the surface of the charge storage layer 73. Meanwhile, in the steps up to FIG. 19E, the first electrode 71 (see FIG. 11) of the photoelectric conversion portion 70 is also formed in parallel, but a process of forming such a first electrode 71 will not be illustrated and described.

Figure 19F:
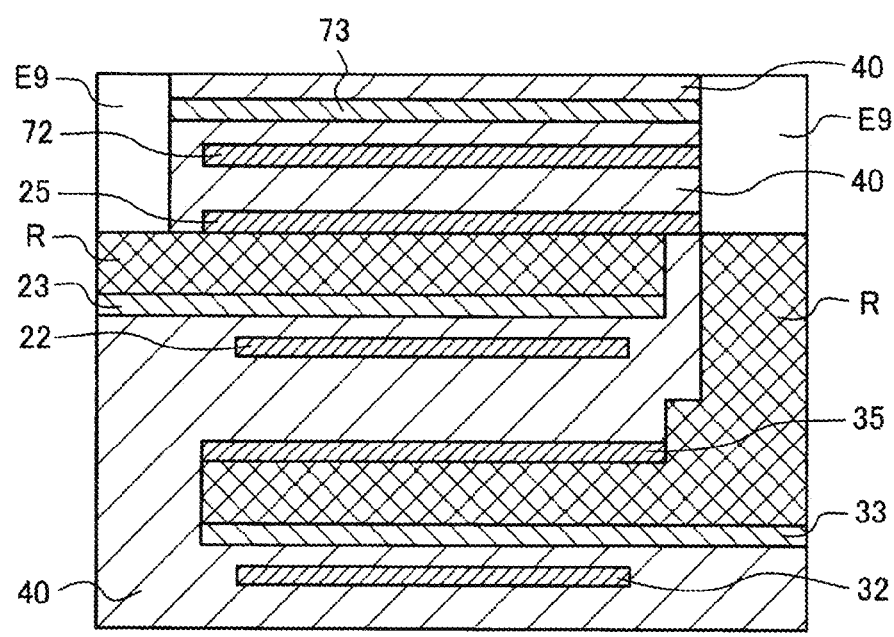
FIG. 19F is a cross-sectional view schematically illustrating a manufacturing step for the pixel array portion according to Modification Example 4 of the embodiment of the present disclosure.

Next, as illustrated in FIG. 19F, predetermined regions in the insulating layer 40 and the charge storage layer 73 are etched by a known method of the related art, thereby forming an etching region E9. Meanwhile, such an etching region E9 is provided to expose the removal material R formed on the surface of the charge storage layer 23 and the removal material R formed on the surface of the charge storage layer 33.

Figure 19G:
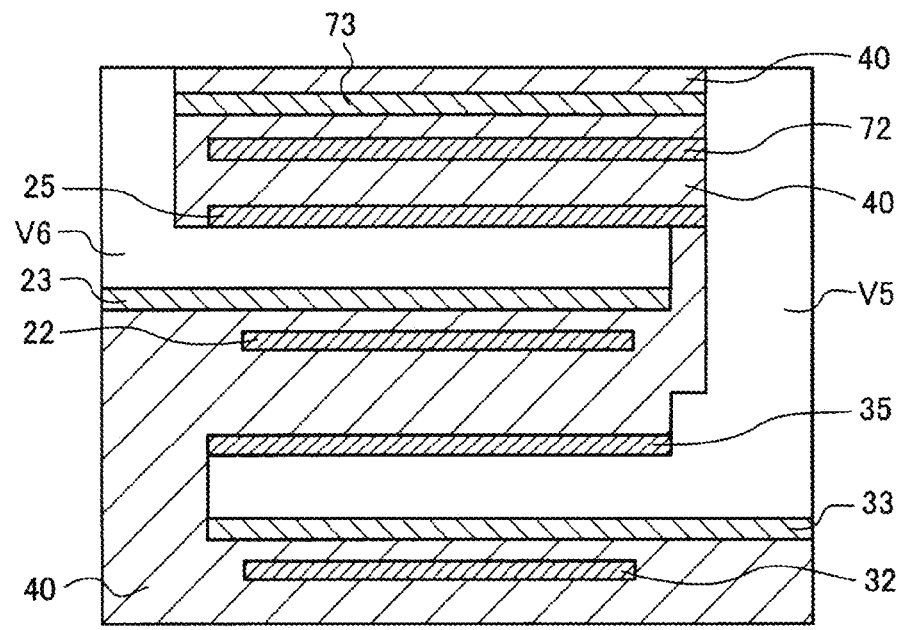
FIG. 19G is a cross-sectional view schematically illustrating a manufacturing step for the pixel array portion according to Modification Example 4 of the embodiment of the present disclosure.

Next, as illustrated in FIG. 19G, the removal material R is removed by predetermined processing (for example, chemical etching), and voids V5 and V6 are formed in a region in which such a removal material R is provided. Meanwhile, the void V5 is a void formed between the charge storage layer 33 and the second electrode 35, and the void V6 is a void formed between the charge storage layer 23 and the second electrode 25.

Further, in Modification Example 4, annealing is performed at a predetermined temperature in a state where the voids V5 and V6 illustrated in FIG. 19G are formed.

Figure 19H:
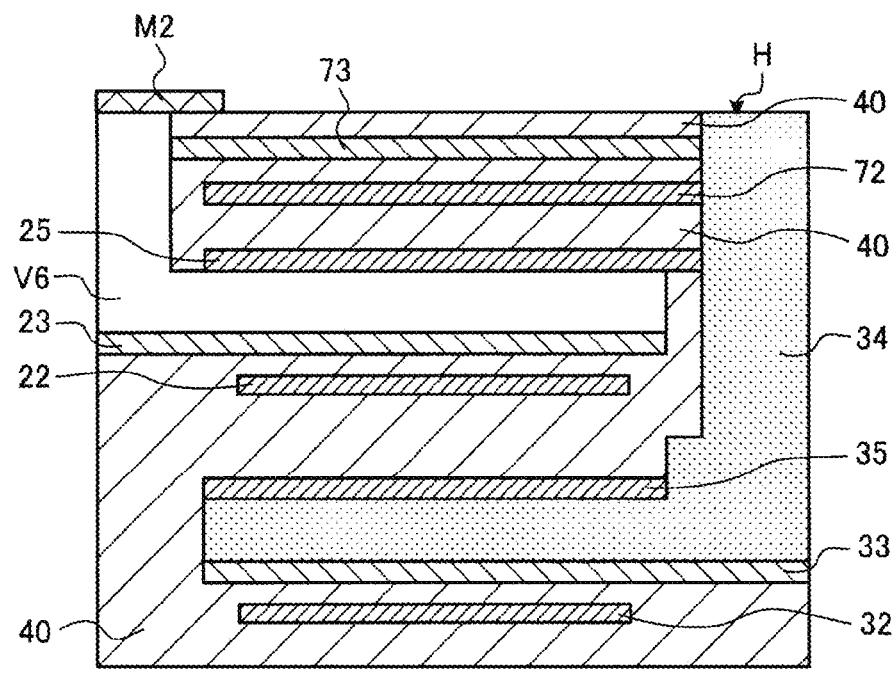
FIG. 19H is a cross-sectional view schematically illustrating a manufacturing step for the pixel array portion according to Modification Example 4 of the embodiment of the present disclosure.

Next, as illustrated in FIG. 19H, a mask M2 is formed to close an opening portion of the void V6. The mask M2, which is, for example, a metal mask, is formed by a known method of the related art. Then, a liquid raw material of the photoelectric conversion layer 34 is injected to fill the void V5 through an injection port H that opens upward from the void V5.

Further, the photoelectric conversion layer 34 is formed in the void V5 by drying the liquid raw material injected into the void V5 at a predetermined temperature.

Figure 19I:
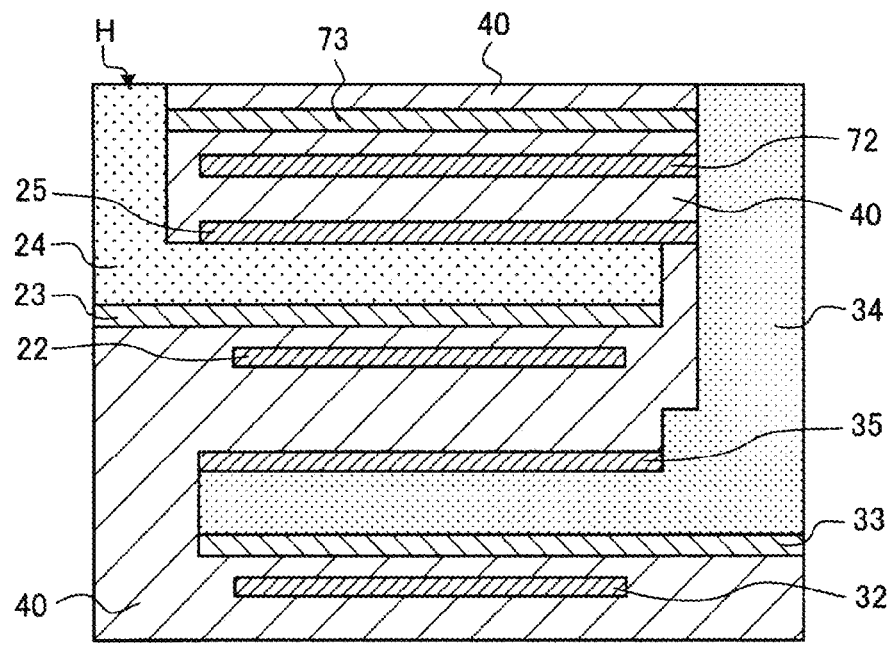
FIG. 19I is a cross-sectional view schematically illustrating a manufacturing step for the pixel array portion according to Modification Example 4 of the embodiment of the present disclosure.

Next, as illustrated in FIG. 19I, the mask M1 is removed by a known method of the related art. Then, a liquid raw material of the photoelectric conversion layer 24 is injected to fill the void V6 through an injection port H that opens upward from the void V6.

Further, the photoelectric conversion layer 24 is formed in the void V6 by drying the liquid raw material injected into the void V6 at a predetermined temperature.

Figure 19J:
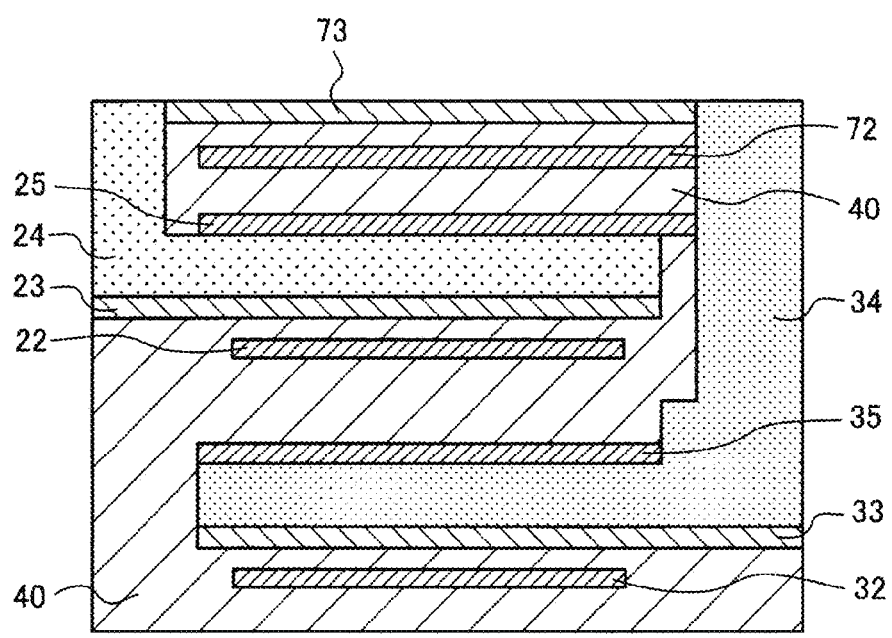
FIG. 19J is a cross-sectional view schematically illustrating a manufacturing step for the pixel array portion according to Modification Example 4 of the embodiment of the present disclosure.

Next, as illustrated in FIG. 19J, the insulating layer 40, the photoelectric conversion layer 24, and the photoelectric conversion layer 34 are removed such that the surface of the charge storage layer 73, the surface of the photoelectric conversion layer 24, and the surface of the photoelectric conversion layer 34 are substantially flush with each other.

Figure 19K:
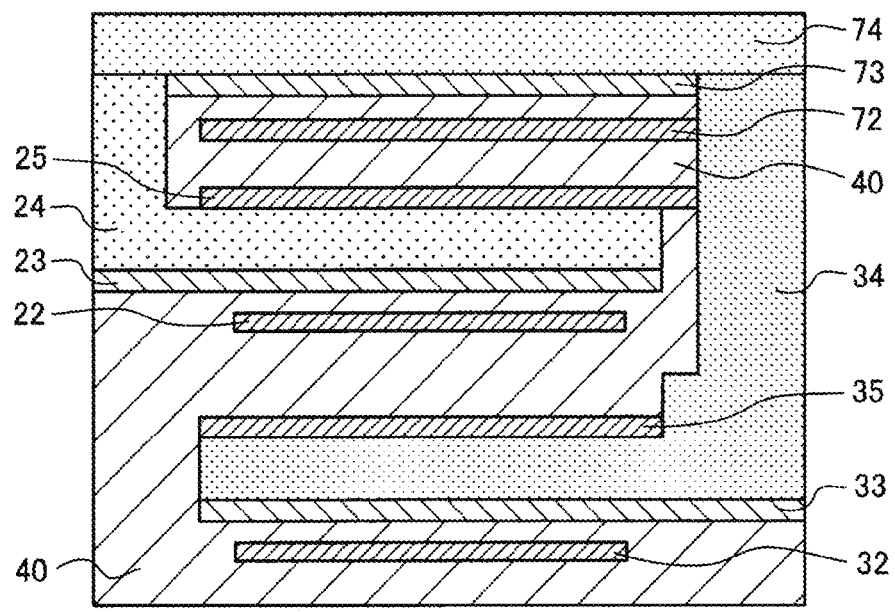
FIG. 19K is a cross-sectional view schematically illustrating a manufacturing step for the pixel array portion according to Modification Example 4 of the embodiment of the present disclosure.

Next, as illustrated in FIG. 19K, the photoelectric conversion layer 74 is formed by a known method of the related art so as to cover the surfaces of the charge storage layer 73, the photoelectric conversion layer 24, and the photoelectric conversion layer 34.

For example, a liquid raw material of the photoelectric conversion layer 74 is applied to the surfaces of the charge storage layer 73, the photoelectric conversion layer 24, and the photoelectric conversion layer 34, and the photoelectric conversion layer 74 is formed by drying such a liquid raw material at a predetermined temperature. Meanwhile, a forming process for the photoelectric conversion layer 74 is not limited to the above-described method, and may be any of other methods such as a vapor growth method.

Figure 19L:
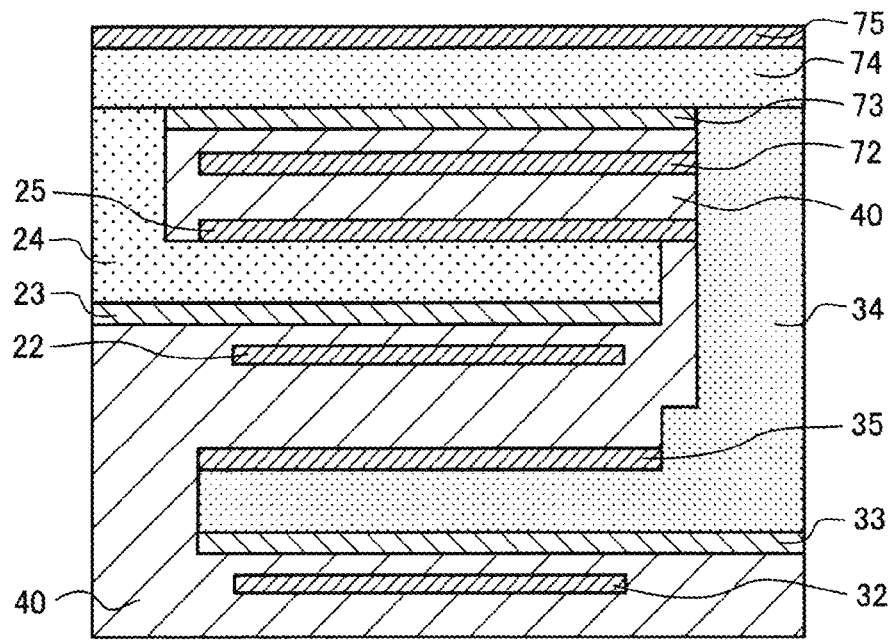
FIG. 19L is a cross-sectional view schematically illustrating a manufacturing step for the pixel array portion according to Modification Example 4 of the embodiment of the present disclosure.

Finally, as illustrated in FIG. 19L, the second electrode 75 is formed by a known method of the related art so as to cover the surface of the photoelectric conversion layer 74, and thus a manufacturing step for the pixel array portion 10 according to the embodiment is finished.

Figure 20:
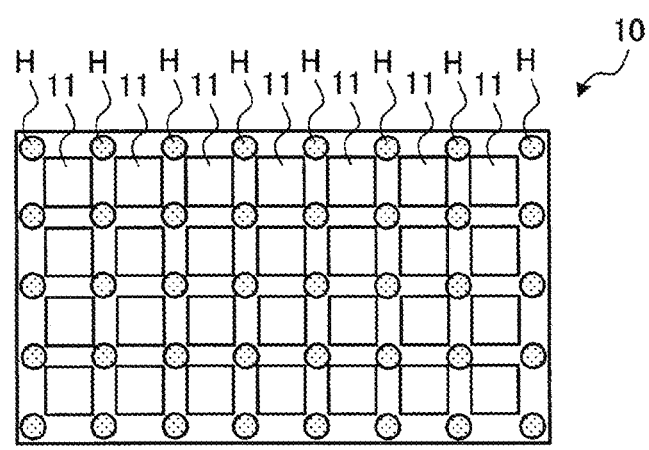
FIG. 20 is a plan view schematically illustrating an example of arrangement of injection ports according to the embodiment of the present disclosure.

FIG. 20 is a plan view schematically illustrating an example of arrangement of injection ports H according to the embodiment of the present disclosure. As illustrated in FIG. 20, in the above-described manufacturing step, the injection port H for injecting a liquid raw material of the photoelectric conversion layer 34 or the like may be provided for each unit pixel 11.

Figure 21:
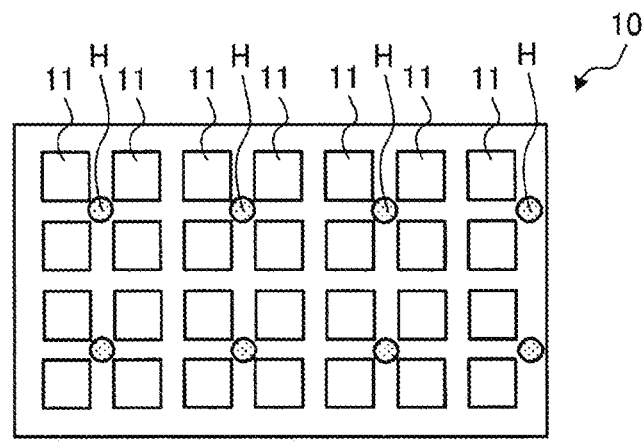
FIG. 21 is a plan view schematically illustrating an example of arrangement of injection ports according to the embodiment of the present disclosure.

FIG. 21 is a plan view schematically illustrating an example of arrangement of injection ports H according to the embodiment of the present disclosure. As illustrated in FIG. 21, each injection port H for injecting a liquid raw material of the photoelectric conversion layer 34 or the like may be provided for a plurality of (four in the example of FIG. 21) unit pixels 11.

Figure 22:
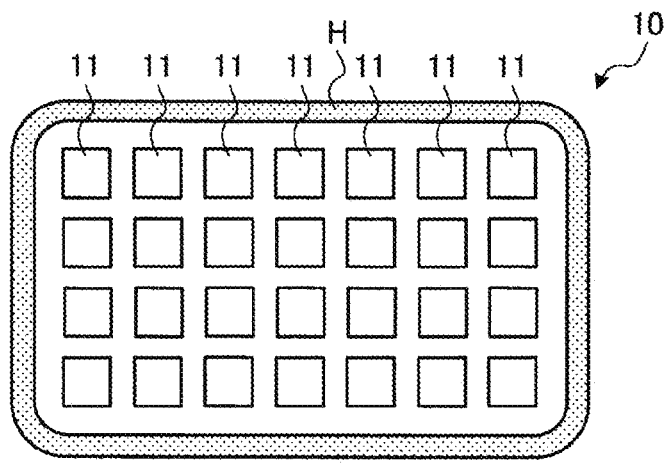
FIG. 22 is a plan view schematically illustrating an example of arrangement of an injection port according to the embodiment of the present disclosure.

FIG. 22 is a plan view schematically illustrating an example of arrangement of an injection port H according to the embodiment of the present disclosure. As illustrated in FIG. 22, the injection port H for injecting a liquid raw material of the photoelectric conversion layer 34 or the like may be provided to surround a pixel group outside the pixel group constituted by a plurality of unit pixels 11 disposed on a matrix.

Processing Procedure of Manufacturing Step

Figure 23:
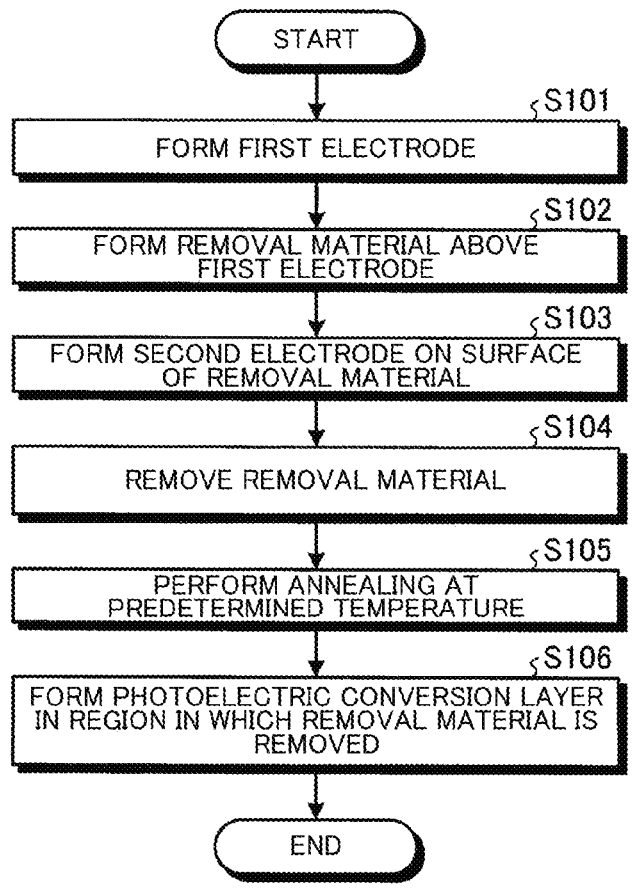
FIG. 23 is a flowchart illustrating a processing procedure of a manufacturing step according to the embodiment.

Subsequently, a processing procedure of a manufacturing step for the pixel array portion 10 according to the embodiment will be described with reference to FIG. 23. FIG. 23 is a flowchart illustrating a processing procedure of a manufacturing step according to the embodiment.

First, the first electrode 31 is formed on the surface of the semiconductor layer 50 in which the photodiode 60, various pixel transistors, various wirings, the floating diffusions 51 to 53, and the like are already formed (step S101). Such a first electrode 31 is electrically connected to the floating diffusion 52 and is surrounded by the insulating layer 40.

Next, the removal material R is formed above the first electrode 31 (step S102). For example, the removal material R is formed on the surface of the charge storage layer 33 which is formed to be in contact with the surface of the first electrode 31. Meanwhile, the removal material R may be directly formed on the surface of the first electrode 31.

Next, the second electrode 35 is formed on the surface of the removal material R (step S103). Meanwhile, a step of forming such a second electrode 35 may be performed not to cover a portion of the removal material R. In other words, the removal material R may be provided such that a portion thereof excludes the second electrode 35 when seen in a plan view.

Next, the removal material R is removed by predetermined processing (for example, chemical etching) (step S104). Thereby, the void V1 is formed on the bottom surface side of the second electrode 35.

Next, annealing is performed at a predetermined temperature in a state where such a void V1 is formed (step S105). Meanwhile, such an annealing step may be performed at a desired temperature higher than a heat-resistant temperature of the photoelectric conversion layer 34 formed in step S106 later.

Thereby, it is possible to form an element having satisfactory characteristics in the pixel array portion 10 and suppress the occurrence of damage in the photoelectric conversion layer 34.

Finally, the photoelectric conversion layer 34 is formed in a region (void V1) in which the removal material R is removed (step S106), and the processing is completed. Meanwhile, a step of forming such a photoelectric conversion layer 34 may be performed by injecting a liquid raw material of the photoelectric conversion layer 34 into the void V1 from the injection port H formed to exclude the second electrode 35.

Thereby, it is possible to form the photoelectric conversion layer 34 after a semiconductor process is finished to a certain degree.

Advantageous Effects

The solid-state imaging device 1 according to the embodiment includes the photoelectric conversion portion 30 including the first electrode 31, the photoelectric conversion layer 34 electrically connected to the first electrode 31, and the second electrode 35 provided on a surface on a light incidence side of the photoelectric conversion layer 34. In addition, the photoelectric conversion layer 34 includes a protrusion region 34a that protrudes from the second electrode 35 when seen in a plan view.

Thereby, it is possible to realize the solid-state imaging device 1 in which a satisfactory photoelectric conversion layer 34 is formed.

Further, in the solid-state imaging device 1 according to the embodiment, the photoelectric conversion portion 30 further includes the charge storage layer 33 provided on a surface on a side opposite to the light incidence side in the photoelectric conversion layer 34, and the charge storage electrode 32 disposed to face the charge storage layer 33 through the insulating layer 40.

Thereby, it is possible to reduce reset noise due to the reset transistor 62R during a reset operation, and thus a high-quality image can be acquired.

Further, in the solid-state imaging device 1 according to the embodiment, a plurality of photoelectric conversion portions 30 are provided. In addition, the plurality of photoelectric conversion portions 30 share one floating diffusion 52.

Thereby, it is not necessary to provide individual floating diffusion 52 in all of the photoelectric conversion portions 30, and thus it is possible to simplify a circuit configuration inside the pixel array portion 10.

Further, in the solid-state imaging device 1 according to the embodiment, the protrusion region 34a of the photoelectric conversion layer 34 is configured such that a portion of the photoelectric conversion layer 34 which is in contact with the second electrode 35 and a surface on the light incidence side are substantially flush with each other.

Thereby, the photoelectric conversion layer 34 can be formed after a semiconductor process is finished to a certain degree.

Further, in the solid-state imaging device 1 according to the embodiment, the protrusion region 34a of the photoelectric conversion layer 34 is configured such that a surface on the light incidence side protrudes from a portion of the photoelectric conversion layer 34 which is in contact with the second electrode 35.

Thereby, the photoelectric conversion layer 34 can be formed after a semiconductor process is finished to a certain degree.

Further, in the solid-state imaging device 1 according to the embodiment, the photoelectric conversion layer 34 of the photoelectric conversion portion 30 is constituted by an organic semiconductor material.

Thereby, attenuation of light L can be suppressed by the photoelectric conversion portion 30, and thus it is possible to acquire a high-quality image.

In addition, the solid-state imaging device 1 according to the embodiment further includes another photoelectric conversion portion 20 which is provided on the light incidence side of the photoelectric conversion portion 30 and performs photoelectric conversion of light having a wavelength different from that of the photoelectric conversion portion 30.

Thereby, attenuation of light L incident by such a color filter can be suppressed, and thus it is possible to acquire a high-quality image.

Further, in the solid-state imaging device 1 according to the embodiment, the photoelectric conversion layer 24 of the other photoelectric conversion portion 20 is constituted by an organic semiconductor material.

Thereby, attenuation of light L can be suppressed by the photoelectric conversion portion 20, and thus it is possible to acquire a high-quality image.

In addition, a method of manufacturing the solid-state imaging device 1 according to the embodiment includes a step of forming the first electrode 31, a step of forming the removal material R, a step of forming the second electrode 35, a step of removing the removal material E, and a step of forming the photoelectric conversion layer 34. In the step of forming the removal material R, the removal material R is formed above the first electrode 31. In the step of forming the second electrode 35, the second electrode 35 is formed on the surface of the removal material R. In the step of forming the photoelectric conversion layer 34, the photoelectric conversion layer 34 is formed in a region in which the removal material R is removed.

Thereby, it is possible to realize the solid-state imaging device 1 in which a satisfactory photoelectric conversion layer 34 is formed.

In addition, the method of manufacturing the solid-state imaging device 1 according to the embodiment includes a step of performing annealing at a predetermined temperature before the step of forming the photoelectric conversion layer 34.

Thereby, it is possible to form an element having satisfactory characteristics in the pixel array portion 10.

Further, in the method of manufacturing the solid-state imaging device 1 according to the embodiment, annealing is performed at a temperature higher than a heat-resistant temperature of the photoelectric conversion layer 34 in the annealing step.

Thereby, it is possible to form an element having satisfactory characteristics in the pixel array portion 10 and suppress the occurrence of damage in the photoelectric conversion layer 34.

Further, in the method of manufacturing the solid-state imaging device 1 according to the embodiment, the step of forming the photoelectric conversion layer 34 is performed by injecting a liquid raw material into a region in which the removal material R is removed from the injection port H formed to exclude the second electrode 35.

Thereby, the photoelectric conversion layer 34 can be formed after a semiconductor process is finished to a certain degree.

Electronic Equipment

Meanwhile, the present disclosure is not limited to application to a solid-state imaging device. That is, the present disclosure can be applied to all kinds of electronic equipment including a solid-state imaging device, such as a camera module, an imaging device, a portable terminal device having an imaging function, or a copy machine using a solid-state imaging device for an image reading unit, in addition to a solid-state imaging device.

Examples of such an imaging device include a digital still camera, a video camera, and the like. In addition, examples of such a portable terminal device having an imaging function include a smartphone, a tablet terminal, and the like.

Figure 24:
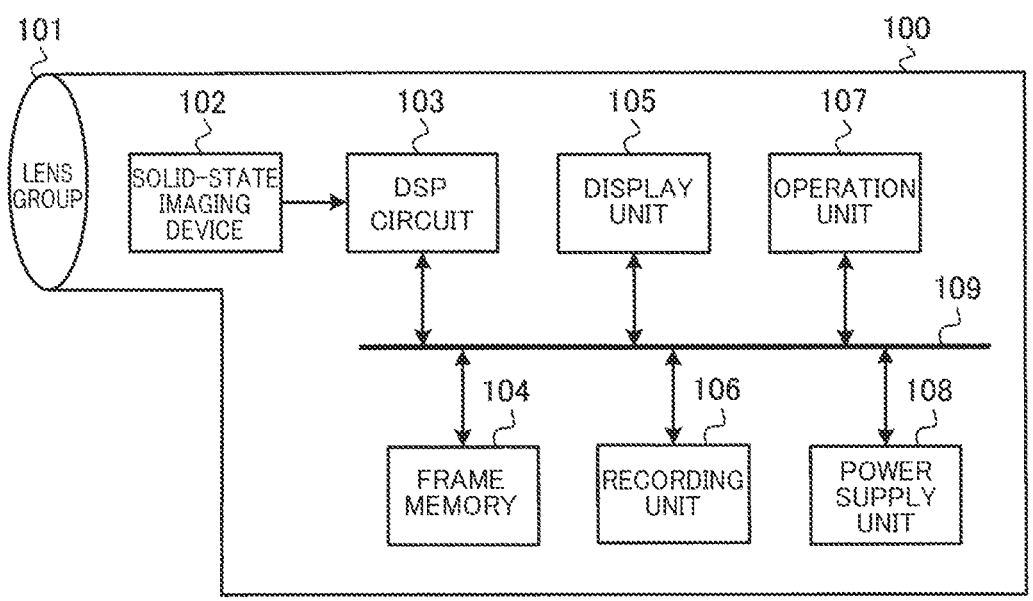
FIG. 24 is a block diagram illustrating a configuration example of an imaging device as electronic equipment to which the present disclosure is applied.

FIG. 24 is a block diagram illustrating a configuration example of an imaging device as an electronic equipment 100 to which the technology according to the present disclosure is applied. The electronic equipment 100 in FIG. 24 is electronic equipment, for example, an imaging device such as a digital still camera or a video camera, or a portable terminal device such as a smartphone or a tablet terminal.

In FIG. 24, the electronic equipment 100 includes a lens group 101, a solid-state imaging device 102, a DSP circuit 103, a frame memory 104, a display unit 105, a recording unit 106, an operation unit 107, and a power supply unit 108.

Further, in the electronic equipment 100, the DSP circuit 103, the frame memory 104, the display unit 105, the recording unit 106, the operation unit 107, and the power supply unit 108 are connected to each other through a bus line 109.

The lens group 101 captures incident light (image light) from a subject and forms an image on an imaging surface of the solid-state imaging device 102. The solid-state imaging device 102 corresponding to the solid-state imaging device 1 according to the above-described embodiment converts the amount of incident light imaged on the imaging surface by the lens group 101 into an electrical signal in pixel units, and outputs the electrical signal as a pixel signal.

The DSP circuit 103 is a camera signal processing circuit that processes a signal supplied from the solid-state imaging device 102. The frame memory 104 temporarily holds image data processed by the DSP circuit 103 in frame units.

The display unit 105 is constituted by a panel type display device such as a liquid crystal panel or an organic electro luminescence (EL) panel, and displays a moving image or a still image captured by the solid-state imaging device 102. The recording unit 106 records image data of a moving image or a still image captured by the solid-state imaging device 102 in a recording medium such as a semiconductor memory or a hard disk.

The operation unit 107 issues an operation command for various functions of the electronic equipment 100 in response to a user's operation. The power supply unit 108 appropriately supplies various power supplies serving as operation power supplies for the DSP circuit 103, the frame memory 104, the display unit 105, the recording unit 106, and the operation unit 107 to these supply targets.

In the electronic equipment 100 configured in this manner, it is possible to suppress the occurrence of color mixing by applying the solid-state imaging devices 1 of the above-described embodiments as the solid-state imaging device 102.

Application Example to Moving Body

The technology of the present disclosure (the present technology) can be applied in various products. For example, the technology of the present disclosure may be realized as a device mounted on any type of moving body such as an automobile, an electric automobile, a hybrid electric automobile, a motorcycle, a bicycle, a personal mobility, an airplane, a drone, a ship, and a robot.

Figure 25:
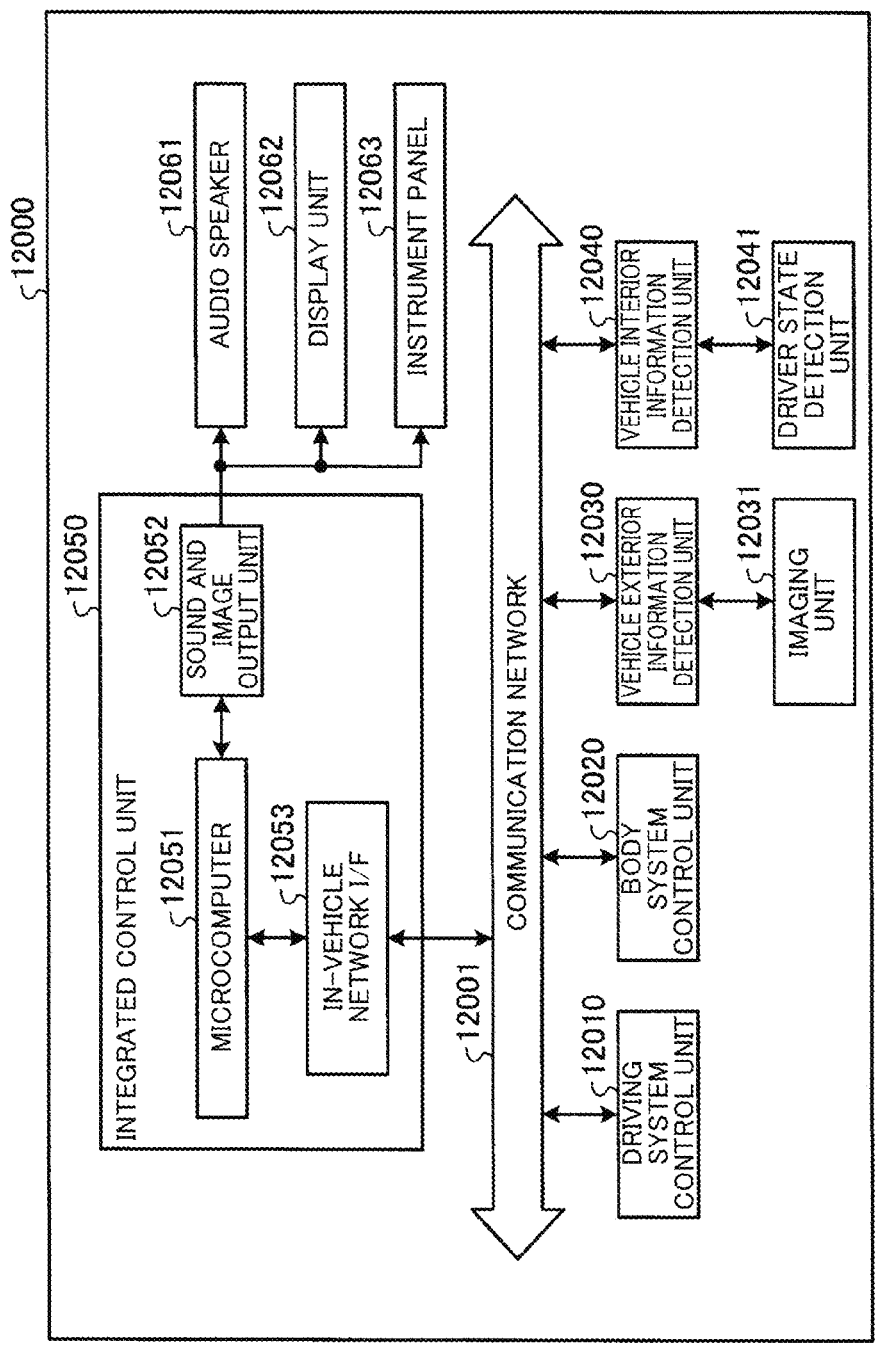
FIG. 25 is a block diagram illustrating an example of a schematic configuration of a vehicle control system.

FIG. 25 is a block diagram illustrating an example of an overall configuration of a vehicle control system which is an example of a moving object control system to which the technology of the present disclosure can be applied.

A vehicle control system 12000 includes a plurality of electronic control units connected to each other through a communication network 12001. In the example illustrated in FIG. 25, the vehicle control system 12000 includes a driving system control unit 12010, a body system control unit 12020, a vehicle exterior information detection unit 12030, a vehicle interior information detection unit 12040, and an integrated control unit 12050. In addition, as a functional configuration of the integrated control unit 12050, a microcomputer 12051, a sound and image output unit 12052, and an in-vehicle network interface (I/F) 12053 are illustrated.

The driving system control unit 12010 controls an operation of a device related to a driving system of a vehicle in accordance with various programs. For example, the driving system control unit 12010 functions as a control device such as a driving force generation device that generates a driving force of a vehicle, such as an internal combustion engine or a driving motor, a driving force transmission mechanism that transmits a driving force to wheels, a steering mechanism that adjusts a rudder angle of the vehicle, and a braking device that generates a braking force of the vehicle.

The body system control unit 12020 controls operations of various devices equipped in a vehicle body in accordance with various programs. For example, the body system control unit 12020 functions as a keyless entry system, a smart key system, a power window device, or a control device of various lamps such as a head lamp, a back lamp, a brake lamp, a turn signal, and a fog lamp. In this case, radio waves transmitted from a portable device with which a key is substituted or signals of various switches may be input to the body system control unit 12020. The body system control unit 12020 receives an input of the radio waves or the signals and controls a door locking device, a power window device, lamps, and the like of the vehicle.

The vehicle exterior information detection unit 12030 detects external information of the vehicle on which the vehicle control system 12000 is mounted. For example, the imaging unit 12031 is connected to the vehicle exterior information detection unit 12030. The vehicle exterior information detection unit 12030 causes the imaging unit 12031 to capture vehicle exterior images and receives the captured images. Based on the received images, the vehicle exterior information detection unit 12030 may perform an object detection process or a distance detection process for people, vehicles, obstacles, signs, letters on road surfaces, and the like.

The imaging unit 12031 is an optical sensor that receives light and outputs an electric signal in accordance with an amount of received light. The imaging unit 12031 can output the electric signal as an image or can also output the electric signal as distance measurement information. The light received by the imaging unit 12031 may be visible light or may be invisible light such as infrared light.

The vehicle interior information detection unit 12040 detects vehicle interior information. For example, a driver state detection unit 12041 that detects a driver state is connected to the vehicle interior information detection unit 12040. The driver state detection unit 12041 includes, for example, a camera that images a driver. Based on detection information input from the driver state detection unit 12041, the vehicle interior information detection unit 12040 may calculate a fatigue degree or a concentration degree of the driver or may determine whether the driver is dozing.

The microcomputer 12051 can calculate a control target value of the driving force generation device, the steering mechanism, or the braking device based on information regarding the vehicle exterior and interior acquired by the vehicle exterior information detection unit 12030 or the vehicle interior information detection unit 12040, and can output a control instruction to the driving system control unit 12010. For example, the microcomputer 12051 can perform coordinated control for realizing an ADAS (advanced driver assistance system) function including vehicle collision avoidance, shock alleviation, following travel based on an inter-vehicle distance, vehicle speed maintenance travel, a vehicle collision warning, or a vehicle lane deviation warning.

The microcomputer 12051 can perform coordinated control for automated driving or the like in which autonomous travel is performed without an operation of a driver by controlling the driving force generation device, the steering mechanism, the braking device, and the like based on information regarding the vicinity of the vehicle acquired by the vehicle exterior information detection unit 12030 or the vehicle interior information detection unit 12040.

The microcomputer 12051 can output a control instruction to the body system control unit 12020 based on information regarding the vehicle exterior acquired by the vehicle exterior information detection unit 12030. For example, the microcomputer 12051 can perform coordinated control for achieving antidazzle such as switching of a high beam to a low beam by controlling the head lamp in accordance with a position of a front vehicle or an oncoming vehicle detected by the vehicle exterior information detection unit 12030.

The sound and image output unit 12052 transmits an output signal of at least one of a sound and an image to an output device capable of notifying an occupant of the vehicle or the vehicle exterior of information visually or auditorily. In the example of FIG. 25, an audio speaker 12061, a display unit 12062, and an instrument panel 12063 are exemplified as the output device. The display unit 12062 may include for example, at least one of an onboard display and a head-up display.

Figure 26:
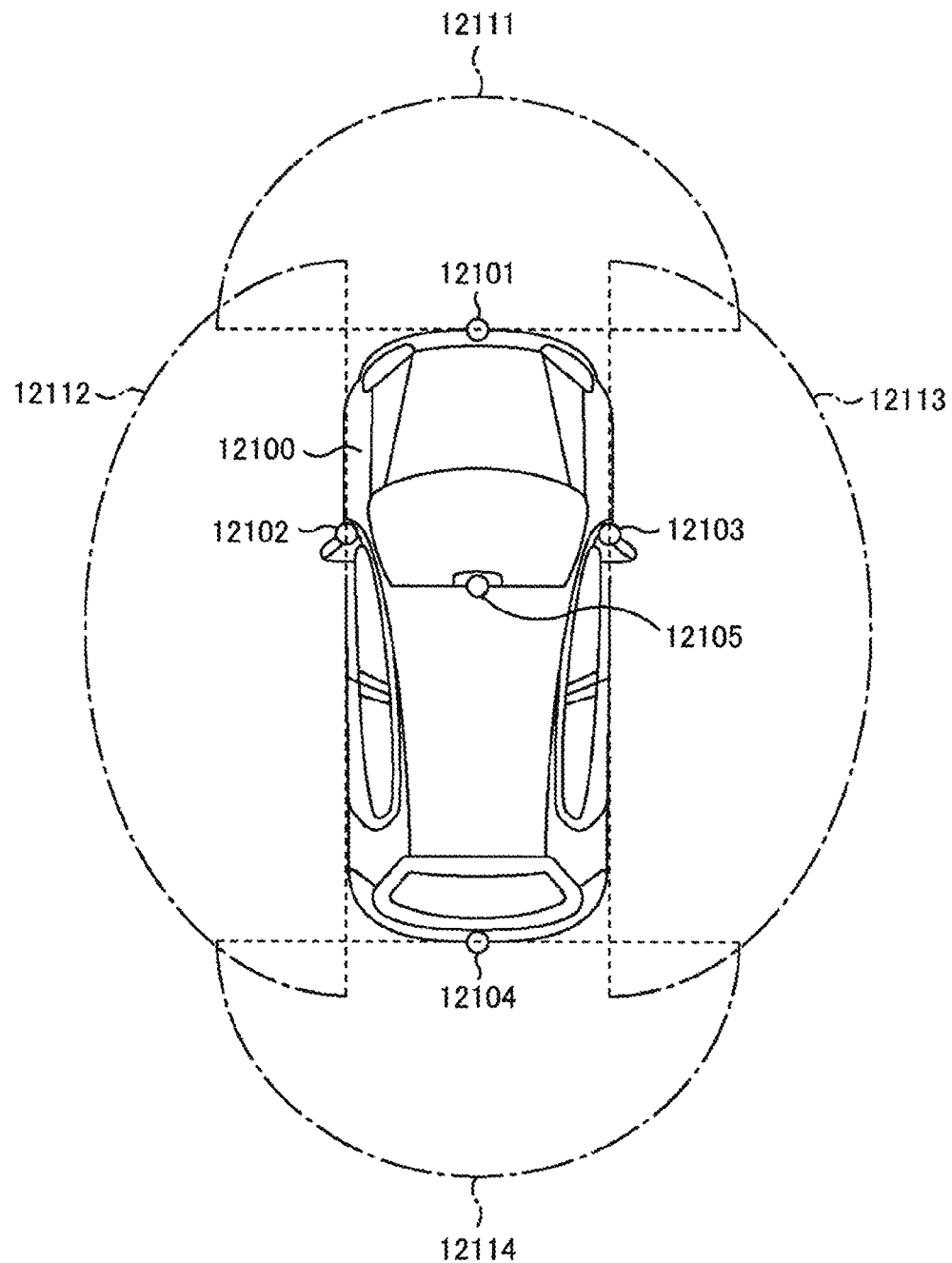
FIG. 26 is a diagram illustrating an example of installation positions of a vehicle exterior information detection unit and an imaging unit.

FIG. 26 is a diagram illustrating an example of positions at which the imaging unit 12031 is installed.

In FIG. 26, imaging units 12101, 12102, 12103, 12104, and 12105 are included as the imaging unit 12031.

The imaging units 12101, 12102, 12103, 12104, and 12105 are provided, for example, at positions such as a front nose, side mirrors, a rear bumper, a backdoor, and an upper portion of a front glass of the vehicle interior of the vehicle 12100. The imaging unit 12101 provided in the front nose and the imaging unit 12105 provided in the upper portion of the front glass inside the vehicle mainly acquire images on the front side of the vehicle 12100. The imaging units 12102 and 12103 provided in the side mirrors mainly acquire images on the lateral sides of the vehicle 12100. The imaging unit 12104 provided in the rear bumper or the backdoor mainly acquires images on the rear side of the vehicle 12100. The imaging unit 12105 included in the upper portion of the front glass inside the vehicle is mainly used to detect front vehicles or pedestrians, obstacles, traffic signals, traffic signs, lanes, and the like.

Meanwhile, FIG. 26 illustrates an example of imaging ranges of the imaging units 12101 to 12104. An imaging range 12111 is an imaging range of the imaging unit 12101 provided in the front nose, imaging ranges 12112 and 12113 are imaging ranges of the imaging unit 12102 and 12103 provided in the side mirrors, and an imaging range 12114 is an imaging range of the imaging unit 12104 provided in the rear bumper or the backdoor. For example, by superimposing the image data captured by the imaging units 12101 to 12104, it is possible to obtain a bird's eye view image in which the vehicle 12100 is viewed from the upper side.

At least one of the imaging units 12101 to 12104 may have a function of acquiring distance information. For example, at least one of the imaging units 12101 to 12104 may be a stereo camera including a plurality of imaging elements or may be an imaging element that has pixels for phase difference detection.

For example, the microcomputer 12051 can extract a three-dimensional object traveling at a predetermined speed (for example, 0 km/h or more) in substantially the same direction as that of the vehicle 12100 which is particularly a closest three-dimensional object on a travel road of the vehicle 12100 as a front vehicle by obtaining a distance from each three-dimensional object within the imaging ranges 12111 to 12114 and a temporal change of the distance (a relative speed to the vehicle 12100) based on the distance information obtained from the imaging units 12101 to 12104. Further, the microcomputer 12051 can set an inter-vehicle distance which is guaranteed in advance before a front vehicle and perform automated brake control (also including following stop control) or automated acceleration control (also including following start control). In this way, it is possible to perform the coordinated control for automated driving or the like in which autonomous travel is performed without an operation of a driver.

For example, the microcomputer 12051 can classify and extract three-dimensional object data regarding three-dimensional objects into motorcycles, normal vehicles, large vehicles, pedestrians, and other three-dimensional objects such as electric poles based on the distance information obtained from the imaging units 12101 to 12104, and can use the three-dimensional object data for automatic avoidance of obstacles. For example, the microcomputer 12051 identifies obstacles around the vehicle 12100 as obstacles which can be recognized by the driver of the vehicle 12100 and obstacles which it is difficult to recognize. Then, the microcomputer 12051 determines a collision risk indicating a risk of collision with each obstacle. In a situation in which there is a possibility of collision at which the collision risk is equal to or greater than a set value, driving support for collision avoidance can be performed by outputting a warning to the driver via the audio speaker 12061 or the display unit 12062 or performing forced deceleration or avoidance steering via the driving system control unit 12010.

At least one of the imaging units 12101 to 12104 may be an infrared camera that detects infrared light. For example, the microcomputer 12051 can recognize pedestrians by determining whether there are the pedestrians in images captured by the imaging units 12101 to 12104. The pedestrians are recognized, for example, in an order in which feature points in the images captured by the imaging units 12101 to 12104 serving as infrared cameras are extracted and an order in which a pattern matching process is performed on a series of feature points indicating the contour of an object to determine whether there is a pedestrian. When the microcomputer 12051 determines that there is the pedestrian in the images captured by the imaging units 12101 to 12104 and recognizes the pedestrian, the sound and image output unit 12052 controls the display unit 12062 such that a rectangular contour line for emphasizing the recognized pedestrian is superimposed and displayed. The sound and image output unit 12052 may control the display unit 12062 such that an icon or the like indicating the pedestrian is displayed at a desired position.

The example of the vehicle control system to which the technology according to the present disclosure is applied has been described above. The technology of the present disclosure can be applied to the imaging unit 12031 and the like in the above-described configuration. Specifically, the solid-state imaging device 1 in FIG. 1 can be applied to the imaging unit 12031. By applying the technology according to the present disclosure to the imaging unit 12031, it is possible to acquire a high-quality image from the imaging unit 12031.

Application Example to Endoscopic Surgery System

The technology of the present disclosure (the present technology) can be applied in various products. For example, the technology according to the present disclosure may be applied to an endoscopic surgery system.

Figure 27:
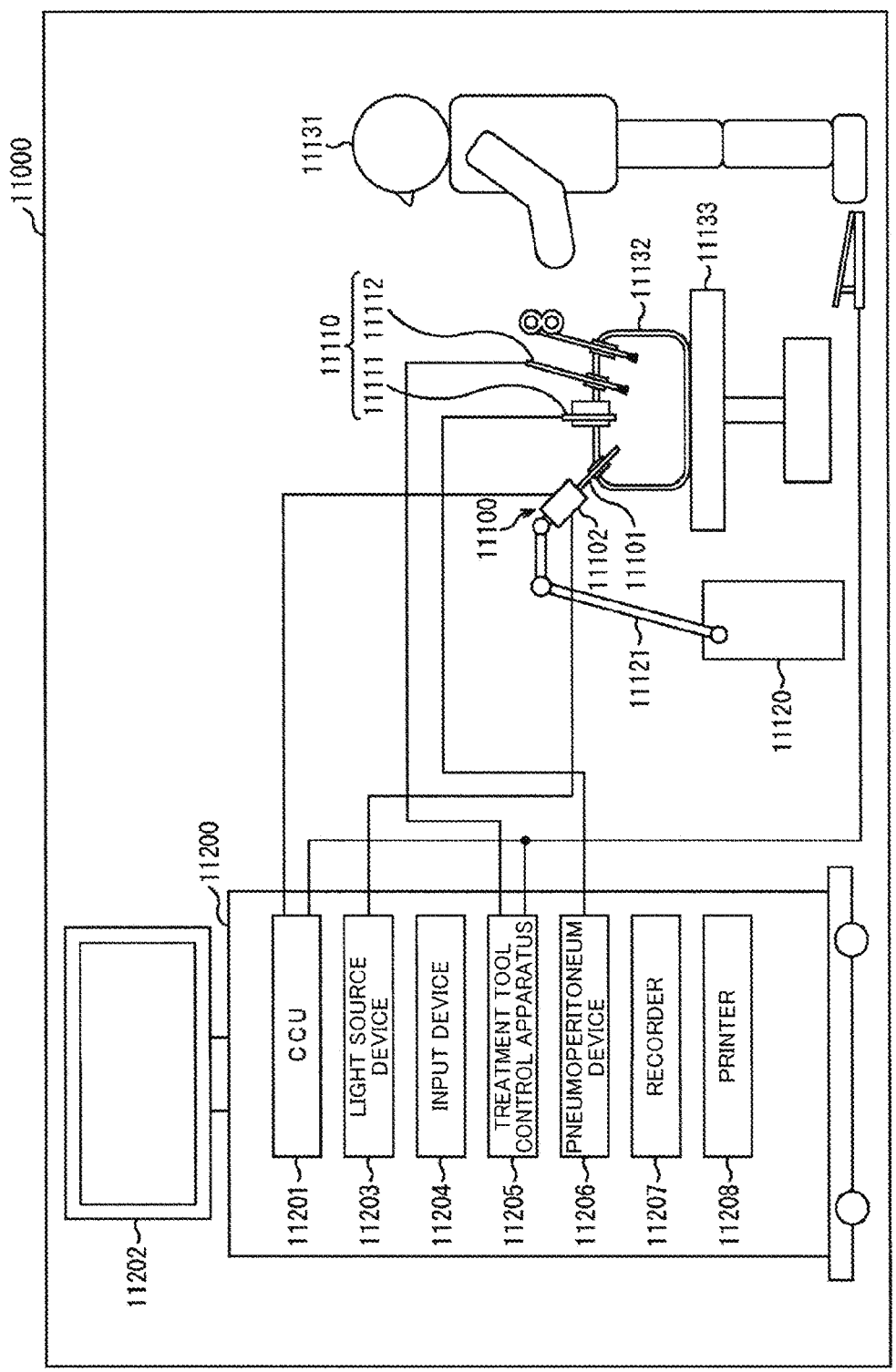
FIG. 27 is a diagram illustrating an example of a schematic configuration of an endoscopic surgery system.

FIG. 27 is a diagram illustrating an example of a schematic configuration of an endoscopic surgery system to which the technology according to the present disclosure (the present technology) can be applied.

FIG. 27 illustrates a state in which an operator (doctor) 11131 is performing surgery on a patient 11132 on a patient bed 11133 using the endoscopic surgery system 11000. As illustrated, the endoscopic surgery system 11000 includes an endoscope 11100, other surgical instruments 11110 such as a pneumoperitoneum tube 11111 and an energized treatment tool 11112, a support arm device 11120 that supports the endoscope 11100, and a cart 11200 equipped with various devices for endoscopic surgery.

The endoscope 11100 includes a lens barrel 11101 of which a region having a predetermined length from a distal end is inserted into a body cavity of the patient 11132, and a camera head 11102 connected to a base end of the lens barrel 11101. Although the endoscope 11100 configured as a so-called rigid mirror having the rigid lens barrel 11101 is illustrated in the illustrated example, the endoscope 11100 may be configured as a so-called flexible mirror having a flexible lens barrel.

An opening in which an objective lens is fitted is provided at a distal end of the lens barrel 11101. A light source device 11203 is connected to the endoscope 11100, and light generated by the light source device 11203 is guided to the distal end of the lens barrel by a light guide extending inside the lens barrel 11101 and is radiated toward the observation target in the body cavity of the patient 11132 via the objective lens. The endoscope 11100 may be a direct-viewing endoscope or may be a perspective endoscope or a side-viewing endoscope.

An optical system and an imaging element are provided inside the camera head 11102, and the reflected light (observation light) from the observation target is condensed on the imaging element by the optical system. The observation light is photoelectrically converted by the imaging element, and an electrical signal corresponding to the observation light, that is, an image signal corresponding to an observation image is generated. The image signal is transmitted to a camera control unit (CCU) 11201 as RAW data.

The CCU 11201 is constituted by a central processing unit (CPU), a graphics processing unit (GPU), or the like, and generally controls operations of the endoscope 11100 and the display device 11202. Further, the CCU 11201 receives an image signal from the camera head 11102, and performs, on the image signal, various image processing such as a development process (demosaic processing) for displaying an image based on the image signal.

The display device 11202 displays an image based on the image signal subjected to the image processing by the CCU 11201 under the control of the CCU 11201.

The light source device 11203 is constituted by a light source such as a light emitting diode (LED), and supplies irradiation light used at the time of imaging a surgical site or the like to the endoscope 11100.

An input device 11204 is an input interface for the endoscopic surgery system 11000. The user can input various types of information or instructions to the endoscopic surgery system 11000 via the input device 11204. For example, the user inputs an instruction to change imaging conditions (a type of irradiation light, a magnification, a focal length, or the like) of the endoscope 11100.

A treatment tool control apparatus 11205 controls drive of the energized treatment tool 11112 for cauterizing or incising tissue, sealing a blood vessel, or the like. A pneumoperitoneum device 11206 sends gas into the body cavity through a pneumoperitoneum tube 11111 in order to inflate the body cavity of the patient 11132 for the purpose of securing a visual field for the endoscope 11100 and a working space for the operator. A recorder 11207 is a device capable of recording various information regarding surgery. A printer 11208 is a device that can print various types of information regarding surgery in various formats such as text, images, or graphs.

The light source device 11203 that supplies the endoscope 11100 with the irradiation light for imaging the surgical part can be configured of, for example, an LED, a laser light source, or a white light source configured of a combination thereof. When a white light source is formed by a combination of RGB laser light sources, it is possible to control an output intensity and an output timing of each color (each wavelength) with high accuracy and thus, the light source device 11203 adjusts white balance of the captured image. Further, in this case, the observation target is time-divisionally irradiated with laser light from the respective RGB laser light sources, and driving of the imaging element of the camera head 11102 is controlled in synchronization with the irradiation timing, such that images corresponding to respective RGB can be captured in a time division manner. According to this method, it is possible to obtain a color image without providing a color filter to the imaging element.

Further, the driving of the light source device 11203 may be controlled to change the intensity of the output light at predetermined time intervals. It is possible to acquire images in a time-division manner by controlling the driving of the imaging element of the camera head 11102 in synchronization with a timing at which the intensity of the light is changed, and it is possible to generate a high dynamic range image without so-called blackout and whiteout by combining the images.

Further, the light source device 11203 may be configured to be able to supply light in a predetermined wavelength band corresponding to special light observation. In the special light observation, for example, a so-called narrow band light observation (narrow band imaging) in which a body tissue is irradiated with light in a narrower band than irradiation light (that is, white light) in normal observation using wavelength dependence of absorption of light in the body tissue, so that a predetermined tissue such as a blood vessel on a mucosal surface layer is imaged with high contrast is performed. Alternatively, in the special light observation, fluorescence observation in which an image is obtained using fluorescence generated by irradiation with excitation light may be performed. In the fluorescence observation, it is possible to irradiate the body tissue with excitation light and observe the fluorescence from the body tissue (autofluorescence observation), to obtain a fluorescence image by locally injecting a reagent such as indocyanine green (ICG) into the body tissue and irradiating the body tissue with excitation light corresponding to the fluorescence wavelength of the reagent, or the like. The light source device 11203 may be configured to be able to supply the narrow band light and/or the excitation light corresponding to such special light observation.

Figure 28:
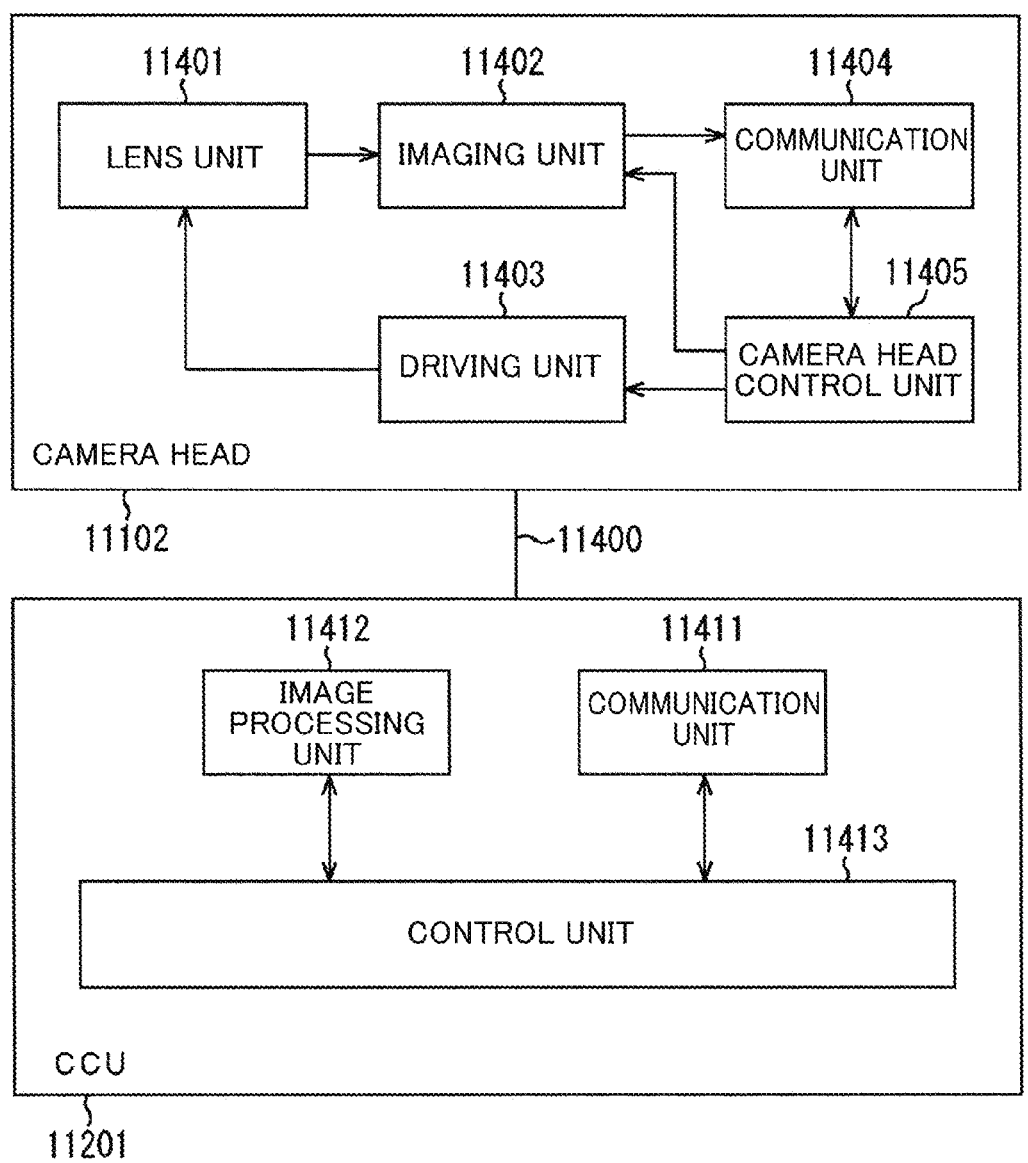
FIG. 28 is a block diagram illustrating an example of functional configurations of a camera head and a CCU.

FIG. 28 is a block diagram illustrating an example of a functional configuration of the camera head 11102 and CCU 11201 illustrated in FIG. 27.

The camera head 11102 includes a lens unit 11401, an imaging unit 11402, a driving unit 11403, a communication unit 11404, and a camera head control unit 11405. The CCU 11201 has a communication unit 11411, an image processing unit 11412, and a control unit 11413. The camera head 11102 is connected to the CCU 11201 to be able to communicate with each other via a transmission cable 11400.

The lens unit 11401 is an optical system provided at a portion for connection to the lens barrel 11101. The observation light taken in from the distal end of the lens barrel 11101 is guided to the camera head 11102 and incident on the lens unit 11401. The lens unit 11401 is configured of a combination of a plurality of lenses including a zoom lens and a focus lens.

The number of imaging elements constituting the imaging unit 11402 may be one (so-called single-plate type) or plural (so-called multi-plate type). When the imaging unit 11402 is configured as a multi-plate type, image signals corresponding to R, G, and B, for example, may be generated by the respective imaging elements and may be combined to obtain a color image. Alternatively, the imaging unit 11402 may be configured to include a pair of image sensors for respectively acquiring right-eye image signals and left-eye image signals corresponding to 3D (dimensional) display. By performing the 3D display, the operator 11131 can understand a depth of a living tissue in the operation site more accurately. Also, in a case in which the imaging unit 11402 is configured as the multi-plate type, a plurality of lens units 11401 may be provided corresponding to each image sensor.

Further, the imaging unit 11402 may not be provided in the camera head 11102. For example, the imaging unit 11402 may be provided immediately after the objective lens inside the lens barrel 11101.

The driving unit 11403 includes an actuator, and moves the zoom lens and the focus lens of the lens unit 11401 by a predetermined distance along an optical axis under the control of the camera head control unit 11405. Accordingly, the magnification and focus of the image captured by the imaging unit 11402 can be adjusted appropriately.

The communication unit 11404 is configured of a communication device for transmitting or receiving various pieces of information to or from the CCU 11201. The communication unit 11404 transmits the image signal obtained from the imaging unit 11402 as RAW data to the CCU 11201 via the transmission cable 11400.

The communication unit 11404 also receives a control signal for controlling the driving of the camera head 11102 from the CCU 11201 and supplies the control signal to the camera head control unit 11405. The control signal includes, for example, information on the imaging conditions such as information indicating that the frame rate of the captured image is designated, information indicating that the exposure value at the time of imaging is designated, and/or information indicating that the magnification and the focus of the captured image are designated.

The imaging conditions such as the frame rate, the exposure value, the magnification, and the focus may be appropriately designated by the user, or may be automatically set by the control unit 11413 of the CCU 11201 on the basis of the acquired image signal. In the latter case, a so-called auto exposure (AE) function, auto focus (AF) function, and auto white balance (AWB) function are mounted in the endoscope 11100.

The camera head control unit 11405 controls the driving of the camera head 11102 on the basis of the control signal from the CCU 11201 received via the communication unit 11404.

The communication unit 11411 includes a communication device for transmitting and receiving various pieces of information to and from the camera head 11102. The communication unit 11411 receives the image signal transmitted from the camera head 11102 via the transmission cable 11400.

Further, the communication unit 11411 transmits a control signal for controlling driving of the camera head 11102 to the camera head 11102. The image signal and the control signal can be transmitted via electric communication, optical communication, or the like.

The image processing unit 11412 performs various image processing on the image signal that is the RAW data transmitted from the camera head 11102.

The control unit 11413 performs various controls regarding imaging of the surgical part or the like using the endoscope 11100 and a display of a captured image obtained by imaging the surgical part or the like. For example, the control unit 11413 generates the control signal for controlling the driving of the camera head 11102.

Further, the control unit 11413 causes the display device 11202 to display the captured image obtained by imaging the surgical part or the like on the basis of the image signal subjected to the image processing by the image processing unit 11412. In this case, the control unit 11413 may recognize various objects in the captured image using various image recognition technologies. For example, the control unit 11413 can detect shapes and colors of edges of an object included in the captured image, thereby recognizing surgical instruments such as forceps, a specific living body part, bleeding, mist at the time of using the energized treatment tool 11112, and the like. The control unit 11413 may use the recognition results to superimpose and display various types of surgery support information on the image of the surgical site when the captured image is displayed on the display device 11202. By displaying the surgery support information in a superimposed manner and presenting it to the operator 11131, a burden on the operator 11131 can be reduced, and the operator 11131 can reliably proceed with the surgery.

The transmission cable 11400 that connects the camera head 11102 to the CCU 11201 is an electrical signal cable compatible with communication of an electrical signal, an optical fiber compatible with optical communication, or a composite cable thereof.

Here, in the illustrated example, wired communication is performed using the transmission cable 11400, but the communication between the camera head 11102 and the CCU 11201 may be performed wirelessly.

The example of the endoscopic surgery system to which the technology according to the present disclosure can be applied has been described above. The technology according to the present disclosure may be applied to the imaging unit 11402 of the camera head 11102 among the configurations described above. Specifically, the solid-state imaging device 1 in FIG. 1 can be applied to the imaging unit 11402. It is possible to obtain a high-quality surgical site image from such an imaging unit 11402 by applying the technology according to the present disclosure to the imaging unit 11402, and thus an operator can reliably confirm a surgical site.

Here, although the endoscopic surgery system has been described as an example, the technology according to the present disclosure may be applied to, for example, a microscopic surgery system.

Although the embodiments of the present disclosure have been described above, the technical scope of the present disclosure is not limited to the above-described embodiments and can be modified in various manners without departing from essential characteristics of the present disclosure. In addition, components in different embodiments and modified examples may be appropriately combined.

The advantages described in the present specification are merely exemplary and not limited, and other advantages may be obtained.

Meanwhile, the present technology may also have the following configuration.

(1)

A solid-state imaging device including:
- a photoelectric conversion portion that includes a first electrode, a photoelectric conversion layer electrically connected to the first electrode, and a second electrode provided on a surface on a light incidence side of the photoelectric conversion layer, wherein the photoelectric conversion layer has a protrusion region that protrudes from the second electrode when seen in a plan view.

(2)

The solid-state imaging device according to (1), wherein the photoelectric conversion portion further includes a charge storage layer provided on a surface on a side opposite to the light incidence side in the photoelectric conversion layer, and a charge storage electrode disposed to face the charge storage layer through an insulating layer.

(3)

The solid-state imaging device according to (2), wherein
- a plurality of the photoelectric conversion portions are provided, and
- the plurality of photoelectric conversion portions share one floating diffusion.

(4)

The solid-state imaging device according to any one of (1) to (3), wherein
the protrusion region of the photoelectric conversion layer is configured such that a portion of the photoelectric conversion layer which is in contact with the second electrode and a surface on the light incidence side are substantially flush with each other.

(5)

The solid-state imaging device according to any one of (1) to (3), wherein
the protrusion region of the photoelectric conversion layer is configured such that a surface on the light incidence side protrudes from a portion of the photoelectric conversion layer which is in contact with the second electrode.

(6)

The solid-state imaging device according to any one of (1) to (5), wherein
the photoelectric conversion layer of the photoelectric conversion portion is constituted by an organic semiconductor material.

(7)

The solid-state imaging device according to any one of (1) to (6), further including:
another photoelectric conversion portion which is provided on the light incidence side of the photoelectric conversion portion and performs photoelectric conversion of light having a wavelength different from that of the photoelectric conversion portion.

(8)

The solid-state imaging device according to (7), wherein
the photoelectric conversion layer of the other photoelectric conversion portion is constituted by an organic semiconductor material.

(9)

A method of manufacturing a solid-state imaging device, the method including:
forming a first electrode;
forming a removal material above the first electrode;
forming a second electrode on a surface of the removal material;
removing the removal material; and
forming a photoelectric conversion layer in a region in which the removal material is removed.

(10)

The method of manufacturing the solid-state imaging device according to (9), further including:
performing annealing at a predetermined temperature before the forming of the photoelectric conversion layer.

(11)

The method of manufacturing the solid-state imaging device according to (10), wherein
the annealing is performed at a temperature higher than a heat-resistant temperature of the photoelectric conversion layer.

(12)

The method of manufacturing the solid-state imaging device according to any one of (9) to (11), wherein
the forming of the photoelectric conversion layer is performed by injecting a liquid raw material into the region in which the removal material is removed from an injection port formed so as to exclude the second electrode.

(13)

Electronic equipment including:
a photoelectric conversion portion that includes a first electrode, a photoelectric conversion layer electrically connected to the first electrode, and a second electrode provided on a surface on a light incidence side of the photoelectric conversion layer, wherein the photoelectric conversion layer includes a solid-state imaging device having a protrusion region that protrudes from the second electrode when seen in a plan view.

(14)

The electronic equipment according to (13), wherein
the photoelectric conversion portion further includes a charge storage layer provided on a surface on a side opposite to the light incidence side in the photoelectric conversion layer, and a charge storage electrode disposed so as to face the charge storage layer through an insulating layer.

(15)

The electronic equipment according to (14), wherein
a plurality of the photoelectric conversion portions are provided, and
the plurality of photoelectric conversion portions share one floating diffusion.

(16)

The electronic equipment according to any one of (13) to (15), wherein
the protrusion region of the photoelectric conversion layer is configured such that a portion of the photoelectric conversion layer which is in contact with the second electrode and a surface on the light incidence side are substantially flush with each other.

(17)

The electronic equipment according to any one of (13) to (15), wherein
the protrusion region of the photoelectric conversion layer is configured such that a surface on the light incidence side protrudes from a portion of the photoelectric conversion layer which is in contact with the second electrode.

(18)

The electronic equipment according to any one of (13) to (17), wherein
the photoelectric conversion layer of the photoelectric conversion portion is constituted by an organic semiconductor material.

(19)

The electronic equipment according to any one of (13) to (18), further including:
another photoelectric conversion portion which is provided on the light incidence side of the photoelectric conversion portion and performs photoelectric conversion of light having a wavelength different from that of the photoelectric conversion portion.

(20)

The electronic equipment according to (19), wherein
the photoelectric conversion layer of the other photoelectric conversion portion is constituted by an organic semiconductor material.

REFERENCE SIGNS LIST

1 Solid-state imaging device
10 Pixel array portion
11 Unit pixel
20, 30 Photoelectric conversion portion
21, 31 First electrode
22, 32 Charge storage electrode
23, 33 Charge storage layer 24, 34 Photoelectric conversion layer
24a, 34a Protrusion region
25, 35 Second electrode
40 Insulating layer
50 Semiconductor layer
51, 52 Floating diffusion
100 Electronic equipment
R Removal material

The invention claimed is:

1. A solid-state imaging device, comprising:
a first photoelectric conversion portion that includes:
   a first electrode;
   a first photoelectric conversion layer electrically connected to the first electrode; and
   a second electrode on a first surface of the first photoelectric conversion layer, wherein
      the second electrode is on a light incidence side of the first photoelectric conversion portion, and
      the first photoelectric conversion layer has a protrusion region; and
a second photoelectric conversion portion on the light incidence side of the first photoelectric conversion portion, wherein
   the second photoelectric conversion portion includes a third electrode, and
   the protrusion region of the first photoelectric conversion layer protrudes from a portion of the first photoelectric conversion layer and reaches to the third electrode.

2. The solid-state imaging device according to claim 1, further comprising an insulating layer, wherein
the insulating layer surrounds the first photoelectric conversion portion, and
the first photoelectric conversion portion further includes:
   a charge storage layer on a second surface of the first photoelectric conversion layer, wherein the second surface of the first photoelectric conversion layer is on a side opposite to the light incidence side of the first photoelectric conversion portion; and
   a charge storage electrode that faces the charge storage layer through the insulating layer.

3. The solid-state imaging device according to claim 2, further comprising:
a floating diffusion connected to the first electrode; and
a plurality of photoelectric conversion portions that shares the floating diffusion, wherein the plurality of photoelectric conversion portions includes the first photoelectric conversion portion.

4. The solid-state imaging device according to claim 1, wherein
the portion of the first photoelectric conversion layer is in contact with the second electrode,
the portion of the first photoelectric conversion layer is flush with the first surface of the first photoelectric conversion portion, and
the first surface of the first photoelectric conversion layer is on the light incidence side of the first photoelectric conversion portion.

5. The solid-state imaging device according to claim 1, wherein the first photoelectric conversion layer of the first photoelectric conversion portion includes an organic semiconductor material.

6. The solid-state imaging device according to claim 1, wherein
the second photoelectric conversion portion is configured to perform photoelectric conversion of a first light,
the first light has a wavelength different from a wavelength of a second light, and
the second light is associated with the first photoelectric conversion portion.

7. The solid-state imaging device according to claim 6, wherein
the second photoelectric conversion portion further includes a second photoelectric conversion layer, and
the second photoelectric conversion layer includes an organic semiconductor material.

8. A method of manufacturing a solid-state imaging device, the method comprising:
forming a first electrode;
forming a removal material above the first electrode;
forming a second electrode on a surface of the removal material;
removing the removal material; and
forming a photoelectric conversion layer in a region where the removal material is removed.

9. The method of manufacturing the solid-state imaging device according to claim 8, further comprising performing annealing at a temperature before the forming of the photoelectric conversion layer.

10. The method of manufacturing the solid-state imaging device according to claim 9, wherein the temperature is higher than a heat-resistant temperature of the photoelectric conversion layer.

11. The method of manufacturing the solid-state imaging device according to claim 8, wherein
the forming of the photoelectric conversion layer is performed by injecting a liquid raw material, into the region where the removal material is removed, from an injection port, and
the removal material is formed to exclude the second electrode.

12. An electronic equipment, comprising:
a first photoelectric conversion portion that includes:
   a first electrode;
   a photoelectric conversion layer electrically connected to the first electrode; and
   a second electrode on a surface of the photoelectric conversion layer, wherein
      the second electrode is on a light incidence side of the first photoelectric conversion portion, and
      the photoelectric conversion layer has a protrusion region; and
a second photoelectric conversion portion on the light incidence side of the first photoelectric conversion portion, wherein
   the second photoelectric conversion portion includes a third electrode, and
   the protrusion region of the photoelectric conversion layer protrudes from a portion of the photoelectric conversion layer and reaches to the third electrode.

* * * * *